(12) United States Patent
Lavis et al.

(10) Patent No.: US 12,360,106 B2
(45) Date of Patent: Jul. 15, 2025

(54) PHOTOCHROMIC XANTHENE FLUOROPHORES AND THEIR UTILITY IN LIVE-CELL IMAGING BEYOND THE DIFFRACTION LIMIT

(71) Applicant: HOWARD HUGHES MEDICAL INSTITUTE, Chevy Chase, MD (US)

(72) Inventors: Luke Lavis, Leesburg, VA (US); Fadi M. Jradi, Arlington, VA (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 884 days.

(21) Appl. No.: 17/300,404

(22) Filed: Jun. 16, 2021

(65) Prior Publication Data
US 2021/0318293 A1    Oct. 14, 2021

Related U.S. Application Data

(62) Division of application No. 15/932,629, filed on Mar. 28, 2018, now Pat. No. 11,067,566.

(60) Provisional application No. 62/601,808, filed on Mar. 31, 2017.

(51) Int. Cl.
| | |
|---|---|
| *G01N 33/533* | (2006.01) |
| *C07D 405/14* | (2006.01) |
| *C07D 473/18* | (2006.01) |
| *C07D 491/107* | (2006.01) |
| *C07D 491/147* | (2006.01) |
| *C07D 491/22* | (2006.01) |
| *C07D 493/10* | (2006.01) |
| *C09B 57/02* | (2006.01) |
| *C09K 11/06* | (2006.01) |

(52) U.S. Cl.
CPC ......... *G01N 33/533* (2013.01); *C07D 405/14* (2013.01); *C07D 473/18* (2013.01); *C07D 491/107* (2013.01); *C07D 491/147* (2013.01); *C07D 491/22* (2013.01); *C07D 493/10* (2013.01); *C09B 57/02* (2013.01); *C09K 11/06* (2013.01); *C09K 2211/1018* (2013.01)

(58) Field of Classification Search
CPC .................................................... G01N 33/533
See application file for complete search history.

(56) References Cited

U.S. PATENT DOCUMENTS 11,067,566 B2 *    7/2021   Lavis ................... C07D 405/14

FOREIGN PATENT DOCUMENTS

WO     WO 2015/153813 A1    10/2015

OTHER PUBLICATIONS

Dey et. al. (Dalton Trans., 2017,46, 2524-2531) (Year: 2017).*
Folling et al., "Photochromic Rhodamines Provide Nanoscopy with Optical Sectioning", Angew. Chem. Int. Ed. (2007) vol. 46, pp. 6266-6270.
Bossi et al., "Multicolor Far-Field Fluorescence Nanoscopy through Isolated Detection of Distinct Molecular Species", Nano Letters (2008) vol. 8, pp. 2463-2468.
Folling et al., "Fluorescence Nanoscopy with Optical Sectioning by Two-Photon Induced Molecular . . . ", ChemPhysChem (2008) vol. 9, pp. 321-326.
Belov et al., "Rhodamine Spiroamides for Multicolor Single-Molecule Switching Fluorescent Nanoscopy", Chem. Eur. J. (2009) vol. 15, pp. 10762-10776.
Lee et al., "Small-Molecule Labeling of Live Cell Surfaces for Three-Dimensional Super-Resolution Microscopy . . . ", J. Am. Chem. Soc. (2014) vol. 136, pp. 14003-14006.
Wan et al., "Cascade Off-On-Off Fluorescent Probe: Duel Detection of Trivalent Ions and phophate Ions", RSC Adv. (2014) vol. 4, pp. 29479-29484.
Tang et al., "A New Rhodamine B-coumarin Fluorochrome for Colorimetric Recognition . . . ", Bulletin-Korean Chemical Society (2011) vol. 32, No. 9, pp. 3400-3404.
An et al., "A novel off-on fluorescence chemosensor for $Ca^{2+}$ based on Rhodamine-Coumarin Schiff . . . ", J. of Luminescence (2013) vol. 139, pp. 79-83.
Qin et al., "FRET-based rhodamine-coumarin conjugate as a $Fe^{3+}$ selective ratiometric fluorescent sensor in aqueous media", Tetrahedron Letters (2015) vol. 56, pp. 5024-5029.

* cited by examiner

*Primary Examiner* — John S Kenyon
*Assistant Examiner* — Rehana Ismail
(74) *Attorney, Agent, or Firm* — McKinney Law Group APC; Jeffrey A. McKinney

(57) ABSTRACT

The present invention is generally directed to novel fluorophores and their use in imaging methods. In one case, the present invention provides a compound according to the structure shown in FIG. 20A. In another case, the present invention provides a method of imaging one or more cellular structures within one or more cells using a compound of the structure shown in FIG. 20A.

5 Claims, 33 Drawing Sheets

A

B a b c d a. *tert*-butyl ethyl malonate, piperidine, acetonitrile, RT, overnight
b. CbzNH$_2$, Pd$_2$(dba)$_3$, Xantphos, CsCO$_3$, dioxane, 100 °C, 2h.
c. TFA, DCM, RT.
d. DCC, DMAP, DMF, RT, HaloTag(O$_2$)amine TFA salt.
e. H$_2$ balloon, Pd/C, EtOAc.
f. HATU, DIEA, DMF, JF549-CO$_2$H, RT.

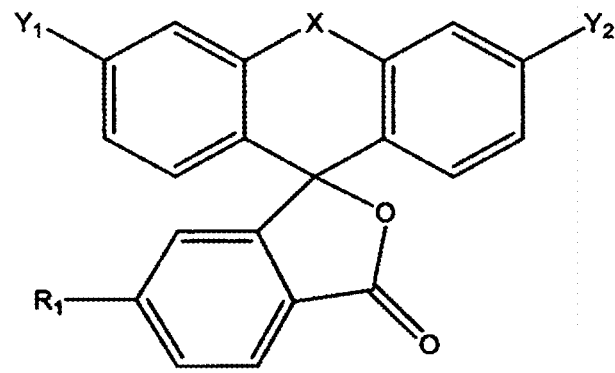
FIG. 18A
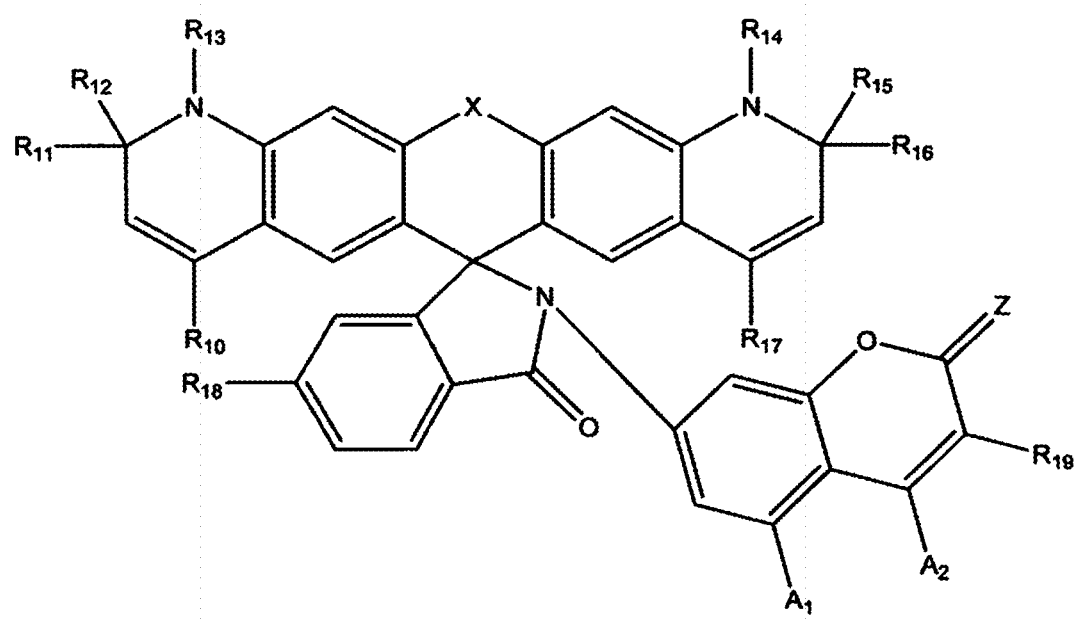
FIG. 18B
FIG. 18

FIG. 20B  FIG. 20C

SCHEME 1 (cont'd "1")

S8: X = O

PC-JF549-Tx: R = Tx; X = O a. i) NaOH, MeOH/THF RT, 24h; ii) HCl, 30 min.
b. i) DCC, DMAP, DMF, DIEA, RT, 1h; ii) HTL, 24h.
c. HATU, DIEA, DMF, 7-Amino-4-(trifluoromethyl)coumarin, RT, 4h.
d. HATU, DIEA, DMF, BG-NH$_2$, RT, 4h.
e. TSTU, DIEA, DMF, R, 2h.
f. 8-Aminooctanoic acid, HATU, DIEA, DMF, RT, 24h.
g. docetaxel, HATU, DIEA, DMF, RT, 48h.
h. i) Oxalyl chloride, DCM, RT, 30 min; ii) 7-Amino-4-(trifluoromethyl)coumarin, TEA, RT, 1h SCHEME 3 (cont'd "1")

S9: 5'-isomer
S10: 6'-isomer

PC-AF594-NHS a. i. DSC, Et₃N, DMAP, DMF, RT, 1h; ii) NaOMe (25% wt in MeOH), 24h.
b. conc. H₂SO₄, RT, 72h.
c. HATU, DIEA, DMF, 7-Amino-4-(trifluoromethyl)coumarin, RT, 24h.
d. i) NaOH, MeOH/THF, RT, 24h; ii) HCl, RT, 2h.
e. TSTU, DIEA, DMF, RT, 2h.
f. HATU, DIEA, DMF, HTL, 24h.

HTL =

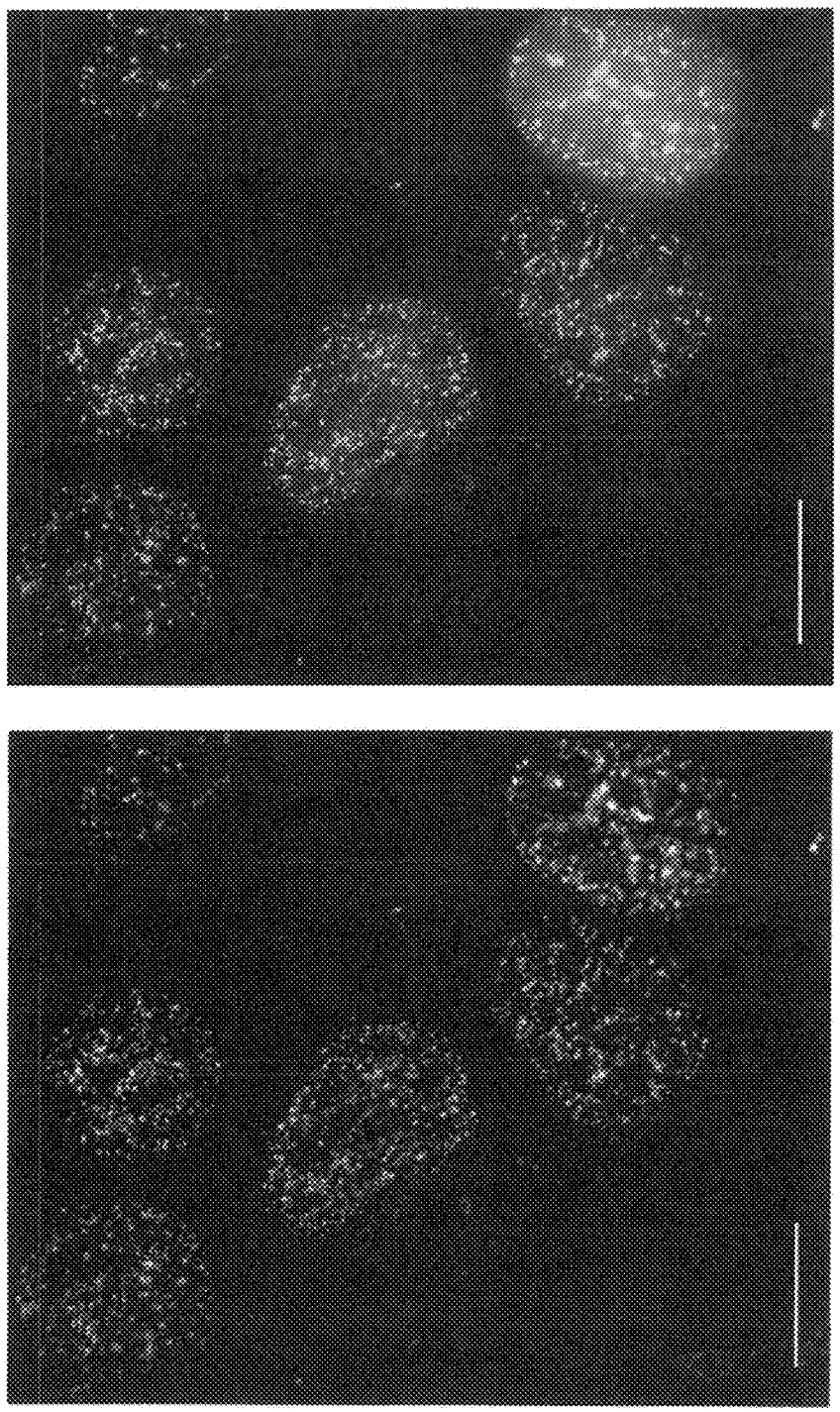
Figure 28. Super-resolution image (left) of live U2OS cells expressing H2B and labeled with PC-JF549-HT. Also showing is the overlay (right) with a diffraction limited fluorescence image with H2B expressing JF635-HT. Mean localization precision: 37 nm

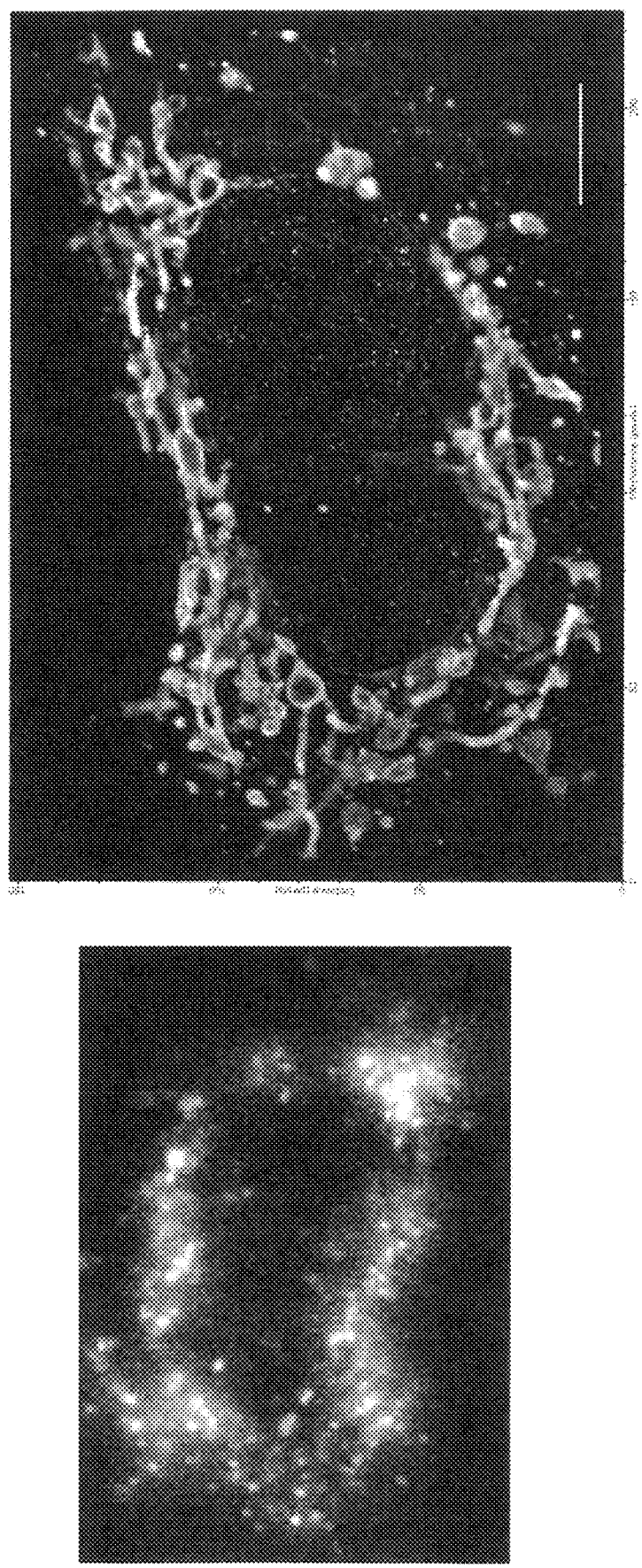
Figure 29. Super-resolution image of mitochondria expressing TOMM20 and labeled with PC-JF549-HT. The mean localization precision is: 28 nm. (a video that shows the dye blinking accompanies this figure).

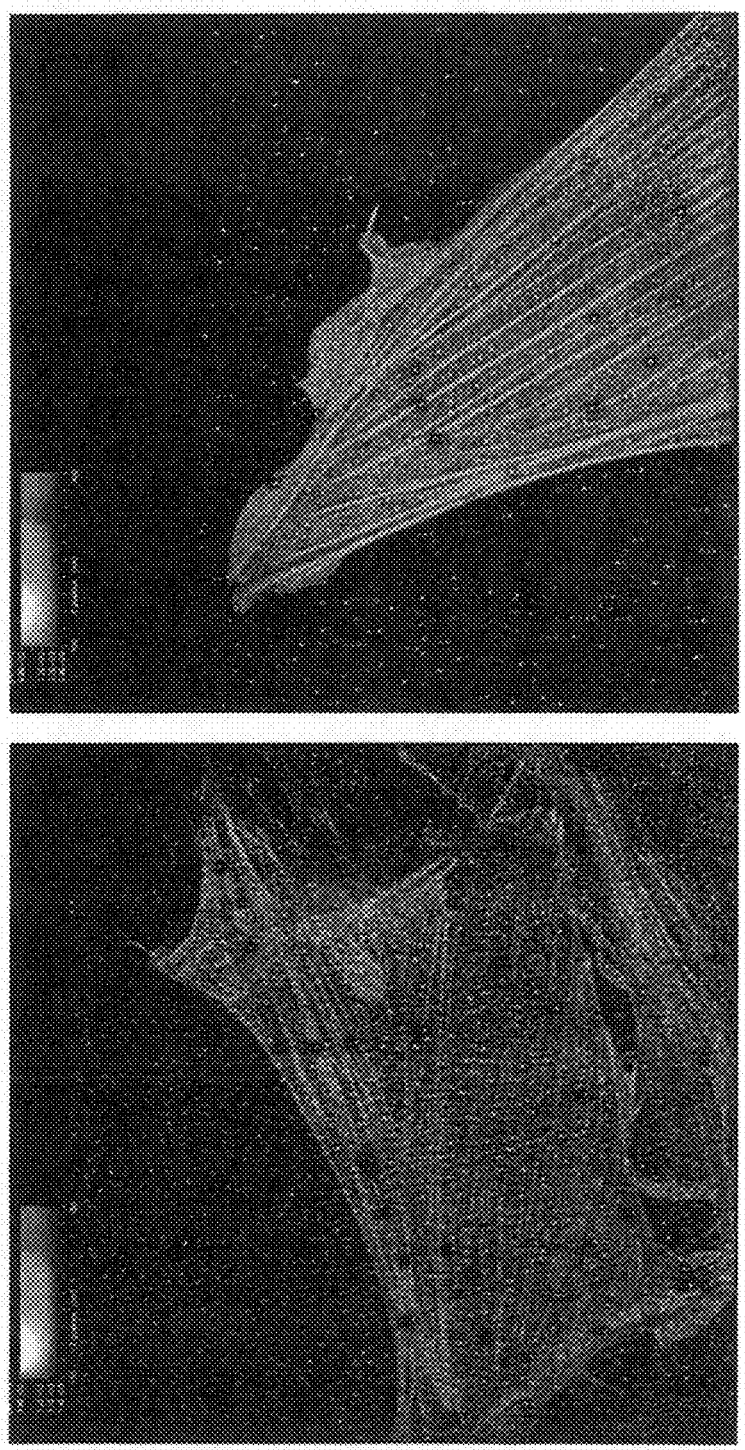
Figure 30. 3D super-resolution iPALM images of actin in ptk2 cells transfected with lifeact-halo, and labeled with the PC-JF549-HT.

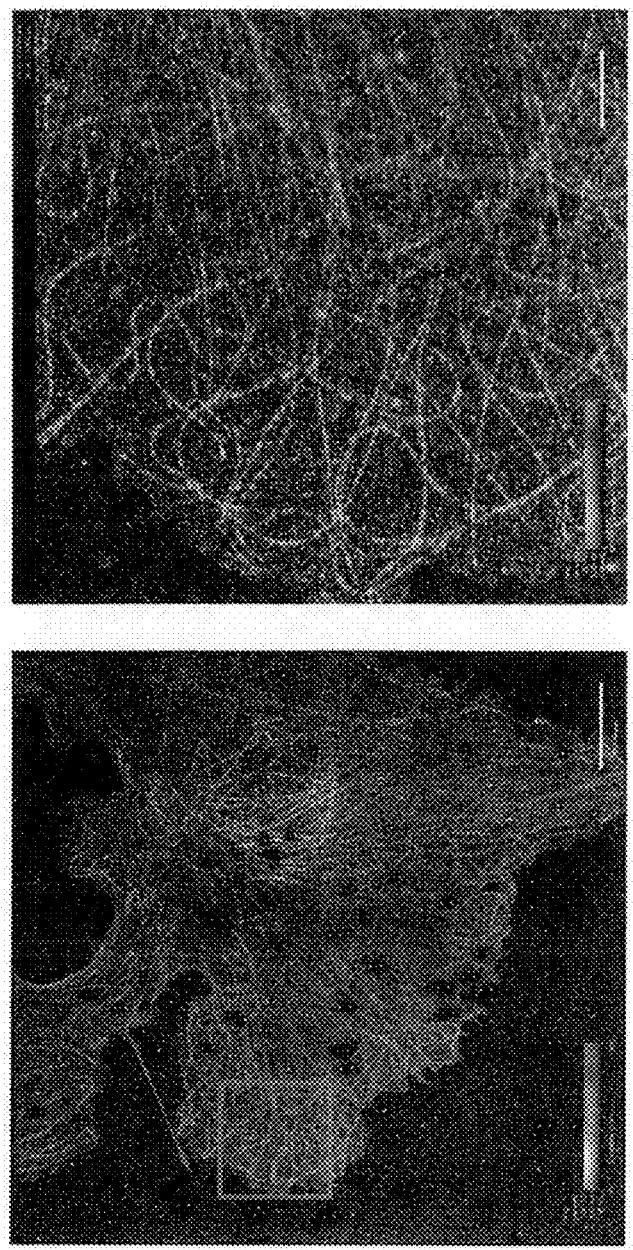
Figure 31. 3D super-resolution iPALM images of tubulin in ptk2 cells expressing HaloTag and labeled with the PC-JF549-HT.

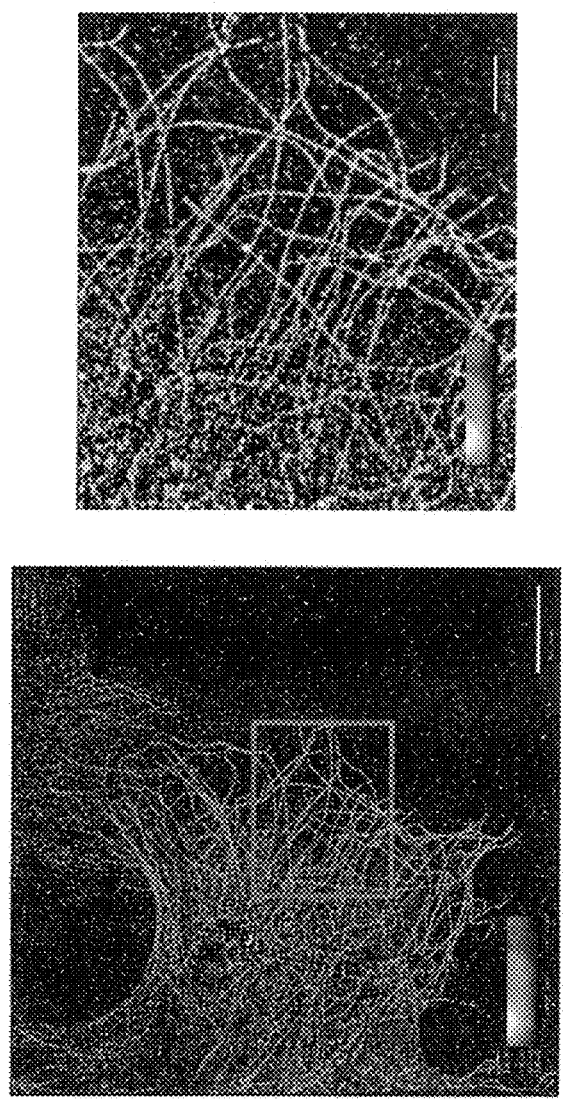
Figure 32. 3D super-resolution iPALM images of tubulin in COS7 cells targeted with an antibody which is labeled with PC-AF594-NHS.

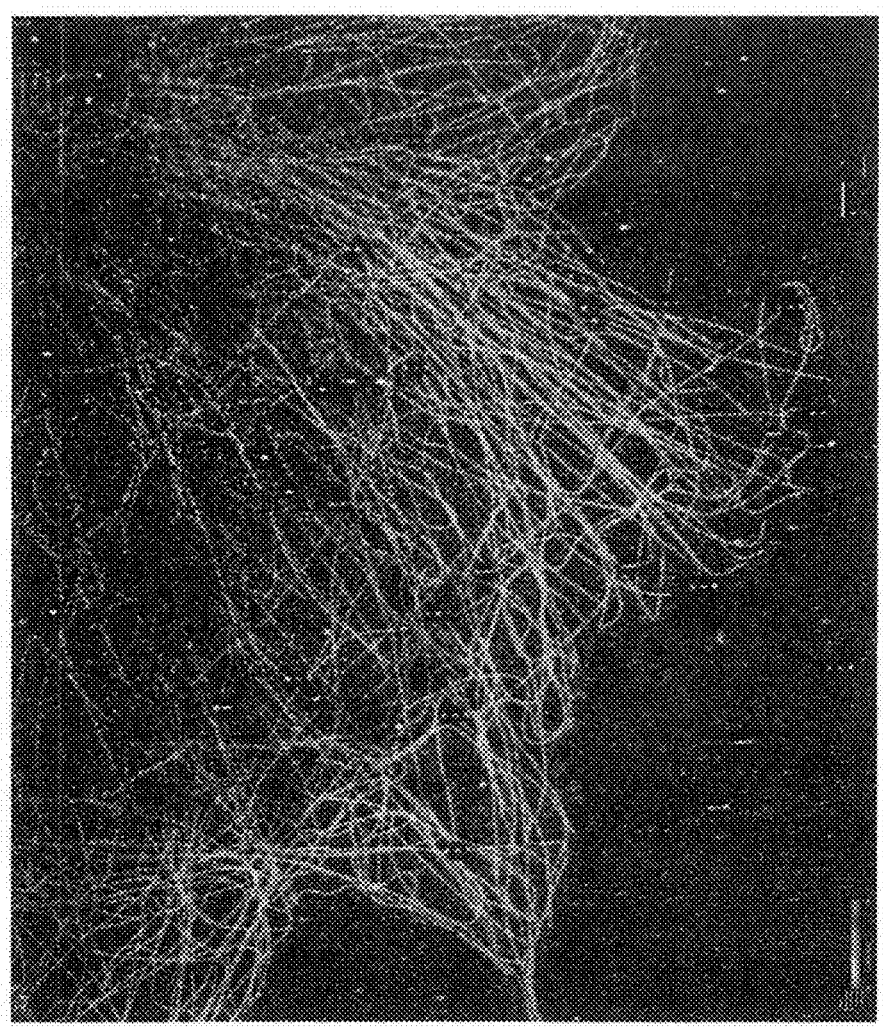
Figure 33. 3D super-resolution iPALM images of tubulin in COS7 cells targeted with an antibody which is labeled with PC-AF594-NHS.

PHOTOCHROMIC XANTHENE FLUOROPHORES AND THEIR UTILITY IN LIVE-CELL IMAGING BEYOND THE DIFFRACTION LIMIT

This application is a divisional of U.S. patent application Ser. No. 15/932,629, filed on Mar. 28, 2018, which claims the benefit of U.S. Provisional Patent Application No. 62/601,808, filed Mar. 31, 2017, each of which is incorporated by reference herein in its entirety.

FIELD OF THE INVENTION

The present invention is generally directed to novel fluorophores and their use in imaging methods.

BACKGROUND OF THE INVENTION

There have been reports of photochromic rhodamine dyes used in imaging methods. For instance, Fölling et al. ("Fölling 1") reports the synthesis and examination of photochromic rhodamine derivatives. "Fluorescence Nanoscopy with Optical Sectioning by Two-Photon Induced Molecular Switching Using Continuous-Wave Lasers", *Angew. Chem. Int. Ed.* 2007, 46, 6266-6270. According to Fölling 1, the rhodamine derivatives have the following properties: "This readily controllable photoswitchable compound has a high fluorescence quantum yield and high photochemical stability under single-molecule conditions. The resulting dramatic increase in n yields an average localization precision of approximately 10 nm. In conjunction with an optimized asynchronous image acquisition protocol, the large contrast between the two photochromic states involved minimizes the diffuse background and allows us to abandon the total internal reflection ("TIRF") recording schemes and mechanical object slicing that were mandatory in previous experiments." Id. at 6266. A type of fluorescent compound discussed in this reference is shown in FIG. 1.

Bossi et al. ("Bossi") examines the photochromic switching of particular rhodamine amides, including their use in multicolor single-molecule-switching-based nanoscopy. "Multicolor Far-Field Fluorescence Nanoscopy Through Isolated Detection of Distinct Molecular Species", *Nano Lett.* 2008, 8, 2463-2468. In the opinion of Bossi: "By combining the photoswitching and localization of individual fluorophores with spectroscopy on the single molecule level, we demonstrate simultaneous multicolor imaging with low crosstalk and down to 15 nm spatial resolution using only two detection color channels. The applicability of the method to biological specimens is demonstrated on mammalian cells. The combination of far-field fluorescence nanoscopy with the recording of a single switchable molecular species a at time opens up a new class of functional imaging techniques." Id. at Abstract. A type of fluorescent compound discussed in this reference is shown in FIG. 2.

Fölling et al. ("Fölling 2") analyzes the photochromic reaction of specific rhodamine amides. "Fluorescence Nanoscopy with Optical Sectioning by Two-Photon Induced Molecular Switching Using Continuous-Wave Lasers", *ChemPhysChem* 2008, 9, 321-326. In the words of Fölling 2: "During the last decade far-field fluorescence microscopy methods have evolved that have resolution far below the wavelength of light. To outperform the limiting role of diffraction, all these methods, in one way or another, switch the ability of a molecule to emit fluorescence. Here we present a novel rhodamine amide that can be photoswitched from a nonfluorescent to a fluorescent state by absorption of one or two photons from a continuous-wave laser beam. This bright marker enables strict control of on/off switching and provides single-molecule localization precision down to 15 nm in the focal plane. Two-photon induced non-linear photoswitching of this marker with continuous-wave illumination offers optical sectioning with simple laser equipment." Id. at Abstract. A type of fluorescent compound discussed in this reference is shown in FIG. 3.

Belov et al. ("Belov") discusses distinct rhodamine spirolactam compounds and their use in obtaining optical images. "Rhodamine Spiroamides for Multicolor Single-Molecule Switching Fluorescent Nanoscopy", *Chem. Eur. J.* 2009, 15, 10762-10776. As stated by Belov: "The design, synthesis, and evaluation of new rhodamine spiroamides are described. These molecules have applications in optical nanoscopy based on random switching of the fluorescent single molecules. The new markers may be used in (co)localization studies of various objects and their (mutual) positions and shape can be determined with a precision of a few tens of nanometers. Multicolor staining, good photoactivation, a large number of emitted photons, and selective chemical binding with amino or thiol groups were achieved due to the presence of various functional groups on the rhodamine spiroamides. Rigidized sulfonated xanthene fragment fused with six-membered rings, N,N'-bis(2,2,2-trifluoroethyl) groups, and a combination of additional double bonds and sulfonic acid groups with simple aliphatic spiroamide residue provide multicolor properties and improve performance of the rhodamine spiroamides in photoactivation and bioconjugation reactions." Id at Abstract. A type of fluorescent compound discussed in this reference is shown in FIG. 4.

Lee et al. ("Lee") discusses the use of certain rhodamine spirolactam derivatives. "Small-Molecule Labeling of Live Cell Surfaces for Three-Dimensional Super-Resolution Microscopy", *J. Am. Chem. Soc.* 2014,136, 14003-14006. Lee states: "Precise imaging of the cell surface of fluorescently labeled bacteria requires super-resolution methods because the size-scale of these cells is on the order of the diffraction limit. In this work, we present a photocontrollable small-molecule rhodamine spirolactam emitter suitable for non-toxic and specific labeling of the outer surface of cells for three-dimensional (3D) super-resolution (SR) imaging. Conventional rhodamine spirolactams photoswitch to the emitting form with UV light; however, these wavelengths can damage cells. We extended photo-switching to visible wavelengths >400 nm by iterative synthesis and spectroscopic characterization to optimize the substitution on the spirolactam." Id. at Abstract. A type of fluorescent compound discussed in this reference is shown in FIG. 5.

Wan et. al. ("Wan") reports a rhodamine B-based fluorescent probe and its application for the detection of trivalent ions. "Cascade Off-On-Off Fluorescent Probe: Duel Detection of Trivalent Ions and Phosphate Ions", *RSC Adv.* 2014, 4, 29479-29484. According to Wan: "A new rhodamine B-based fluorescent probe was developed for the selective cascade signaling of trivalent cations ($Fe^{3+}$, $Al^{3+}$, $Cr^{3+}$) and phosphate anion ($PO_4^{3-}$). Non-fluorescent rhodamine derivatives can selectively detect trivalent cations over some other metal ions in $CH_3CN$-Tris buffer (1/1, v/v, pH 7.0) solutions, leading to prominent fluorescence OFF-ON switching. The obtained probecation complex can subsequently serve as a sensitive and selective chemosensor for $PO_4^{3-}$, exhibiting complete signal quenching (fluorescence ON-OFF switching)." Id. at Abstract. A type of fluorescent compound discussed in this reference is shown in FIG. 6.

Despite reports of photochromic rhodamine dyes used in imaging methods, there is still a need in the art for novel fluorophores and their use in imaging methods.

BRIEF DESCRIPTION OF THE DRAWINGS

FIGS. 18-20 show general structures for compounds according to the present invention.

FIGS. 28-33 show further super-resolution images using compounds according to the present invention.

SUMMARY OF THE INVENTION

Figure 20A:
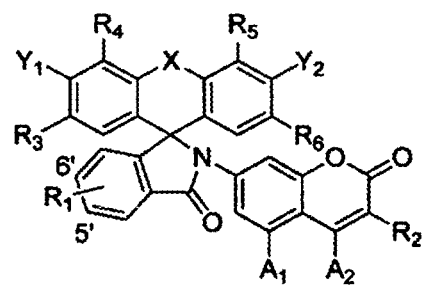
Figure 20:
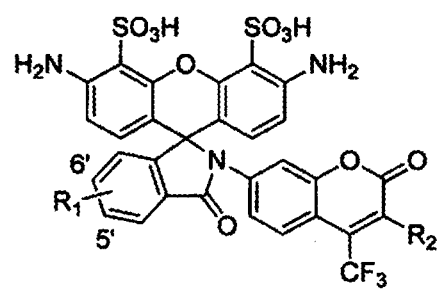
Figure 20:
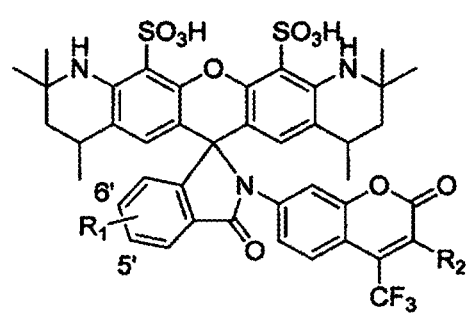
Figure 21:
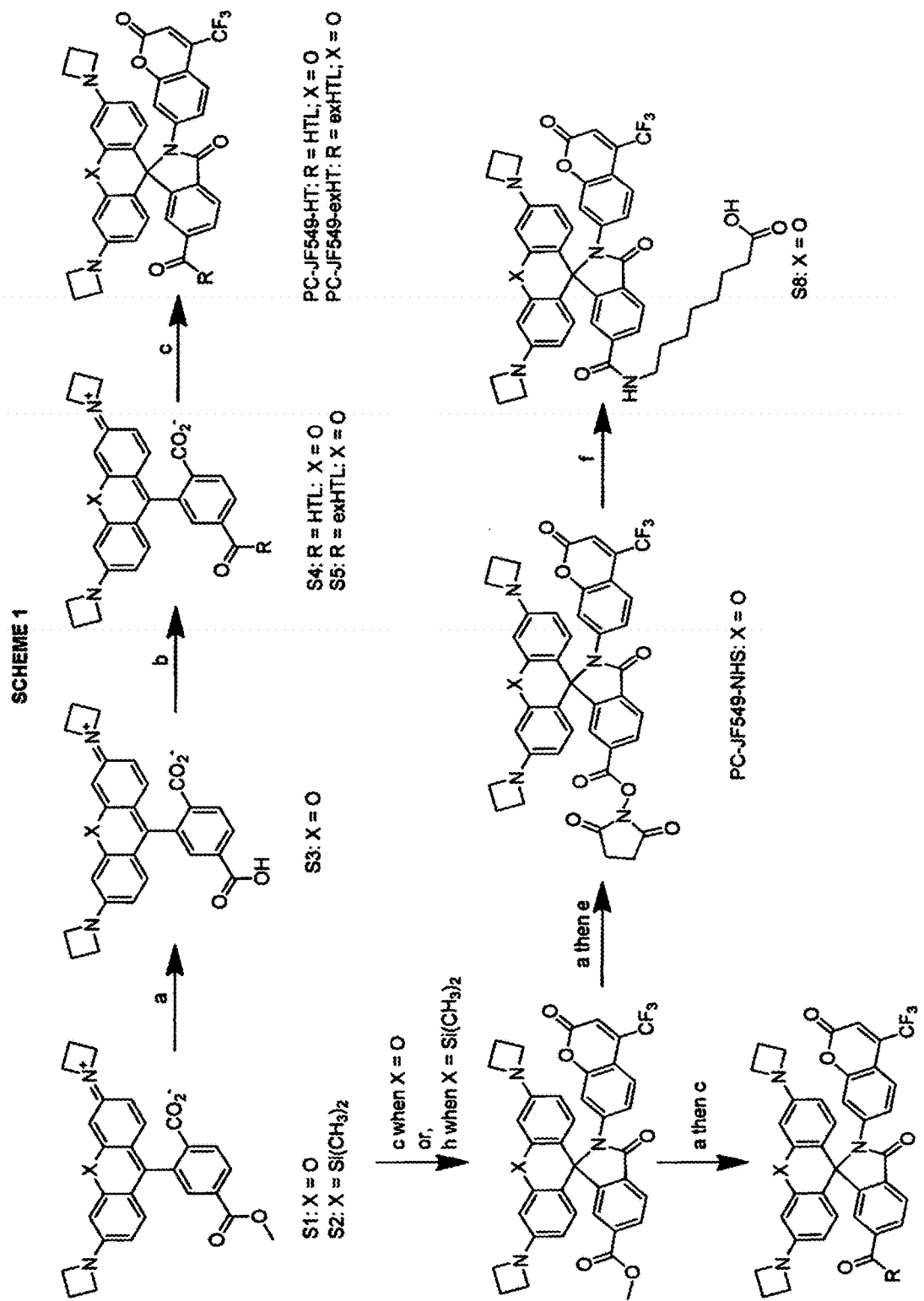
FIGS. 21-27 show further schemes for the synthesis of compounds according to the present invention.
Figure 22:
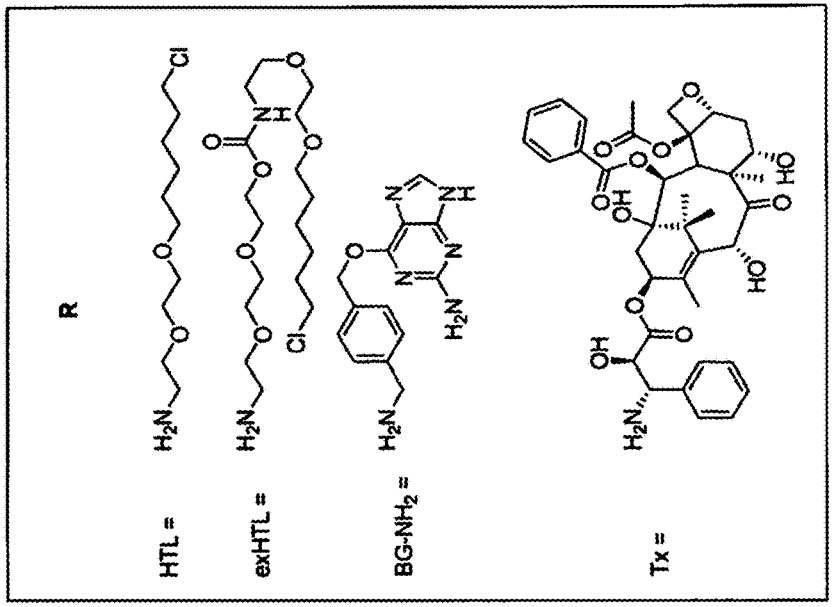
Figure 22:
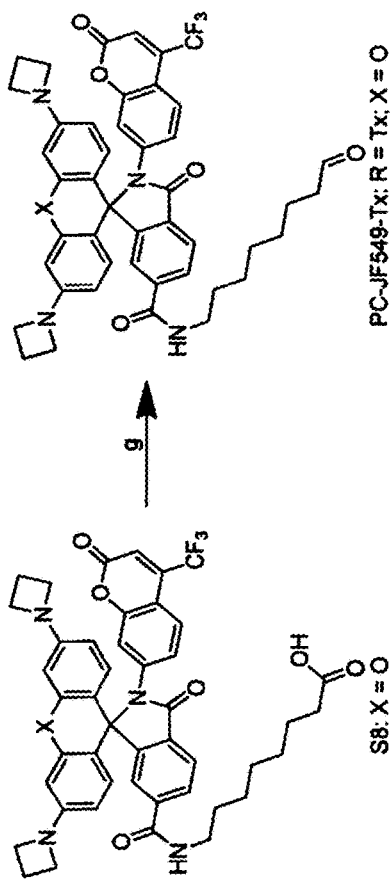
Figure 23:
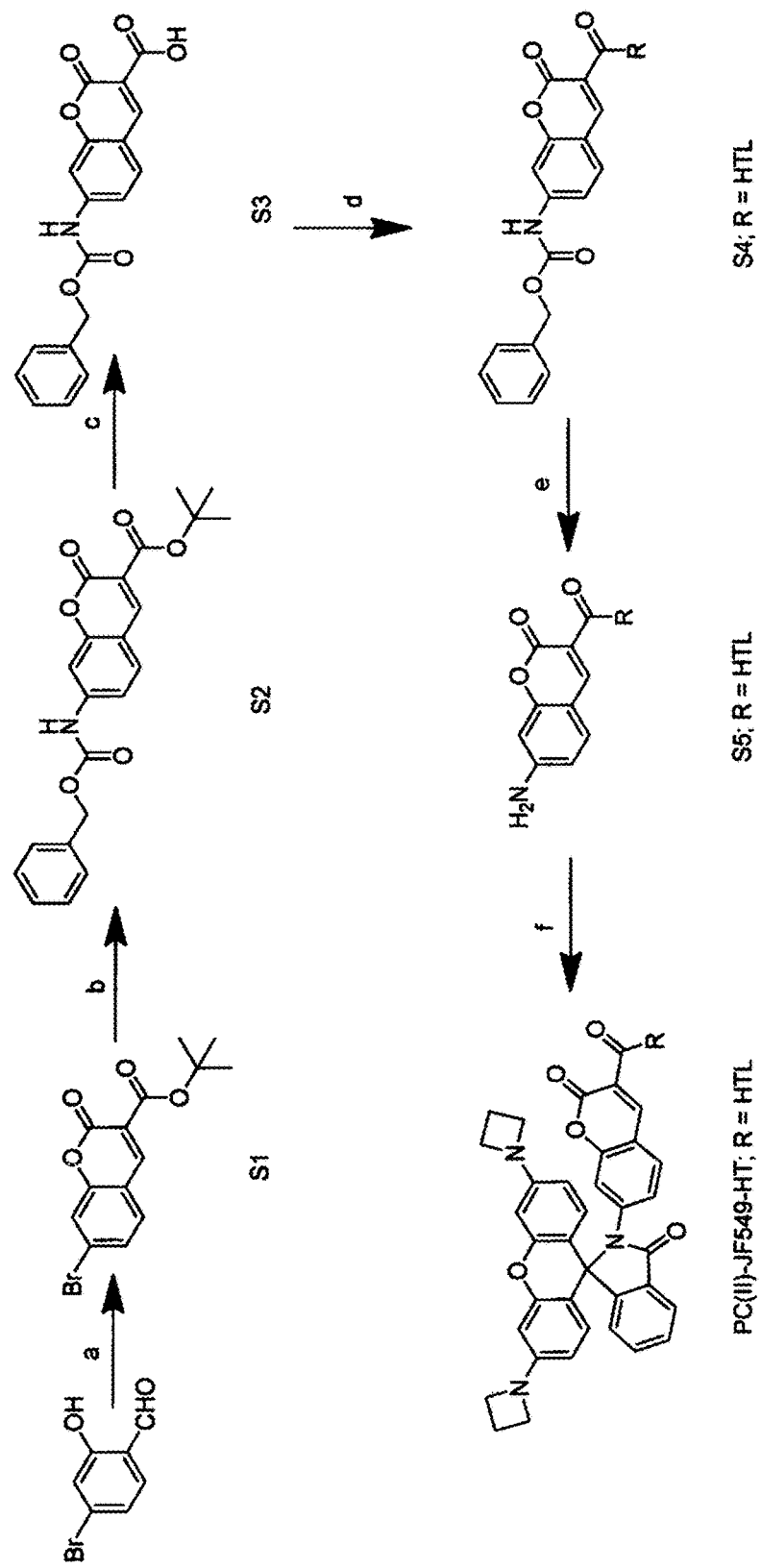
Figure 24:
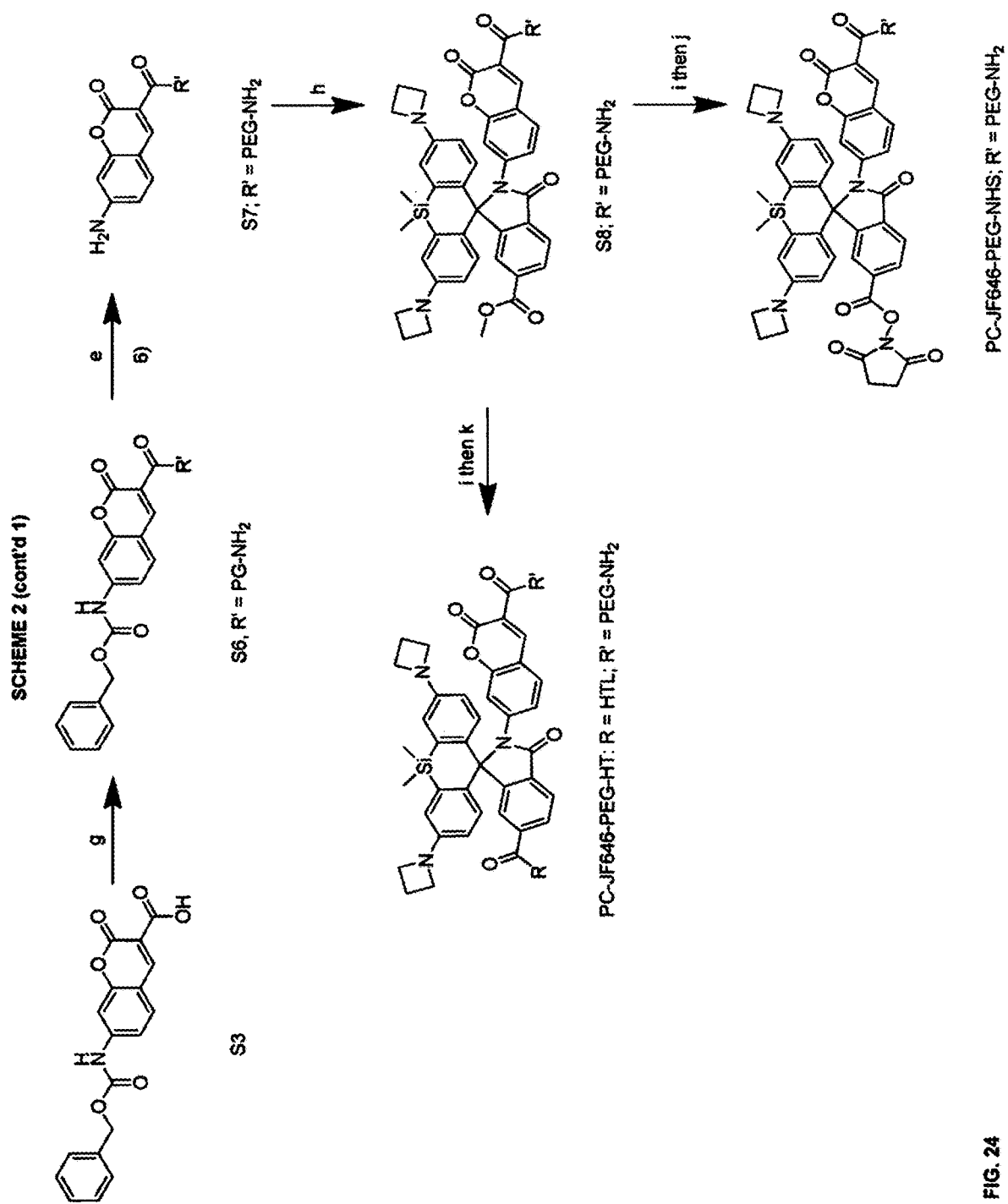
Figure 25:
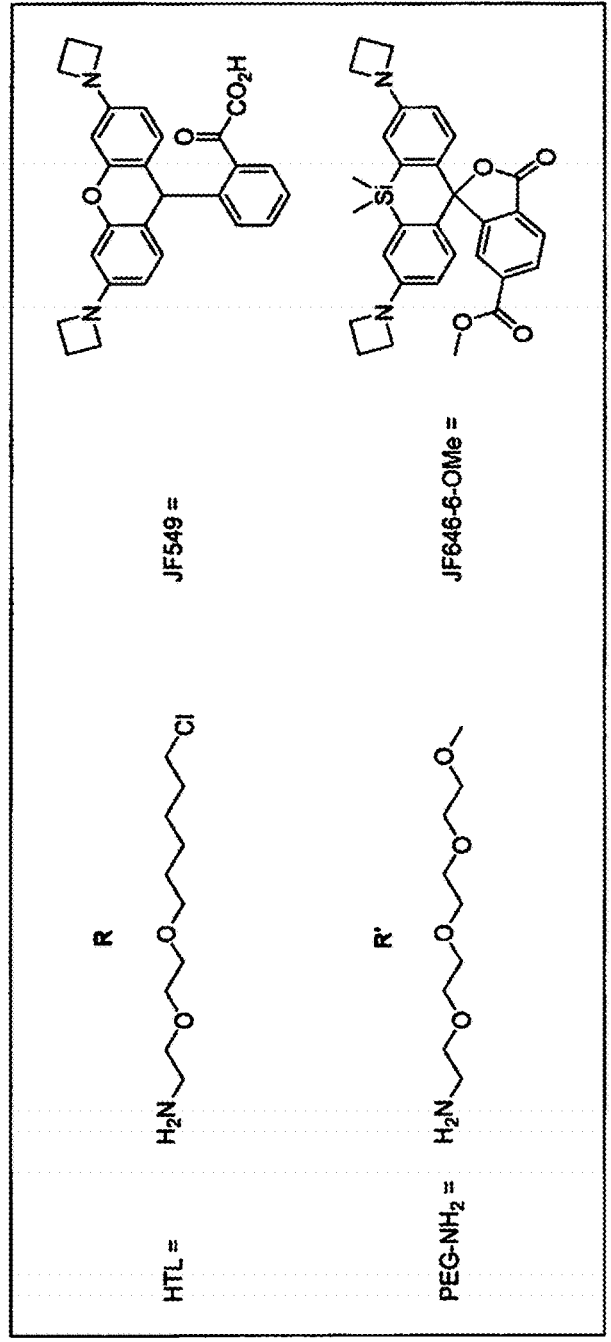

In one case, the present invention provides a compound according to the structure shown in FIG. 20A. The elements of the shown structure are defined as follows: X is O, N-alkyl, S, Si(alkyl)$_2$ or C(alkyl)$_2$; $Y_1$ is O, OH, NH$_2$, N(alkyl)$_2$ or one of the moieties shown in FIG. 9 (i.e., a, b, c, or d); $Y_2$ is O, OH, NH$_2$, N(alkyl)$_2$ or one of the moieties shown in FIG. 9 (i.e., a, b, c, or d); $R_1$, which can be a substitution at either the 5' position, the 6' position or both, is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$—(CH2)$_6$—Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl; $R_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$—(CH2)$_6$—Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl; $R_3$, $R_4$, $R_5$ and $R_6$ are independently hydrogen, alkyl, —SO$_3$H, halogen, or $R_3$ and $Y_1$ can form a ring, or $R_4$ and $Y_1$ can form a ring, or $R_5$ and $Y_2$ can form a ring, or $R_6$ and $Y_2$ can form a ring; $A_1$ is hydrogen, alkyl, alkenyl, alkynyl, heteroalkyl, heteroalkenyl, cycloalkyl, cycloalkenyl, heterocycloalkyl, heterocycloalkenyl, aromatic, heteroaromatic, substituted alkyl, substituted alkenyl, substituted alkynyl, substituted heteroalkyl, substituted heteroalkenyl, heterocycloalkyl, heterocycloalkenyl, substituted aromatic group, or substituted heteroaromatic group; $A_2$ is hydrogen, alkyl, alkenyl, alkynyl, heteroalkyl, heteroalkenyl, cycloalkyl, cycloalkenyl, heterocycloalkyl, heterocycloalkenyl, aromatic, heteroaromatic, substituted alkyl, substituted alkenyl, substituted alkynyl, substituted heteroalkyl, substituted heteroalkenyl, heterocycloalkyl, heterocycloalkenyl, substituted aromatic group, or substituted heteroaromatic group.

In another case, the present invention provides a method of imaging one or more cellular structures within one or more cells. The method includes the steps of:

a) labeling one or more cells with a compound according to the structure shown in FIG. 20A, where the elements of the shown structure are defined as follows: X is O, N-alkyl, S, Si(alkyl)$_2$ or C(alkyl)$_2$; $Y_1$ is O, OH, NH$_2$, N(alkyl)$_2$ or one of the moieties shown in FIG. 9 (i.e., a, b, c, or d); $Y_2$ is O, OH, NH$_2$, N(alkyl)$_2$ or one of the moieties shown in FIG. 9 (i.e., a, b, c, or d); $R_1$, which can be a substitution at either the 5' position, the 6' position or both, is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$—Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl; $R_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl; $R_3$, $R_4$, $R_5$ and $R_6$ are independently hydrogen, alkyl, —SO$_3$H, halogen, or $R_3$ and $Y_1$ can form a ring, or $R_4$ and $Y_1$ can form a ring, or R and $Y_2$ can form a ring, or $R_6$ and $Y_2$ can form a ring; $A_1$ hydrogen, alkyl, alkenyl, alkynyl, heteroalkyl, heteroalkenyl, cycloalkyl, cycloalkenyl, heterocycloalkyl, heterocycloalkenyl, aromatic, heteroaromatic, substituted alkyl, substituted alkenyl, substituted alkynyl, substituted heteroalkyl, substituted heteroalkenyl, heterocycloalkyl, heterocycloalkenyl, substituted aromatic group, or substituted heteroaromatic group; $A_2$ is hydrogen, alkyl, alkenyl, alkynyl, heteroalkyl, heteroalkenyl, cycloalkyl, cycloalkenyl, heterocycloalkyl, heterocycloalkenyl, aromatic, heteroaromatic, substituted alkyl, substituted alkenyl, substituted alkynyl, substituted heteroalkyl, substituted heteroalkenyl, heterocycloalkyl, heterocycloalkenyl, substituted aromatic group, or substituted heteroaromatic group.

to provide one or more labeled cells b) directing at least one beam of light to the one or more labeled cells, such that a detectable signal is produced from the one or more labeled cells;

c) recording the detectable signal, thereby imaging one or more structures within the one or more cells.

DETAILED DESCRIPTION OF THE INVENTION

"Acceptor" refers to a chemical entity that has a high affinity for electrons. It is typically a chemical entity that has at least one electron withdrawing group attached to another portion of a molecule through a point of unsaturation—e.g., olefin.

"Alkane" refers to an acyclic saturated hydrocarbon and having the general formula $C_nH_{2n+2}$. Examples of lower alkanes ($C_1$-$C_5$) include: methane; ethane; propane; butane; and pentane. Other, nonlimiting examples of alkanes are: hexane; heptane; octane; nonane; and decane.

"Alkyl" refers to an alkane missing one hydrogen and having the general formula $C_nH_{2n+1}$. Examples of lower alkyls (C1-C5) include: methyl; ethyl; propyl; butyl; and pentyl. Other, nonlimiting examples of alkyls are: hexyl; heptyl; octyl; nonyl; and decyl.

"Alkene" refers to an unsaturated hydrocarbon that contains at least one carbon-carbon double bond. Examples of lower alkenes (C2-C5) include: ethene; propene; butene; and pentene. Other, nonlimiting examples of alkenes include: hexene; heptene; octene; nonene; and decene.

"Alkenyl" refers to an alkene missing one hydrogen. Examples of lower alkenyls (C2-C5) include: ethenyl; propenyl; butenyl; and pentenyl. Other, nonlimiting examples of alkenyls include: hexenyl; heptenyl; octenyl; nonenyl; and decenyl.

"Alkyne" refers to an unsaturated hydrocarbon that contains at least one carbon-carbon triple bond. Examples of lower alkynes (C2-C5) include: ethyne; propyne; butyne; and pentyne. Other, nonlimiting examples of alkynes include: hexyne; heptyne; octyne; nonyne; and decyne.

"Alkynyl" refers to an alkyne missing one hydrogen. Examples of lower alkynyls (C2-C5) include: ethynyl; propynyl; butynyl; and pentynyl. Other, nonlimiting examples of alkynyls include: hexynyl; heptynyl; octynyl; nonynyl; and decynyl.

"Aromatic group" refers to a cyclic or multi-cyclic, planar molecule with a ring of resonance bonds that exhibit more stability than other geometric or connective arrangements with the same set of atoms. Nonlimiting examples of aromatic groups include: phenyl; naphthyl; anthracenyl; and phenanthrenyl.

"Cycloalkane" refers to an alkane arranged in a ring structure. The general formula for a cycloalkane is $C_nH_{2(n+1-r)}$. Nonlimiting examples of cycloalkanes include: cyclopropane; cyclobutane; cyclopentane; cyclohexane; cycloheptane; cyclooctane; cyclononane; and cyclodecane.

"Cycloalkene" refers to an alkene arranged in a ring structure. Nonlimiting examples of cycloalkenes include: cyclopropene; cyclobutene; cyclopentene; cyclohexene; cycloheptene; cyclooctene; cyclononene; and cyclodecene.

"Cycloalkenyl" refers to a cycloalkane missing one hydrogen atom. Nonlimiting examples of cycloalkenyls include: cyclopropenyl; cyclobutenyl; cyclopentenyl; cyclohexenyl; cycloheptenyl; cyclooctenyl; cyclononenyl; and cyclodecenyl.

"Cycloalkyl" refers to a cycloalkane missing one hydrogen and having the general formula $C_nH_{2n-1}$. Nonlimiting examples of cycloalkyls include: cyclopropyl; cyclobutyl; cyclopentyl; cyclohexyl; cycloheptyl; cyclooctyl; cyclononyl; and cyclodecyl.

"Electron withdrawing group" (i.e., "EWG") refers to an individual atom or functional group that withdraws electron density from a conjugated system. Nonlimiting examples of electron withdrawing groups include: —CN; —C(O)H; —C(O)-alkyl; —CO$_2$H; —CO$_2$-alkyl; —NO$_2$; —S(O)-alkyl; —S(O)$_2$-alkyl; and —SO$_3$H.

"HaloTag" refers to a protein tag including a modified haloalkane dehalogenase designed to covalently bind to synthetic ligands. The synthetic ligands comprise a chloroalkane linker attached to a variety of molecules. Nonlimiting examples of such molecules include: biotin; fluorescent dyes (e.g., Coumarin, Oregon Green, Alexa Fluor 488, diAcFAM and TMR); affinity handles; and solid surfaces. See, for example, Los et al., "A Novel Protein Labeling Technology for Cell Imaging and Protein Analysis", ACS Chem. Biol. 2008, 3, 373-382, which is incorporated-by-reference into this document for all purposes.

"Handle" refers to a biomolecule tag. Nonlimiting examples of handles include: a HaloTag; a SnapTag; a TMPTag; an NHS ester; and a β-lactamase.

"Heteroalkane" refers to an alkane, where one or more of the carbon atoms in the alkane is replaced by a heteroatom (e.g., O, S, N-alkyl). Nonlimiting examples of heteroalkanes include: $CH_3OCH_3$; $CH_3SCH_3$; $CH_3N(CH_3)CH_3$; $CH_3OCH_2CH_3$; $CH_3SCH_2CH_3$; $CH_3N(CH_3)$—$CH_2CH_3$; $CH_3CH_2OCH_2CH_3$; $CH_3CH_2SCH_2CH_3$; $CH_3CH_2N(CH_3)$ $CH_2CH_3$; $CH_3CH_2O$—$(CH_2CH_2O)_nCH_3$, where n is an integer ranging from 2 to 100; and $CH_3CH_2O$—$(CH_2CH_2O)_n$—$CH_2CH_3$, where n is an integer ranging from 2 to 100.

"Heteroalkyl" refers to a heteroalkane missing one hydrogen. Nonlimiting examples of heteroalkyls include: $CH_2OCH_3$; $CH_2SCH_3$; $CH_2N(CH_3)_2$; $CH_2OCH_2CH_3$; $CH_2SCH_2CH_3$; $CH_2N(CH_3)$—$CH_2CH_3$; $CH_2CH_2OCH_2CH_3$; $CH_2CH_2SCH_2CH_3$; $CH_2CH_2N(CH_3)$ $CH_2CH_3$; $CH_2CH_2O(CH_2CH_2O)_nCH_3$, where n is an integer ranging from 2 to 100; and $CH_2CH_2O$—$(CH_2CH_2O)_nCH_2CH_3$, where n is an integer ranging from 2 to 100.

"Heteroalkene" refers to an alkene, where one or more carbon atoms in the alkene is replaced by a heteroatom (e.g., O, S, N-alkyl). Nonlimiting examples of heteroalkenes include: $CH_2CHCH_2OCH_3$; $CH_2CHCH_2SCH_3$; $CH_2CHCH_2N(CH_3)_2$; $CH_2CHCH_2CH_2OCH_3$; $CH_2CH$—$CH_2CH_2SCH_3$; and $CH_2CHCH_2CH_2N(CH_3)_2$.

"Heteroalkenyl" refers to a heteroalkene missing one hydrogen. Nonlimiting examples of heteroalkenes include: $CHCHCH_2OCH_3$; $CHCHCH_2SCH_3$; $CHCHCH_2N(CH_3)_2$; $CHCHCH_2CH_2OCH_3$; $CHCH$—$CH_2CH_2SCH_3$; and $CHCHCH_2CH_2N(CH_3)_2$.

"Heterocycloalkane" refers to a cycloalkane where one or more carbon atoms in the cycloalkane is replaced by a heteroatom (e.g., O, S, N-alkyl). Nonlimiting examples of heterocycloalkanes include: $(CH_2)_4O$; $(CH_2)_4S$; $(CH_2)_4N$—$CH_3$; $(CH_2)_5O$; $(CH_2)_5S$; and $(CH_2)_5N$—$CH_3$.

"Heterocycloalkyl" refers to a heterocycloalkane missing one hydrogen. Nonlimiting examples of heterocycloalkyls include: $CH(CH_2)_3O$; $CH(CH_2)_3S$; $CH(CH_2)_3NCH_3$; $CH(CH_2CH_2)_2O$; $CH(CH_2CH_2)_2S$; and $CH(CH_2CH_2)NCH_3$.

"Heteroaromatic group" refers to an aromatic group where one or more of the carbon atoms has been replaced by a heteroatom (e.g., N). refers to a cyclic or multi-cyclic, planar molecule with a ring of resonance bonds that exhibit more stability than other geometric or connective arrangements with the same set of atoms, wherein the cyclic or multi-cyclic, planar molecule contains a heteroatom (e.g., O, S, N). Nonlimiting examples of heteroaromatic groups include: furanyl; thiophenyl; pyrrolyl; and pyridyl.

"β-Lactamase Tag" refers to the combination of a mutant β-lactamase tag with a fluorophore-derivatized probe. In use, the tag is covalently bound to a target protein. See, for example, Watanabe et al., "Multicolor Protein Labeling in Living Cells Using Mutant β-Lactamase-Tag Technology", *Bioconjug Chem* 2010, 21, 2320-2326.

"Leaving group" refers to a chemical moiety that is capable of being displaced by a nucleophilic compound, typically through an $S_N2$ reaction. Nonlimiting examples of leaving groups include: Cl, Br, I, OAc, methyl sulfate ion, methanesulfonate ion, trifluoromethane-sulfonate ion, and 4-methylbenzenesulfonate ion.

"Linker" refers to a chemical group that connects two parts of a molecule, typically through covalent bonds. A generic example of a linker is: A-linker-B, where "A" and "B" are parts of a molecule, and the bifunctional linker (e.g., linker has functional groups at both termini that are capable of covalently binding to moieties on the molecular parts it connects) is covalently bonded to part "A" on one terminus and part "B" on the other. Nonlimiting examples of linkers include: C(O)-alkyl-NH; C(O)-alkyl-N(alkyl); C(O)-alkyl-O; C(O)-alkyl-S; NH-alkyl-NH; N(alkyl)-alkyl-NH; N(alkyl)-alkyl-N(alkyl); NH-alkyl-O; N(alkyl)-alkyl-O; NH-alkyl-S; N(alkyl)-alkyl-S; $O\text{-}(CH_2CH_2O)_n\text{-}CH_2CH_2OH$, where "n" is an integer ranging from 1 to 100; $O\text{-}(CH_2CH_2O)_n\text{-}CH_2CH_2O\text{-alkyl}$, where "n" is an integer ranging from 1 to 100; $NH\text{-}(CH_2CH_2O)_n\text{-}CH_2CH_2OH$, where "n" is an integer ranging from 1 to 100; and $NH\text{-}(CH_2CH_2O)_n\text{-}CH_2CH_2O\text{-alkyl}$, where "n" is an integer ranging from 1 to 100.

"NHS Ester" refers to an N-hydroxysuccinimide ester. NHS esters are reactive groups formed by carbodiimide-activation of carboxylate molecules. NHS ester-activated crosslinkers and labeling compounds react with primary amines in physiologic to slightly alkaline conditions (pH 7.2 to 9) to yield stable amide bonds. The reaction releases N-hydroxysuccinimide.

"Photoactivated localization microscopy" (PALM) refers to a form of super-resolution microscopy. PALM imaging pin-points individual molecules in a sample and subsequently reconstructs an extremely high resolution image from hundreds of frames. This type of microscopy is capable of nanometer scale resolution through the use of photoswitchable fluorophores. In operation, a low-power activating laser beam randomly converts the fluorophore to an active state; the active state molecules are imaged by a high-power illuminating laser beam to immediately convert them back to an inactive state. The active/inactive conversion is repeated over thousands of frames such that all the fluorophores have been imaged. See, for example, Betzig et al. "Imaging Intracellular Fluorescent Proteins at Nanometer Resolution", *Science* 2006, 313, 1642-1645, which is incorporated-by-reference into this document for all purposes.

"SnapTag" refers to a self-labeling protein tag commercially available in various expression vectors. It is a 182 residue polypeptide that is capable of being fused to a targeted protein and covalently bound to a ligand (e.g., fluorescent dye). See Crivat et al., "Imaging Proteins Inside Cells with Fluorescent Tags", *Trends in Biotechnology* 2012, 30, 8-16, which is incorporated-by-reference into this document for all purposes.

"Substituted alkyl" refers to an alkyl where one or more hydrogen atoms have been replaced with a different substituent. Nonlimiting examples of such substituents include: alkyl; alkenyl; alkynyl; cycloalkyl; cycloalkenyl; heterocycloalkyl; heterocycloalkenyl; aromatic group; heteroaromatic group; OH; O-alkyl; $NH_2$; NH-alkyl; SH; CN; $NO_2$; $CF_3$; C(O)H; C(O)-alkyl; $CO_2H$; $CO_2$-alkyl; $OC(O)CH_3$.

"Substituted alkenyl" refers to an alkenyl where one or more hydrogen atoms have been replaced with a different substituent. Nonlimiting examples of such substituents include: alkyl; alkenyl; alkynyl; cycloalkyl; cycloalkenyl; heterocycloalkyl; heterocycloalkenyl; aromatic group; heteroaromatic group; OH; O-alkyl; $NH_2$; NH-alkyl; SH; CN; $NO_2$; $CF_3$; C(O)H; C(O)-alkyl; $CO_2H$; $CO_2$-alkyl; $OC(O)CH_3$.

"Substituted aromatic group" refers to an aromatic group where one or more hydrogen atoms have been replaced with a different substituent. Nonlimiting examples of such substituents include: alkyl; alkenyl; alkynyl; cycloalkyl; cycloalkenyl; heterocycloalkyl; heterocycloalkenyl; aromatic group; heteroaromatic group; OH; O-alkyl; $NH_2$; NH-alkyl; SH; CN; $NO_2$; $CF_3$; C(O)H; C(O)-alkyl; $CO_2H$; $CO_2$-alkyl; $OC(O)CH_3$.

"Substituted cycloalkenyl" refers to a cycloalkenyl where one or more hydrogen atoms have been replaced with a different substituent. Nonlimiting examples of such substituents include: alkyl; alkenyl; alkynyl; cycloalkyl; cycloalkenyl; heterocycloalkyl; heterocycloalkenyl; aromatic group; heteroaromatic group; OH; O-alkyl; $NH_2$; NH-alkyl; SH; CN; $NO_2$; $CF_3$; C(O)H; C(O)-alkyl; $CO_2H$; $CO_2$-alkyl; $OC(O)CH_3$.

"Substituted cycloalkyl" refers to a cycloalkyl where one or more hydrogen atoms have been replaced with a different substituent. Nonlimiting examples of such substituents include: alkyl; alkenyl; alkynyl; cycloalkyl; cycloalkenyl; heterocycloalkyl; heterocycloalkenyl; aromatic group; heteroaromatic group; OH; O-alkyl; $NH_2$; NH-alkyl; SH; CN; $NO_2$; $CF_3$; C(O)H; C(O)-alkyl; $CO_2H$; $CO_2$-alkyl; $OC(O)CH_3$.

"Substituted heteroalkyl" refers to a heteroalkyl where one or more hydrogen atoms have been replaced with a different substituent. Nonlimiting examples of such substituents include: alkyl; alkenyl; alkynyl; cycloalkyl; cycloalkenyl; heterocycloalkyl; heterocycloalkenyl; aromatic group; heteroaromatic group; OH; O-alkyl; $NH_2$; NH-alkyl; SH; CN; $NO_2$; $CF_3$; C(O)H; C(O)-alkyl; $CO_2H$; $CO_2$-alkyl; $OC(O)CH_3$.

"Substituted heteroalkenyl" refers to a heteroalkenyl where one or more hydrogen atoms have been replaced with a different substituent. Nonlimiting examples of such substituents include: alkyl; alkenyl; alkynyl; cycloalkyl; cycloalkenyl; heterocycloalkyl; heterocycloalkenyl; aromatic group; heteroaromatic group; OH; O-alkyl; $NH_2$; NH-alkyl; SH; CN; $NO_2$; $CF_3$; C(O)H; C(O)-alkyl; $CO_2H$; $CO_2$-alkyl; $OC(O)CH_3$.

"Substituted heteroaromatic group" refers to a heteroaromatic where one or more hydrogen atoms have been replaced with a different substituent. Nonlimiting examples of such substituents include: alkyl; alkenyl; alkynyl; cycloalkyl; cycloalkenyl; heterocycloalkyl; heterocycloalkenyl; aromatic group; heteroaromatic group; OH; O-alkyl; $NH_2$; NH-alkyl; SH; CN; $NO_2$; $CF_3$; C(O)H; C(O)-alkyl; $CO_2H$; $CO_2$-alkyl; $OC(O)CH_3$.

"Substituted heterocycloalkenyl" refers to a heterocycloalkenyl where one or more hydrogen atoms have been replaced with a different substituent. Nonlimiting examples of such substituents include: alkyl; alkenyl; alkynyl; cycloalkyl; cycloalkenyl; heterocycloalkyl; heterocycloalkenyl; aromatic group; heteroaromatic group; OH; O-alkyl; $NH_2$; NH-alkyl; SH; CN; $NO_2$; $CF_3$; C(O)H; C(O)-alkyl; $CO_2H$; $CO_2$-alkyl; $OC(O)CH_3$.

"Substituted heterocycloalkyl" refers to a heterocycloalkyl where one or more hydrogen atoms have been replaced with a different substituent. Nonlimiting examples of such substituents include: alkyl; alkenyl; alkynyl; cycloalkyl; cycloalkenyl; heterocycloalkyl; heterocycloalkenyl; aromatic group; heteroaromatic group; OH; O-alkyl; $NH_2$; NH-alkyl; SH; CN; $NO_2$; $CF_3$; C(O)H; C(O)-alkyl; $CO_2H$; $CO_2$-alkyl; $OC(O)CH_3$.

"Super-resolution microscopy" refers a form of light microscopy that allows images to be taken with a higher resolution than the diffraction limit. See, for example, Neice et al. "Methods and Limitations of Subwavelength Imaging", *Advances in Imaging and Electron Physics* 2010, 163, 117-140, which is incorporated-by-reference into this document for all purposes.

"TMPTag" refers to use of a trimethorprim derivative as a tag to label biomolecules (e.g., proteins). Use of TMPTags is typically carried out as follows: A target protein is tagged with an *E. coli* dihydrofolate reductase cysteine mutant and covalently bound to a cell-permeable acrylamide-trimethoprim-fluorophore. See, for example Miller et al. "In Vivo Protein Labeling with Trimethoprim Conjugates: a Flexible Chemical Tag", *Nat Methods* 2005, 2, 255-257 and Wang et al. "The Covalent Trimethoprim Chemical Tag Facilitates Single Molecule Imaging with Organic Fluorophores", Biophysical Journal 2014, 106, 272-278, both of which are incorporated-by-reference into this document for all purposes.

Figure 1:
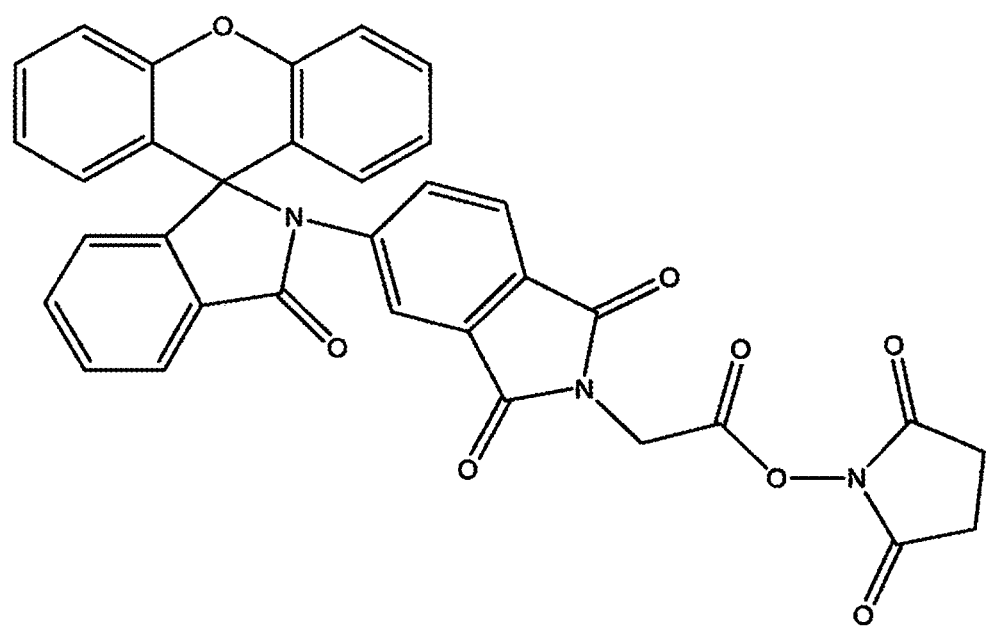
FIG. 1 shows a type of fluorescent compound discussed in Fölling et al. "Fluorescence Nanoscopy with Optical Sectioning by Two-Photon Induced Molecular Switching Using Continuous-Wave Lasers", *Angew. Chem. Int. Ed.* 2007, 46, 6266-6270.
Figure 2:
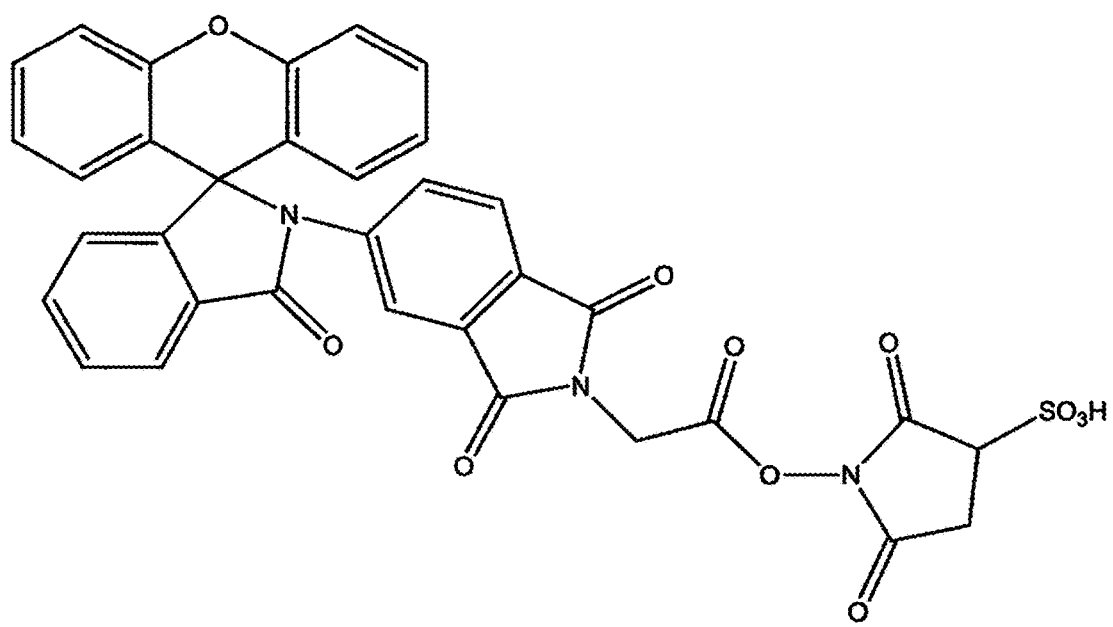
FIG. 2 shows a type of fluorescent compound discussed in Bossi et al. "Multicolor Far-Field Fluorescence Nanoscopy Through Isolated Detection of Distinct Molecular Species", *Nano Lett.* 2008, 8, 2463-2468.
Figure 3:
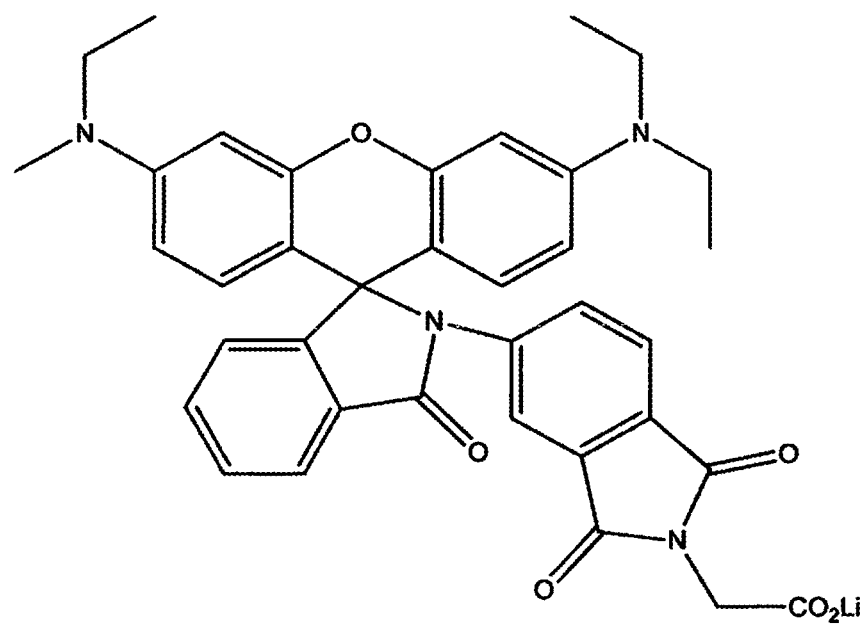
FIG. 3 shows a type of fluorescent compound discussed in Fölling et al. "Fluorescence Nanoscopy with Optical Sectioning by Two-Photon Induced Molecular Switching Using Continuous-Wave Lasers", *ChemPhysChem* 2008, 9, 321-326.
Figure 3:
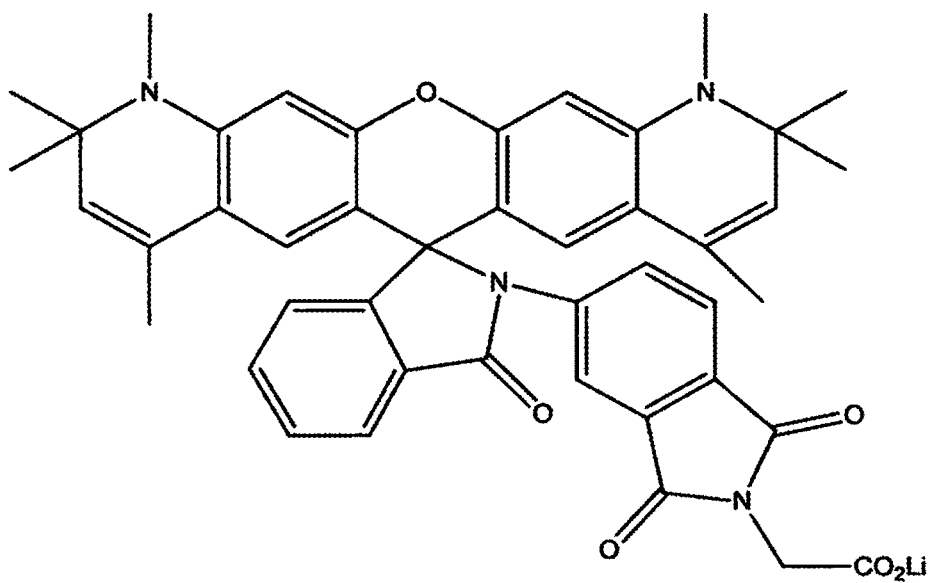
Figure 4:
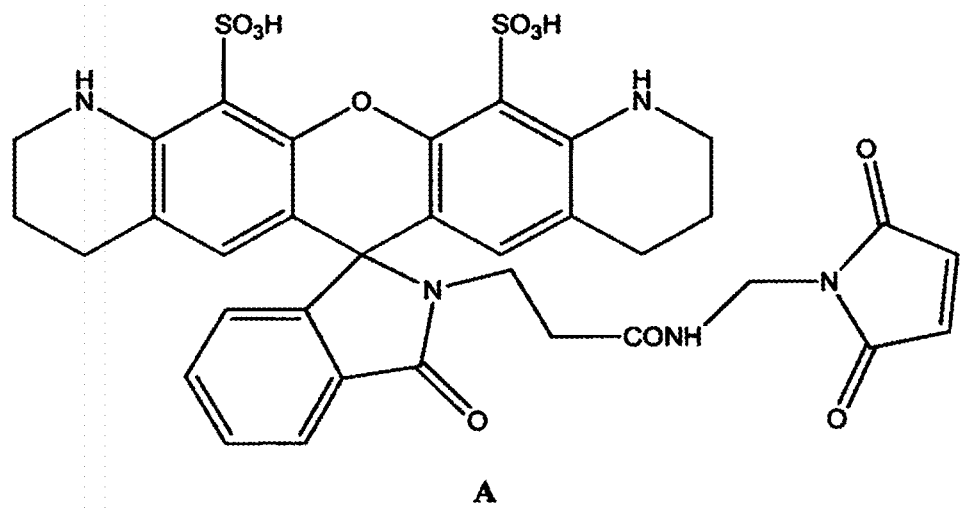
FIG. 4 shows a type of fluorescent compound discussed in Belov et al. "Rhodamine Spiroamides for Multicolor Single-Molecule Switching Fluorescent Nanoscopy", *Chem. Eur. J.* 2009, 15, 10762-10776.
Figure 4:
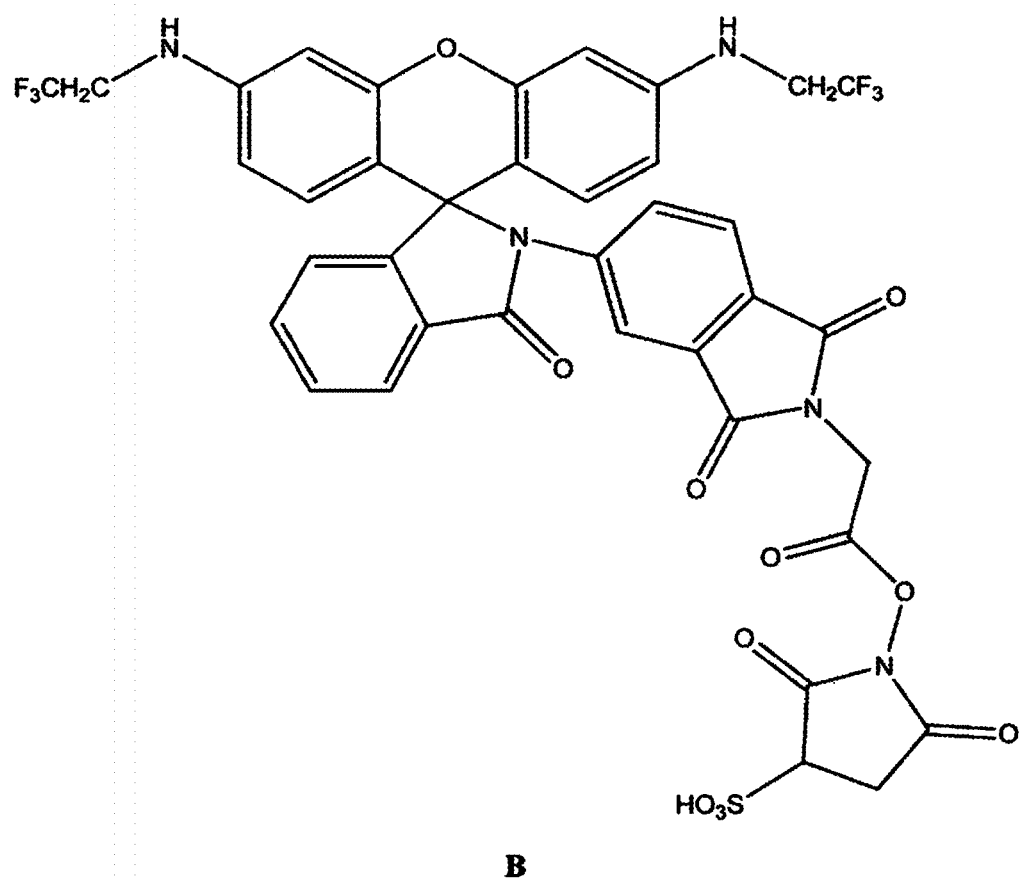
Figure 5:
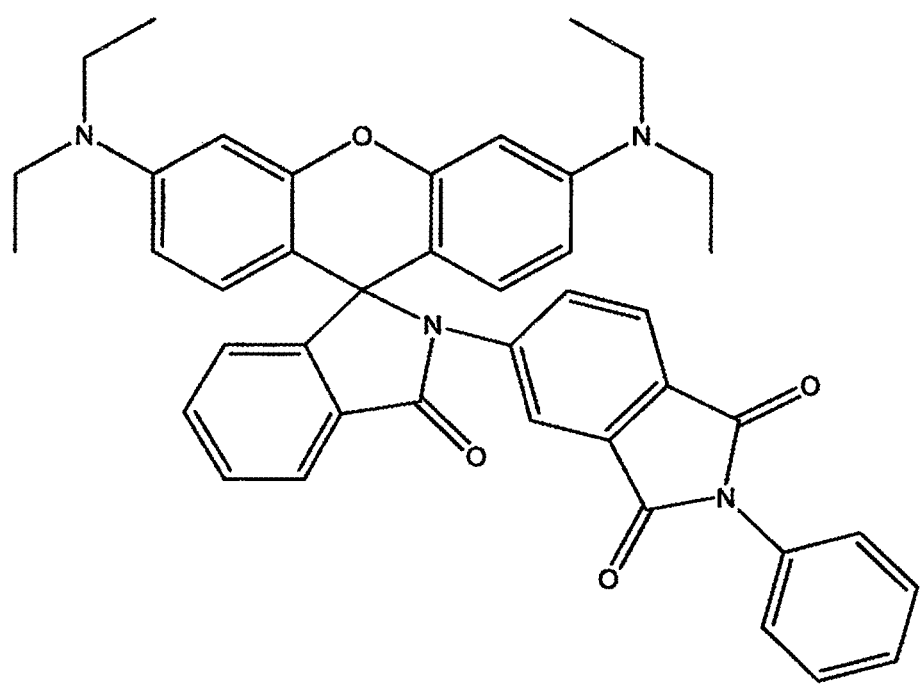
FIG. 5 shows a type of fluorescent compound discussed in Lee et al. "Small-Molecule Labeling of Live Cell Surfaces for Three-Dimensional Super-Resolution Microscopy", *J Am. Chem. Soc.* 2014,136, 14003-14006.
Figure 6:
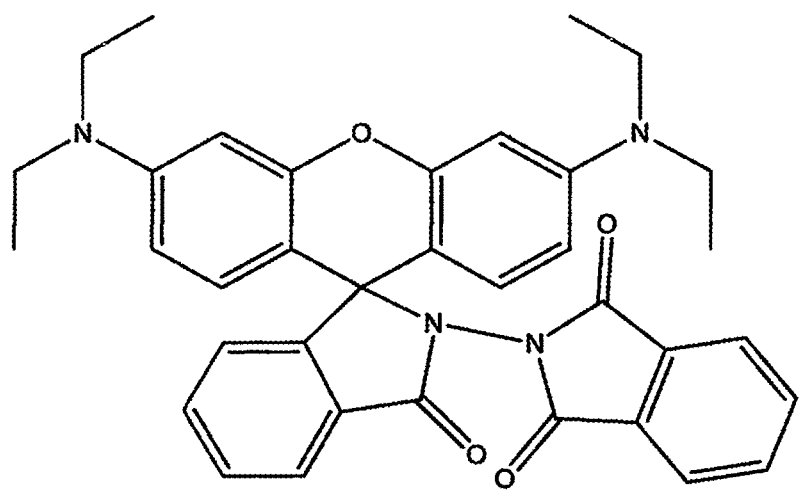
FIG. 6 shows a type of fluorescent compound discussed in Wan et. al. "Cascade Off-On-Off Fluorescent Probe: Duel Detection of Trivalent Ions and Phosphate Ions", *RSC Adv.* 2014, 4, 29479-29484.
Figure 7:
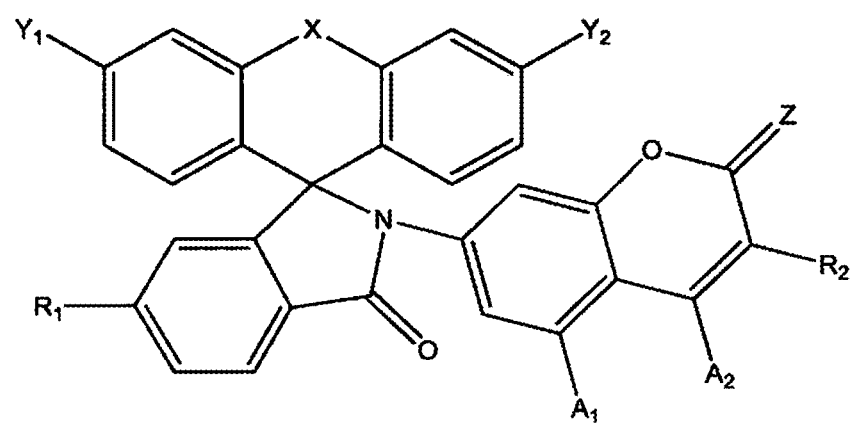
FIG. 7 shows a general structure for compounds according to the present invention.

FIG. 7 shows a general structure for compounds according to the present invention, where the elements X, $Y_1$, $Y_2$, $R_1$, $R_2$, $A_1$, $A_2$ and Z are defined as follows:

X is O, N-alkyl, S, $Si(alkyl)_2$ or $C(alkyl)_2$;
$Y_1$ is O, $N(alkyl)_2$ or one of the moieties shown in FIG. 9 (i.e., a, b, c, or d);
$Y_2$ is O, $N(alkyl)_2$ or one of the moieties shown in FIG. 9 (i.e., a, b, c, or d);
$R_1$ is hydrogen, C(O)NH-Handle, C(O)-linker-Handle, C(O)NH-Acceptor, C(O)-linker-Acceptor, C(O)NH-linker-CH2-X where X is a leaving group, $C(O)NH—(CH_2CH_2)_nC(O)N(H)$-Handle where "n" is an integer ranging from 1 to 100, $C(O)NH—(CHCH)_n$-Acceptor where "n" is an integer ranging from 1 to 100, $C(O)NH—(CH_2CH_2O)_3—C(O)NH—(CH_2CH_2O)_2—(CH2)_6$—Cl, or $C(O)NH—(CH_2CH_2O)_3—C(O)NH—(CH_2CH_2O)_3—C(O)NH—(CH_2CH_2O)_2—(CH_2)_6$—Cl;
$R_2$ is hydrogen, C(O)NH-Handle, C(O)-linker-Handle, C(O)NH-Acceptor, C(O)-linker-Acceptor, C(O)NH-linker-CH2-X where X is a leaving group, $C(O)NH—(CH_2CH_2)_nC(O)N(H)$-Handle where "n" is an integer ranging from 1 to 100, $C(O)NH—(CHCH)_n$-Acceptor where "n" is an integer ranging from 1 to 100, $C(O)NH—(CH_2CH_2O)_3—C(O)NH—(CH_2CH_2O)_2$-$(CH2)_6$-Cl, or $C(O)NH—(CH_2CH_2O)_3—C(O)NH—(CH_2CH_2O)_3—C(O)NH—(CH_2CH_2O)_2—(CH_2)_6$—Cl;

$A_1$ is hydrogen, alkyl, alkenyl, alkynyl, heteroalkyl, heteroalkenyl, cycloalkyl, cycloalkenyl, heterocycloalkyl, heterocycloalkenyl, aromatic, heteroaromatic, substituted alkyl, substituted alkenyl, substituted alkynyl, substituted heteroalkyl, substituted heteroalkenyl, heterocycloalkyl, heterocycloalkenyl, substituted aromatic group, or substituted heteroaromatic group;
$A_2$ is hydrogen, alkyl, alkenyl, alkynyl, heteroalkyl, heteroalkenyl, cycloalkyl, cycloalkenyl, heterocycloalkyl, heterocycloalkenyl, aromatic, heteroaromatic, substituted alkyl, substituted alkenyl, substituted alkynyl, substituted heteroalkyl, substituted heteroalkenyl, heterocycloalkyl, heterocycloalkenyl, substituted aromatic group, or substituted heteroaromatic group;
Z is O, S, Se, Te or an Acceptor.

Figure 8:
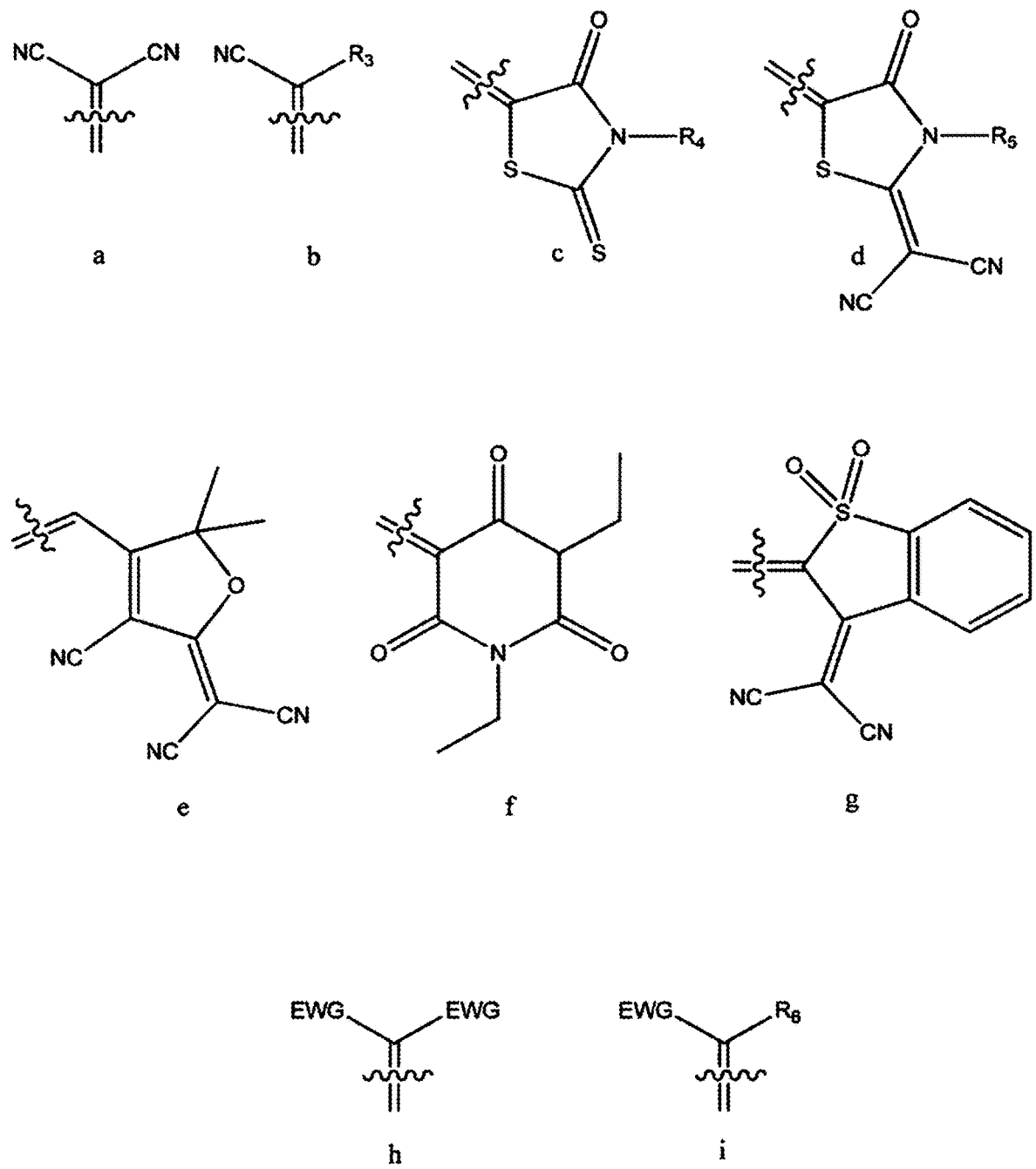
FIG. 8 shows nonlimiting examples of Acceptor moieties included in compounds according to the present invention.

FIG. 8 shows nonlimiting examples of Acceptor moieties included in compounds according to the present invention.

Nonlimiting examples of compounds according to the present invention are (in reference to FIG. 7):

1. X is O; $Y_1$ is one of the moieties shown in FIG. 9 (i.e., a, b, c, or d); $Y_2$ is one of the moieties shown in FIG. 9 (i.e., a, b, c, or d); $R_1$ is hydrogen, C(O)NH-Handle, C(O)-linker-Handle, C(O)NH-Acceptor, C(O)-linker-Acceptor, C(O)NH-linker-CH2-X where X is a leaving group, $C(O)NH—(CH_2CH_2),C(O)N(H)$-Handle where "n" is an integer ranging from 1 to 100, $C(O)NH—(CHCH)_n$-Acceptor where "n" is an integer ranging from 1 to 100, $C(O)NH—(CH_2CH_2O)_3—C(O)NH—(CH_2CH_2O)_2$-$(CH2)_6$-Cl, or $C(O)NH—(CH_2CH_2O)_3—C(O)NH—(CH_2CH_2O)_3—C(O)NH—(CH_2CH_2O)_2—(CH_2)_6$—Cl; $R_2$ is hydrogen, C(O)NH-Handle, C(O)-linker-Handle, C(O)NH-Acceptor, C(O)-linker-Acceptor, C(O)NH-linker-CH2-X where X is a leaving group, $C(O)NH—(CH_2CH_2),C(O)N(H)$-Handle where "n" is an integer ranging from 1 to 100, $C(O)NH—(CHCH)_n$-Acceptor where "n" is an integer ranging from 1 to 100, $C(O)NH—(CH_2CH_2O)_3—C(O)NH—(CH_2CH_2O)_2$-$(CH2)_6$-Cl, or $C(O)NH—(CH_2CH_2O)_3—C(O)NH—(CH_2CH_2O)_3—C(O)NH—(CH_2CH_2O)_2—(CH_2)_6$-Cl; $A_1$ is hydrogen, alkyl or substituted alkyl; $A_2$ is hydrogen, alkyl or substituted alkyl; Z is O.

2. X is O; $Y_1$ is one of the moieties shown in FIG. 9 (i.e., a, b, c, or d); $Y_2$ is one of the moieties shown in FIG. 9 (i.e., a, b, c, or d); $R_1$ is hydrogen, C(O)NH-Handle, C(O)-linker-Handle, C(O)NH-Acceptor, C(O)-linker-Acceptor, C(O)NH-linker-CH2-X where X is a leaving group, $C(O)NH—(CH_2CH_2)_nC(O)N(H)$-Handle where "n" is an integer ranging from 1 to 100, $C(O)NH—(CHCH)_n$-Acceptor where "n" is an integer ranging from 1 to 100, $C(O)NH—(CH_2CH_2O)_3—C(O)NH—(CH_2CH_2O)_2$-$(CH2)_6$-Cl, or $C(O)NH—(CH_2CH_2O)_3—C(O)NH—(CH_2CH_2O)_3—C(O)NH—(CH_2CH_2O)_2—(CH_2)_6$-Cl; $R_2$ is hydrogen, C(O)NH-Handle, C(O)-linker-Handle, C(O)NH-Acceptor, C(O)-linker-Acceptor, C(O)NH-linker-CH2-X where X is a leaving group, $C(O)NH—(CH_2CH_2),C(O)N(H)$-Handle where "n" is an integer ranging from 1 to 100, $C(O)NH—(CHCH)_n$-Acceptor where "n" is an integer ranging from 1 to 100, $C(O)NH—(CH_2CH_2O)_3—C(O)NH—(CH_2CH_2O)_2$-$(CH2)_6$-Cl, or $C(O)NH—(CH_2CH_2O)_3—C(O)NH—(CH_2CH_2O)_3—C(O)NH—

$(CH_2CH_2O)_2$—$(CH_2)_6$-Cl; $A_1$ is hydrogen, alkyl or substituted alkyl; $A_2$ is hydrogen, alkyl or substituted alkyl; Z is S.

3. X is O; $Y_1$ is one of the moieties shown in FIG. 9 (i.e., a, b, c, or d); $Y_2$ is one of the moieties shown in FIG. 9 (i.e., a, b, c, or d); $R_1$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—$(CH_2CH_2)_n$C(O)N(H)-Handle where "n" is an integer ranging from 1 to 100, C(O)NH—$(CHCH)_n$-Acceptor where "n" is an integer ranging from 1 to 100, C(O)NH—$(CH_2CH_2O)_3$—C(O)NH—$(CH_2CH_2O)_2$-(CH2)$_6$-Cl, or C(O)NH—$(CH_2CH_2O)_3$—C(O)NH—$(CH_2CH_2O)_3$—C(O)NH—$(CH_2CH_2O)_2$—$(CH_2)_6$-Cl; $R_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—$(CH_2CH_2)_n$C(O)N(H)-Handle where "n" is an integer ranging from 1 to 100, C(O)NH—$(CHCH)_n$-Acceptor where "n" is an integer ranging from 1 to 100, C(O)NH—$(CH_2CH_2O)_3$—C(O)NH—$(CH_2CH_2O)_2$-(CH2)$_6$-Cl, or C(O)NH—$(CH_2CH_2O)_3$—C(O)NH—$(CH_2CH_2O)_3$—C(O)NH—$(CH_2CH_2O)_2$—$(CH_2)_6$—Cl; $A_1$ is hydrogen, alkyl or substituted alkyl; $A_2$ is hydrogen, alkyl or substituted alkyl; Z is Se.

4. X is O; $Y_1$ is one of the moieties shown in FIG. 9 (i.e., a, b, c, or d); $Y_2$ is one of the moieties shown in FIG. 9 (i.e., a, b, c, or d); $R_1$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—$(CH_2CH_2)_n$C(O)N(H)-Handle where "n" is an integer ranging from 1 to 100, C(O)NH—$(CHCH)_n$-Acceptor where "n" is an integer ranging from 1 to 100, C(O)NH—$(CH_2CH_2O)_3$—C(O)NH—$(CH_2CH_2O)_2$-(CH2)$_6$-Cl, or C(O)NH—$(CH_2CH_2O)_3$—C(O)NH—$(CH_2CH_2O)_3$—C(O)NH—$(CH_2CH_2O)_2$—$(CH_2)_6$-Cl; $R_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—$(CH_2CH_2)_n$C(O)N(H)-Handle where "n" is an integer ranging from 1 to 100, C(O)NH—$(CHCH)_n$-Acceptor where "n" is an integer ranging from 1 to 100, C(O)NH—$(CH_2CH_2O)_3$—C(O)NH—$(CH_2CH_2O)_2$-(CH2)$_6$-Cl, or C(O)NH—$(CH_2CH_2O)_3$—C(O)NH—$(CH_2CH_2O)_3$—C(O)NH—$(CH_2CH_2O)_2$—$(CH_2)_6$—Cl; $A_1$ is hydrogen, alkyl or substituted alkyl; $A_2$ is hydrogen, alkyl or substituted alkyl; Z is Te.

5. X is O; $Y_1$ is one of the moieties shown in FIG. 9 (i.e., a, b, c, or d); $Y_2$ is one of the moieties shown in FIG. 9 (i.e., a, b, c, or d); $R_1$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—$(CH_2CH_2)_n$C(O)N(H)-Handle where "n" is an integer ranging from 1 to 100, C(O)NH—$(CHCH)_n$-Acceptor where "n" is an integer ranging from 1 to 100, C(O)NH—$(CH_2CH_2O)_3$—C(O)NH—$(CH_2CH_2O)_2$-(CH2)$_6$-Cl, or C(O)NH—$(CH_2CH_2O)_3$—C(O)NH—$(CH_2CH_2O)_3$—C(O)NH—$(CH_2CH_2O)_2$—$(CH_2)_6$—Cl; $R_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—$(CH_2CH_2)_n$C(O)N(H)-Handle where "n" is an integer ranging from 1 to 100, C(O)NH—$(CHCH)_n$-Acceptor where "n" is an integer ranging from 1 to 100, C(O)NH—$(CH_2CH_2O)_3$—C(O)NH—$(CH_2CH_2O)_2$-(CH2)$_6$-Cl, or C(O)NH—$(CH_2CH_2O)_3$—C(O)NH—$(CH_2CH_2O)_3$—C(O)NH—$(CH_2CH_2O)_2$—$(CH_2)_6$-Cl; $A_1$ is hydrogen, alkyl or substituted alkyl; $A_2$ is hydrogen, alkyl or substituted alkyl; Z is Acceptor.

6. X is O; $Y_1$ is one of the moieties shown in FIG. 9 (i.e., a, b, c, or d); $Y_2$ is one of the moieties shown in FIG. 9 (i.e., a, b, c, or d); $R_1$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—$(CH_2CH_2)_n$C(O)N(H)-Handle where "n" is an integer ranging from 1 to 100, C(O)NH—$(CHCH)_n$-Acceptor where "n" is an integer ranging from 1 to 100, C(O)NH—$(CH_2CH_2O)_3$—C(O)NH—$(CH_2CH_2O)_2$-(CH2)$_6$-Cl, or C(O)NH—$(CH_2CH_2O)_3$—C(O)NH—$(CH_2CH_2O)_3$—C(O)NH—$(CH_2CH_2O)_2$—$(CH_2)_6$—Cl; $R_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—$(CH_2CH_2)_n$C(O)N(H)-Handle where "n" is an integer ranging from 1 to 100, C(O)NH—$(CHCH)_n$-Acceptor where "n" is an integer ranging from 1 to 100, C(O)NH—$(CH_2CH_2O)_3$—C(O)NH—$(CH_2CH_2O)_2$-(CH2)$_6$-Cl, or C(O)NH—$(CH_2CH_2O)_3$—C(O)NH—$(CH_2CH_2O)_3$—C(O)NH—$(CH_2CH_2O)_2$—$(CH_2)_6$—Cl; $A_1$ is hydrogen, alkyl or substituted alkyl; $A_2$ is hydrogen, alkyl or substituted alkyl; Z is Acceptor "a" shown in FIG. 8.

7. X is O; $Y_1$ is one of the moieties shown in FIG. 9 (i.e., a, b, c, or d); $Y_2$ is one of the moieties shown in FIG. 9 (i.e., a, b, c, or d); $R_1$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—$(CH_2CH_2)_n$C(O)N(H)-Handle where "n" is an integer ranging from 1 to 100, C(O)NH—$(CHCH)_n$-Acceptor where "n" is an integer ranging from 1 to 100, C(O)NH—$(CH_2CH_2O)_3$—C(O)NH—$(CH_2CH_2O)_2$-(CH2)$_6$-Cl, or C(O)NH—$(CH_2CH_2O)_3$—C(O)NH—$(CH_2CH_2O)_3$—C(O)NH—$(CH_2CH_2O)_2$—$(CH_2)_6$—Cl; $R_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—$(CH_2CH_2)_n$C(O)N(H)-Handle where "n" is an integer ranging from 1 to 100, C(O)NH—$(CHCH)_n$-Acceptor where "n" is an integer ranging from 1 to 100, C(O)NH—$(CH_2CH_2O)_3$—C(O)NH—$(CH_2CH_2O)_2$-(CH2)$_6$-Cl, or C(O)NH—$(CH_2CH_2O)_3$—C(O)NH—$(CH_2CH_2O)_3$—C(O)NH—$(CH_2CH_2O)_2$—$(CH_2)_6$—Cl; $A_1$ is hydrogen, alkyl or substituted alkyl; $A_2$ is hydrogen, alkyl or substituted alkyl; Z is Acceptor "b" shown in FIG. 8.

8. X is O; $Y_1$ is one of the moieties shown in FIG. 9 (i.e., a, b, c, or d); $Y_2$ is one of the moieties shown in FIG. 9 (i.e., a, b, c, or d); $R_1$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—$(CH_2CH_2)_n$C(O)N(H)-Handle where "n" is an integer ranging from 1 to 100, C(O)NH—$(CHCH)_n$-Acceptor where "n" is an integer ranging from 1 to 100, C(O)NH—$(CH_2CH_2O)_3$—C(O)NH—$(CH_2CH_2O)_2$-(CH2)$_6$-Cl, or C(O)NH—$(CH_2CH_2O)_3$—C(O)NH—$(CH_2CH_2O)_3$—C(O)NH—$(CH_2CH_2O)_2$—$(CH_2)_6$—Cl; $R_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—$(CH_2CH_2)_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl; A$_1$ is hydrogen, alkyl or substituted alkyl; A$_2$ is hydrogen, alkyl or substituted alkyl; Z is Acceptor "c" shown in FIG. 8.

9. X is O; Y$_1$ is one of the moieties shown in FIG. 9 (i.e., a, b, c, or d); Y$_2$ is one of the moieties shown in FIG. 9 (i.e., a, b, c, or d); R$_1$ is hydrogen, C(O)NH-Handle, C(O)-linker-Handle, C(O)NH-Acceptor, C(O)-linker-Acceptor, C(O)NH-linker-CH2-X where X is a leaving group, C(O)NH-(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl; R$_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl; A$_1$ is hydrogen, alkyl or substituted alkyl; A$_2$ is hydrogen, alkyl or substituted alkyl; Z is Acceptor "d" shown in FIG. 8.

10. X is O; Y$_1$ is one of the moieties shown in FIG. 9 (i.e., a, b, c, or d); Y$_2$ is one of the moieties shown in FIG. 9 (i.e., a, b, c, or d); R$_1$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl; R$_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$-Cl; A$_1$ is hydrogen, alkyl or substituted alkyl; A$_2$ is hydrogen, alkyl or substituted alkyl; Z is Acceptor "e" shown in FIG. 8.

11. X is O; Y$_1$ is one of the moieties shown in FIG. 9 (i.e., a, b, c, or d); Y$_2$ is one of the moieties shown in FIG. 9 (i.e., a, b, c, or d); R$_1$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl; R$_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$).C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$-Cl; A$_1$ is hydrogen, alkyl or substituted alkyl; A$_2$ is hydrogen, alkyl or substituted alkyl; Z is Acceptor "f" shown in FIG. 8.

12. X is O; Y$_1$ is one of the moieties shown in FIG. 9 (i.e., a, b, c, or d); Y$_2$ is one of the moieties shown in FIG. 9 (i.e., a, b, c, or d); R$_1$ is hydrogen, C(O)NH-Handle, C(O)-linker-Handle, C(O)NH-Acceptor, C(O)-linker-Acceptor, C(O)NH-linker-CH2-X where X is a leaving group, C(O)NH-(CH$_2$CH$_2$),C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$-Cl; R$_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$-Cl; A$_1$ is hydrogen, alkyl or substituted alkyl; A$_2$ is hydrogen, alkyl or substituted alkyl; Z is Acceptor "g" shown in FIG. 8.

13. X is O; Y$_1$ is one of the moieties shown in FIG. 9 (i.e., a, b, c, or d); Y$_2$ is one of the moieties shown in FIG. 9 (i.e., a, b, c, or d); R$_1$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$-Cl; R$_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$-Cl; A$_1$ is hydrogen, alkyl or substituted alkyl; A$_2$ is hydrogen, alkyl or substituted alkyl; Z is Acceptor "h" shown in FIG. 8.

14. X is O; Y$_1$ is one of the moieties shown in FIG. 9 (i.e., a, b, c, or d); Y$_2$ is one of the moieties shown in FIG. 9 (i.e., a, b, c, or d); R$_1$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$),C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl; R$_2$ is hydrogen, C(O)NH- Handle, C(O)-linker-Handle, C(O)NH-Acceptor, C(O)-linker-Acceptor, C(O)NH-linker-CH2-X where X is a leaving group, C(O)NH—($CH_2CH_2$)$_n$C(O)N(H)-Handle where "n" is an integer ranging from 1 to 100, C(O)NH—(CHCH)$_n$-Acceptor where "n" is an integer ranging from 1 to 100, C(O)NH—($CH_2CH_2O$)$_3$—C(O)NH—($CH_2CH_2O$)$_2$-($CH2$)$_6$-Cl, or C(O)NH—($CH_2CH_2O$)$_3$—C(O)NH—($CH_2CH_2O$)$_3$—C(O)NH—($CH_2CH_2O$)$_2$—($CH_2$)$_6$—Cl; $A_1$ is hydrogen, alkyl or substituted alkyl; $A_2$ is hydrogen, alkyl or substituted alkyl; Z is Acceptor "i" shown in FIG. 8.

FIGS. 10-13 show examples of structures of compounds according to the present invention, where "n" is 1, 2, 3 or 4 and "HT" is ($CH_2CH_2O$)$_2$—($CH_2$)$_6$—Cl or ($CH_2CH_2O$)$_3$—C(O)NH—($CH_2CH_2O$)$_2$—($CH_2$)$_6$—Cl.

Figure 9:
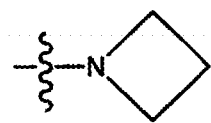
FIG. 9 shows four different moieties that can, individually, be elements $Y_1$ and/or $Y_2$ in the structure of FIG. 7.
Figure 9:
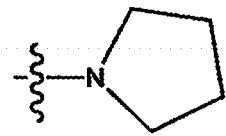
Figure 9:
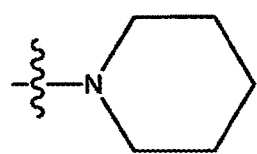
Figure 9:
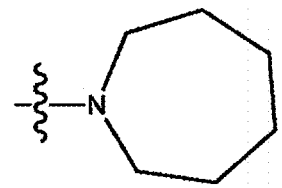
Figure 10:
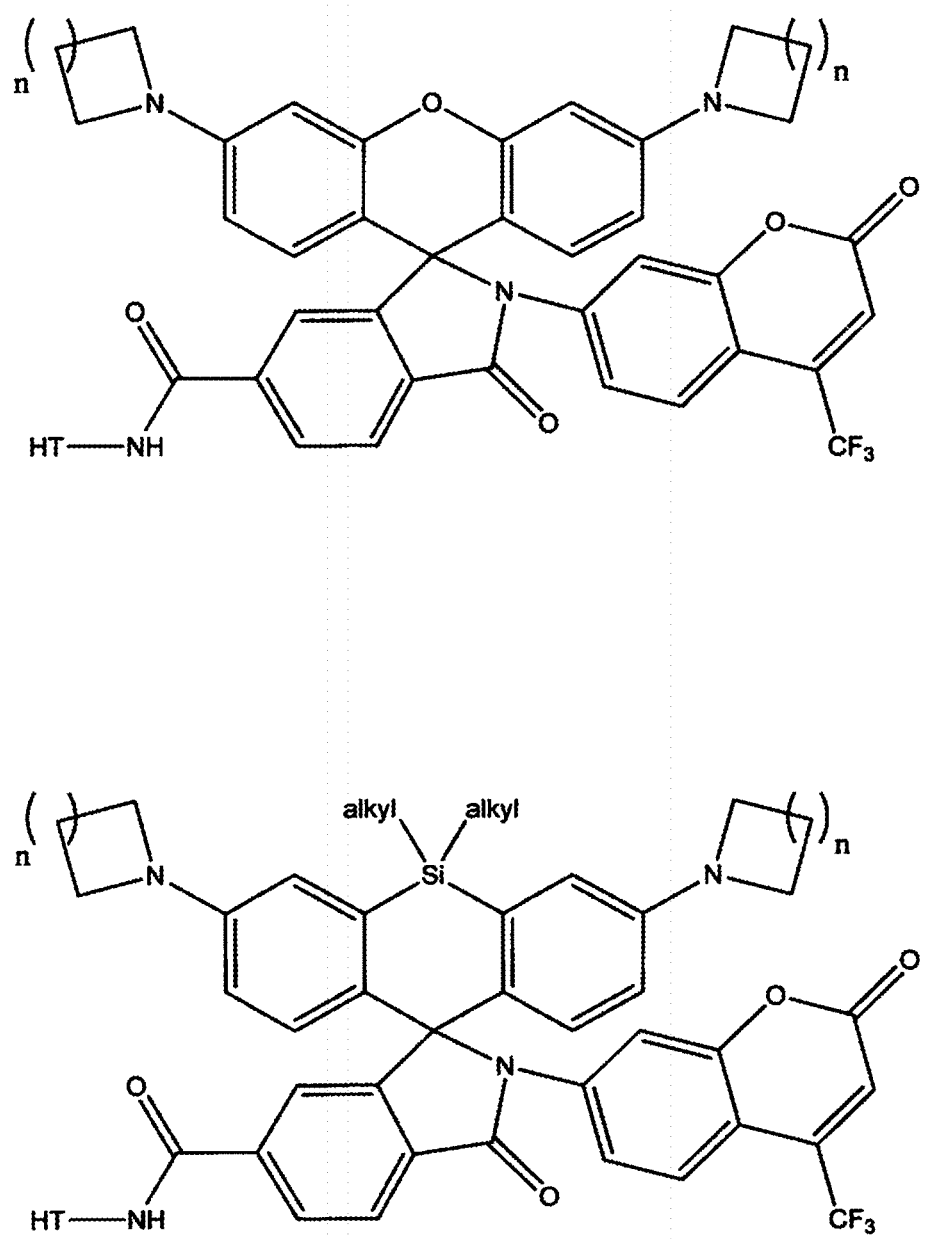
FIGS. 10-13 show examples of structures of compounds according to the present invention.
Figure 11:
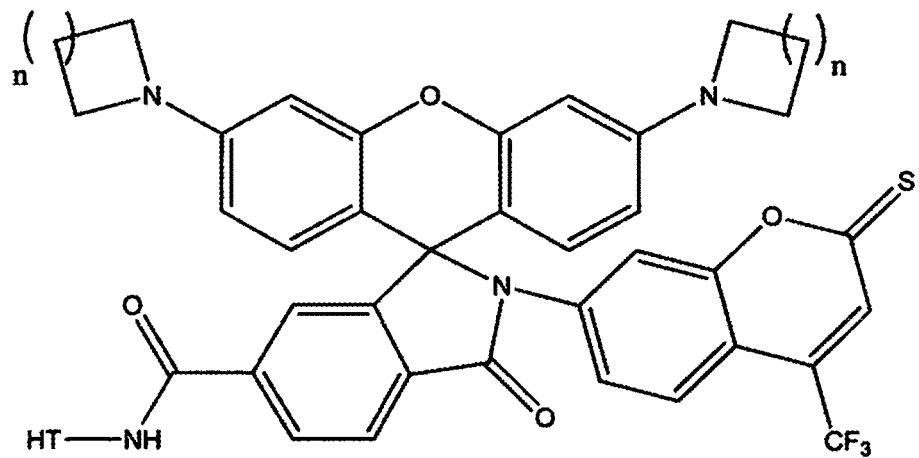
Figure 11:
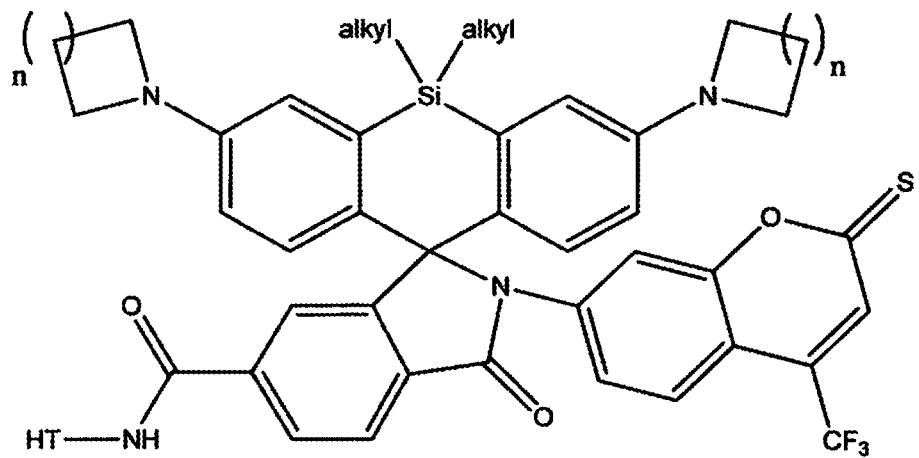
Figure 12:
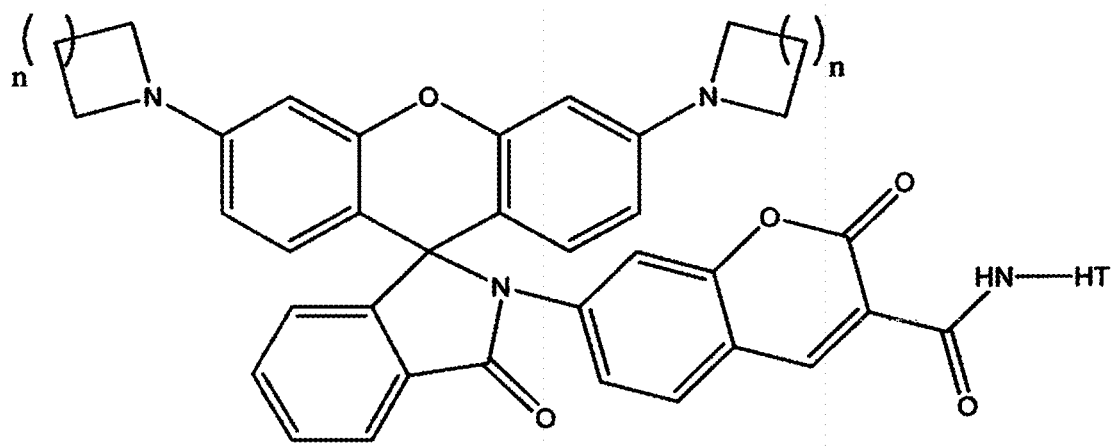
Figure 12:
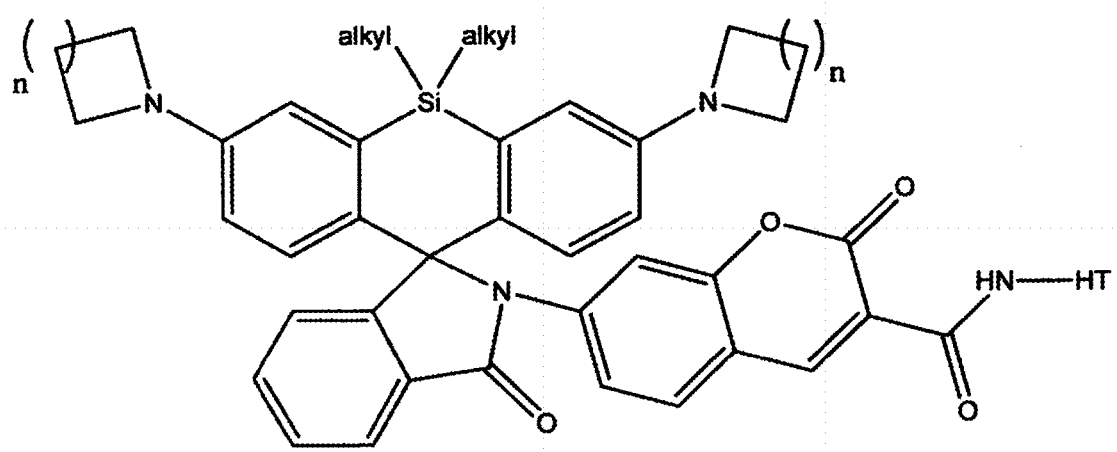
Figure 13:
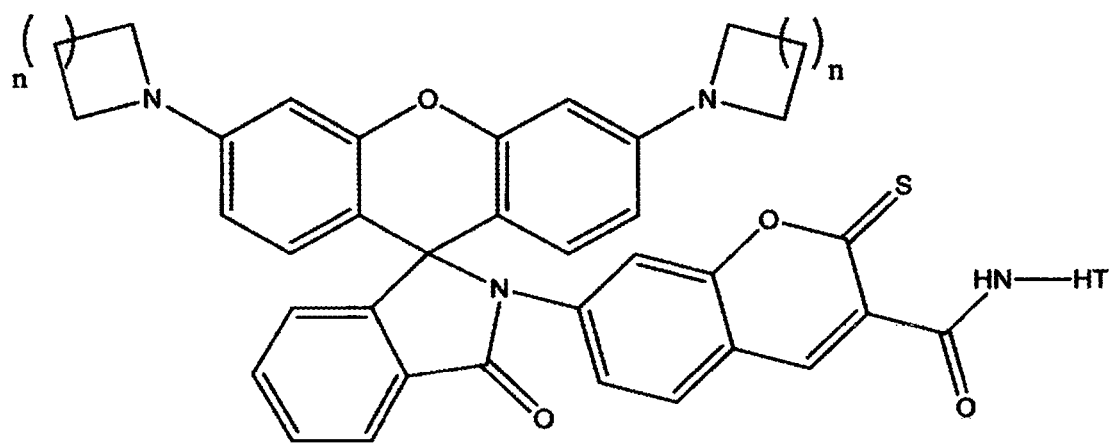
Figure 13:
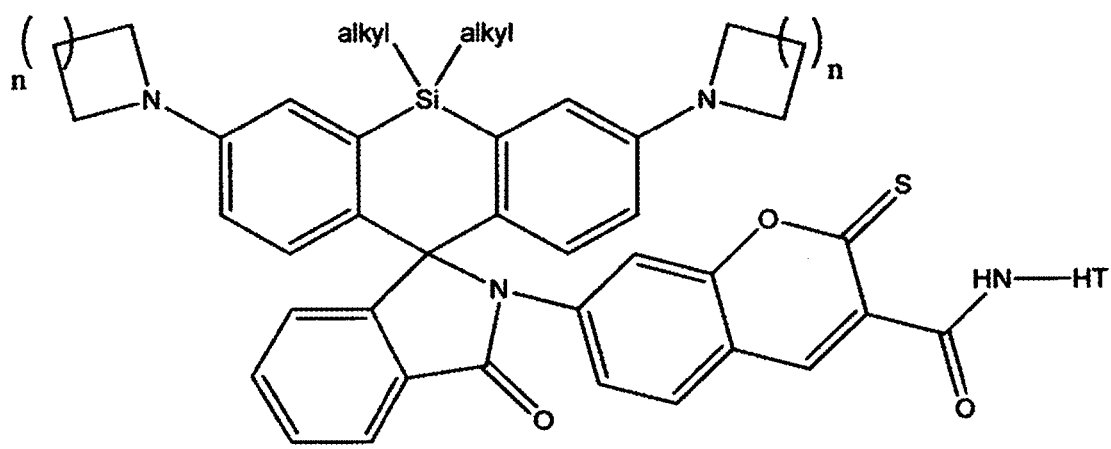

FIG. 18A shows a general structure for compounds according to the present invention, where the elements X, $Y_1$, $Y_2$, and $R_1$ are defined as follows:

X is O, N-alkyl, S, Si(alkyl)$_2$ or C(alkyl)$_2$;

$Y_1$ is O, N(alkyl)$_2$ or one of the moieties shown in FIG. 9 (i.e., a, b, c, or d);

$Y_2$ is O, N(alkyl)$_2$ or one of the moieties shown in FIG. 9 (i.e., a, b, c, or d);

$R_1$ is hydrogen, C(O)NH-Handle, C(O)-linker-Handle, C(O)NH-Acceptor, C(O)-linker-Acceptor, C(O)NH-linker-$CH_2$-X where X is a leaving group, C(O)NH—($CH_2CH_2$)$_n$C(O)N(H)-Handle where "n" is an integer ranging from 1 to 100, C(O)NH—(CHCH)$_n$-Acceptor where "n" is an integer ranging from 1 to 100, C(O)NH—($CH_2CH_2O$)$_3$—C(O)NH—($CH_2CH_2O$)$_2$—($CH2$)$_6$-Cl, or C(O)NH—($CH_2CH_2O$)$_3$—C(O)NH—($CH_2CH_2O$)$_3$—C(O)NH—($CH_2CH_2O$)$_2$—($CH_2$)$_6$—Cl.

Nonlimiting examples of compounds according to the present invention are (in reference to FIG. 18A):

1. X is O, $Y_1$ is O, $Y_2$ is O, $R_1$ is hydrogen, C(O)NH-Handle, C(O)-linker-Handle, C(O)NH-Acceptor, C(O)-linker-Acceptor, or C(O)NH-linker-CH2-X where X is a leaving group.
2. X is O, $Y_1$ is N(alkyl)$_2$, $Y_2$ is N(alkyl)$_2$, $R_1$ is hydrogen, C(O)NH-Handle, C(O)-linker-Handle, C(O)NH-Acceptor, C(O)-linker-Acceptor, or C(O)NH-linker-$CH_2$-X where X is a leaving group.
3. X is O, $Y_1$ is moiety "a" in FIG. 9, $Y_2$ is moiety "a" in FIG. 9, $R_1$ is hydrogen, C(O)NH-Handle, C(O)-linker-Handle, C(O)NH-Acceptor, C(O)-linker-Acceptor, or C(O)NH-linker-$CH_2$-X where X is a leaving group.

FIG. 18B shows a general structure for compounds according to the present invention, where the elements X, $R_{10}$-$R_{19}$, $A_1$, $A_2$ and Z are defined as follows:

X is O, N-alkyl, S, Si(alkyl)$_2$ or C(alkyl)$_2$;

$R_{10}$ and $R_{17}$ are independently selected from —H, alkyl (e.g., methyl, ethyl, propyl, butyl, etc.), —$CH_2$—$SO_3H$, —$CH_2CH_2$—$SO_3H$, —$CH_2OCH_2$—$SO_3H$, —$CH_2CH_2OCH_2CH_2$—$SO_3H$, —$CH_2$—$CO_2H$, —$CH_2$—$CH_2$—$CO_2H$, —$CH_2OCH_2$—$CO_2H$, —$CH_2CH_2OCH_2CH_2$—$CO_2H$;

$R_{11}$, $R_{12}$, $R_{15}$ and $R_{16}$ are independently selected from H, alkyl (e.g., methyl, ethyl, propyl, butyl, etc.), —$CH_2$—$SO_3H$, —$CH_2CH_2$—$SO_3H$, —$CH_2OCH_2$—$SO_3H$, —$CH_2CH_2OCH_2CH_2$—$SO_3H$, —$CH_2$—$CO_2H$, —$CH_2$—$CH_2$—$CO_2H$, —$CH_2OCH_2$—$CO_2H$, —$CH_2CH_2OCH_2CH_2$—$CO_2H$;

$R_{13}$ and $R_{14}$ are independently selected from alkyl (e.g., methyl, ethyl, propyl, butyl, etc.), —C(O)$CH_3$, —C(O)$CH_2CH_3$, —C(O)O$CH_3$, —C(O)O$CH_2CH_3$, —C(O)N($CH_3$)$_2$, —C(O)N($CH_2CH_3$)$_2$;

$R_{18}$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—($CH_2CH_2$)$_n$C(O)N(H)-Handle where "n" is an integer ranging from 1 to 100, C(O)NH—(CHCH)$_n$-Acceptor where "n" is an integer ranging from 1 to 100, C(O)NH—($CH_2CH_2O$)$_3$—C(O)NH—($CH_2CH_2O$)$_2$-($CH2$)$_6$-Cl, or C(O)NH—($CH_2CH_2O$)$_3$—C(O)NH—($CH_2CH_2O$)$_3$—C(O)NH—($CH_2CH_2O$)$_2$—($CH_2$)$_6$—Cl;

$R_{19}$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—($CH_2CH_2$)$_n$C(O)N(H)-Handle where "n" is an integer ranging from 1 to 100, C(O)NH—(CHCH)$_n$-Acceptor where "n" is an integer ranging from 1 to 100, C(O)NH—($CH_2CH_2O$)$_3$—C(O)NH—($CH_2CH_2O$)$_2$-($CH2$)$_6$-Cl, or C(O)NH—($CH_2CH_2O$)$_3$—C(O)NH—($CH_2CH_2O$)$_3$—C(O)NH—($CH_2CH_2O$)$_2$—($CH_2$)$_6$—Cl;

$A_1$ is hydrogen, alkyl, alkenyl, alkynyl, heteroalkyl, heteroalkenyl, cycloalkyl, cycloalkenyl, heterocycloalkyl, heterocycloalkenyl, aromatic, heteroaromatic, substituted alkyl, substituted alkenyl, substituted alkynyl, substituted heteroalkyl, substituted heteroalkenyl, heterocycloalkyl, heterocycloalkenyl, substituted aromatic group, or substituted heteroaromatic group;

$A_2$ is hydrogen, alkyl, alkenyl, alkynyl, heteroalkyl, heteroalkenyl, cycloalkyl, cycloalkenyl, heterocycloalkyl, heterocycloalkenyl, aromatic, heteroaromatic, substituted alkyl, substituted alkenyl, substituted alkynyl, substituted heteroalkyl, substituted heteroalkenyl, heterocycloalkyl, heterocycloalkenyl, substituted aromatic group, or substituted heteroaromatic group;

Z is O, S, Se, Te or an Acceptor.

Nonlimiting examples of compounds according to the present invention are (in reference to FIG. 18B):

1. X is O; $R_{10}$ and $R_{17}$ are independently selected from —H, methyl, and —$CH_2$—$SO_3H$; $R_{11}$, $R_{12}$, $R_{15}$ and $R_{16}$ are independently selected from H and methyl; $R_{13}$ and $R_{14}$ are independently selected from methyl, ethyl, and —C(O)$CH_3$; $R_{18}$ is hydrogen, C(O)NH-Handle, C(O)-linker-Handle, C(O)NH-Acceptor, C(O)-linker-Acceptor, or C(O)NH-linker-CH2-X where X is a leaving group; $R_{19}$ is hydrogen, C(O)NH-Handle, C(O)-linker-Handle, C(O)NH-Acceptor, C(O)-linker-Acceptor, or C(O)NH-linker-CH2-X where X is a leaving group; $A_1$ is hydrogen, alkyl or substituted alkyl; $A_2$ is hydrogen, alkyl or substituted alkyl; Z is O.
2. X is O; $R_{10}$ and $R_{17}$ are independently selected from —$CH_2$—$SO_3H$; $R_{11}$, $R_{12}$, $R_{15}$ and $R_{16}$ are methyl; $R_{13}$ and $R_{14}$ are methyl; $R_{18}$ is hydrogen, C(O)NH-Handle, C(O)-linker-Handle, C(O)NH-Acceptor, C(O)-linker-Acceptor, or C(O)NH-linker-$CH_2$-X where X is a leaving group; $R_{19}$ is hydrogen, C(O)NH-Handle, C(O)-linker-Handle, C(O)NH-Acceptor, C(O)-linker-Acceptor, or C(O)NH-linker-$CH_2$-X where X is a leaving group; $A_1$ is hydrogen, alkyl or substituted alkyl; $A_2$ is hydrogen, alkyl or substituted alkyl; Z is O.

Figure 19:
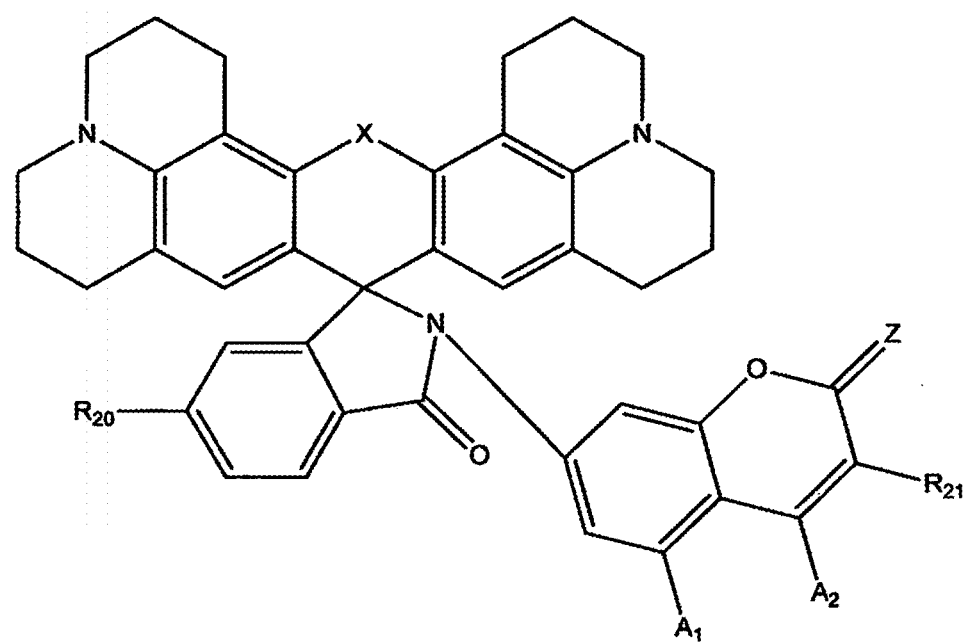

FIG. 19 shows a general structure for compounds according to the present invention, where the elements X, $R_{20}$, $R_{21}$, $A_1$, $A_2$ and Z are defined as follows:

X is O, N-alkyl, S, Si(alkyl)$_2$ or C(alkyl)$_2$;

$R_{20}$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—($CH_2CH_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$-Cl;

R$_{21}$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl;

A$_1$ is hydrogen, alkyl, alkenyl, alkynyl, heteroalkyl, heteroalkenyl, cycloalkyl, cycloalkenyl, heterocycloalkyl, heterocycloalkenyl, aromatic, heteroaromatic, substituted alkyl, substituted alkenyl, substituted alkynyl, substituted heteroalkyl, substituted heteroalkenyl, heterocycloalkyl, heterocycloalkenyl, substituted aromatic group, or substituted heteroaromatic group;

A$_2$ is hydrogen, alkyl, alkenyl, alkynyl, heteroalkyl, heteroalkenyl, cycloalkyl, cycloalkenyl, heterocycloalkyl, heterocycloalkenyl, aromatic, heteroaromatic, substituted alkyl, substituted alkenyl, substituted alkynyl, substituted heteroalkyl, substituted heteroalkenyl, heterocycloalkyl, heterocycloalkenyl, substituted aromatic group, or substituted heteroaromatic group;

Z is O, S, Se, Te or an Acceptor.

Nonlimiting examples of compounds according to the present invention are (in reference to FIG. 19):

1. X is O; R$_{20}$ is hydrogen, C(O)NH-Handle, C(O)-linker-Handle, C(O)NH-Acceptor, C(O)-linker-Acceptor, or C(O)NH-linker-CH$_2$-X where X is a leaving group; R$_{21}$ is hydrogen, C(O)NH-Handle, C(O)-linker-Handle, C(O)NH-Acceptor, C(O)-linker-Acceptor, or C(O)NH-linker-CH$_2$-X where X is a leaving group; A$_1$ is hydrogen, alkyl or substituted alkyl; A$_2$ is hydrogen, alkyl or substituted alkyl; Z is O.

2. X is O; R$_{20}$ is hydrogen, C(O)NH-Handle, C(O)-linker-Handle, C(O)NH-Acceptor, C(O)-linker-Acceptor, or C(O)NH-linker-CH$_2$-X where X is a leaving group; R$_{21}$ is hydrogen, C(O)NH-Handle, C(O)-linker-Handle, C(O)NH-Acceptor, C(O)-linker-Acceptor, or C(O)NH-linker-CH$_2$-X where X is a leaving group; A$_1$ is hydrogen or alkyl; A$_2$ is hydrogen or alkyl; Z is O.

FIG. 20A shows a general structure for compounds according to the present invention, where the elements, where the elements X, Y$_1$, Y$_2$, R$_1$, R$_2$, R$_3$, R$_4$, R$_5$, R$_6$, A$_1$ and A$_2$ are defined as follows:

X is O, N-alkyl, S, Si(alkyl)$_2$ or C(alkyl)$_2$;

Y$_1$ is O, OH, NH$_2$, N(alkyl)$_2$ or one of the moieties shown in FIG. 9 (i.e., a, b, c, or d);

Y$_2$ is O, OH, NH$_2$, N(alkyl)$_2$ or one of the moieties shown in FIG. 9 (i.e., a, b, c, or d);

R$_1$ (which can be a substitution at either the 5' position, the 6' position or both) is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl;

R$_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl;

R$_3$, R$_4$, R$_5$ and R$_6$ are independently hydrogen, alkyl, —SO$_3$H, halogen, or R$_3$ and Y$_1$ can form a ring, or R$_4$ and Y$_1$ can form a ring, or R$_5$ and Y$_2$ can form a ring, or R$_6$ and Y$_2$ can form a ring;

A$_1$ is hydrogen, alkyl, alkenyl, alkynyl, heteroalkyl, heteroalkenyl, cycloalkyl, cycloalkenyl, heterocycloalkyl, heterocycloalkenyl, aromatic, heteroaromatic, substituted alkyl, substituted alkenyl, substituted alkynyl, substituted heteroalkyl, substituted heteroalkenyl, heterocycloalkyl, heterocycloalkenyl, substituted aromatic group, or substituted heteroaromatic group;

A$_2$ is hydrogen, alkyl, alkenyl, alkynyl, heteroalkyl, heteroalkenyl, cycloalkyl, cycloalkenyl, heterocycloalkyl, heterocycloalkenyl, aromatic, heteroaromatic, substituted alkyl, substituted alkenyl, substituted alkynyl, substituted heteroalkyl, substituted heteroalkenyl, heterocycloalkyl, heterocycloalkenyl, substituted aromatic group, or substituted heteroaromatic group.

FIG. 20B shows a general structure for compounds according to the present invention, where the elements R$_1$ and R$_2$ are defined as follows:

R$_1$ (which can be a substitution at either the 5' position, the 6' position or both) is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl;

R$_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl;

FIG. 20C shows a general structure for compounds according to the present invention, where the elements R$_1$ and R$_2$ are defined as follows:

R$_1$ (which can be a substitution at either the 5' position, the 6' position or both) is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl;

R$_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl;

Any suitable synthetic method and/or scheme can be used to synthesize compounds according to the present invention. General synthetic methods for the synthesis of rhodamine dyes and derivatives are presented in Beija et. al. "Synthesis and Applications of Rhodamine Derivatives as Fluorescent Probes", *Chem Soc Rev* 2009, 38, 2410-2433, which is incorporated-by-reference into this document for all purposes. General synthetic methods for the synthesis of coumarin units are presented in Vekariva et al. "Recent Advances in the Synthesis of Coumarin Derivatives via Knoevenagel Condensation: A Review", *Syn Comm* 2014, 44, 2756-2788, which is incorporated-by-reference into this document for all purposes. Various tagging methods are discussed above including references related to synthesizing and using the tags. Synthetic schemes are shown, for example, in FIGS. 15-17 and 21-27.

Figure 14:
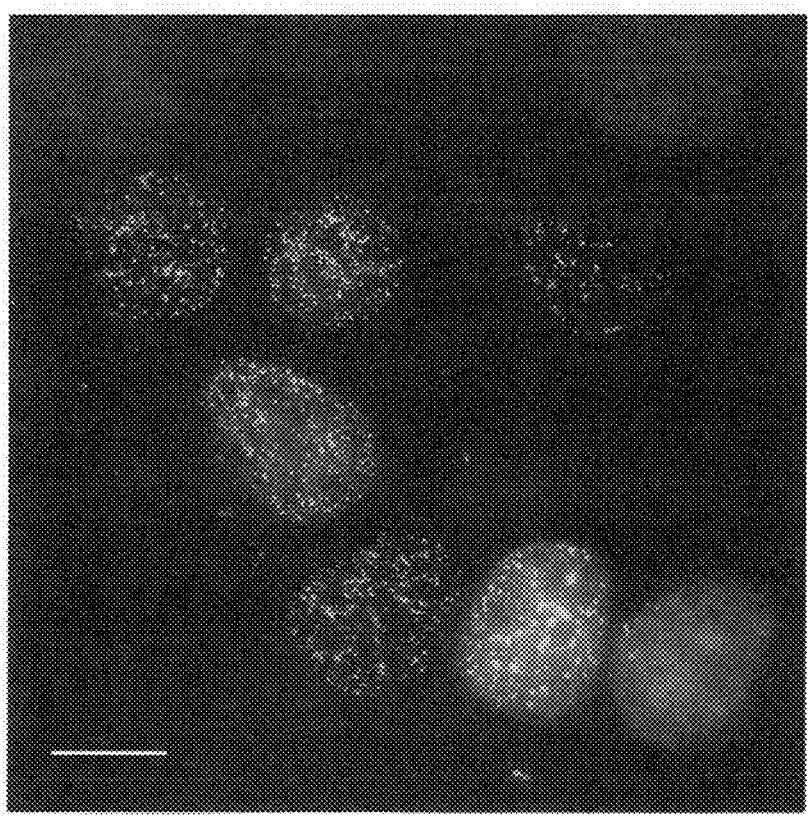
FIG. 14 shows a super-resolution image of a nucleus using PALM and a compound according to the present invention.
Figure 15:
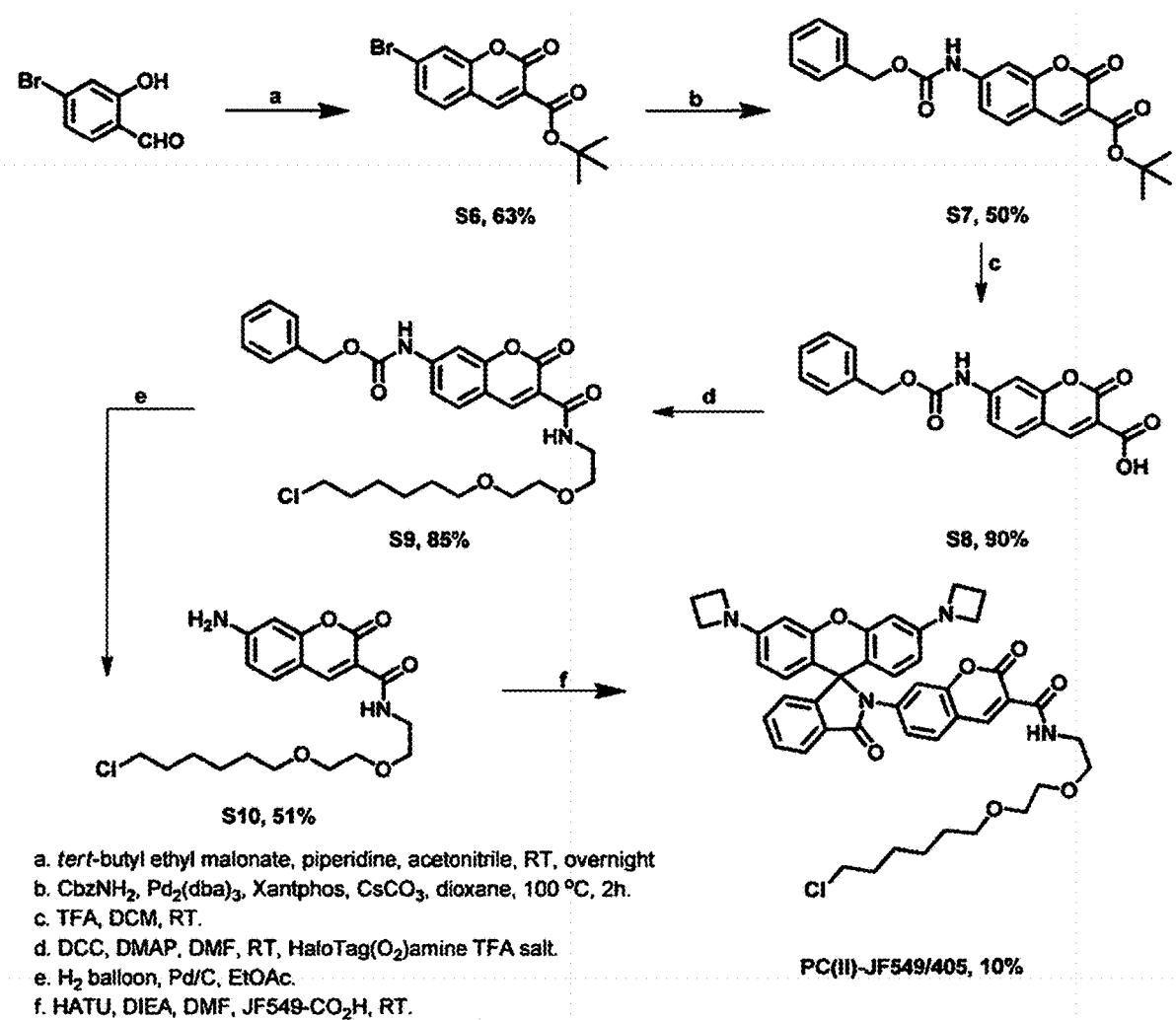
FIGS. 15-17 show schemes for the synthesis of compounds according to the present invention.
Figure 16:
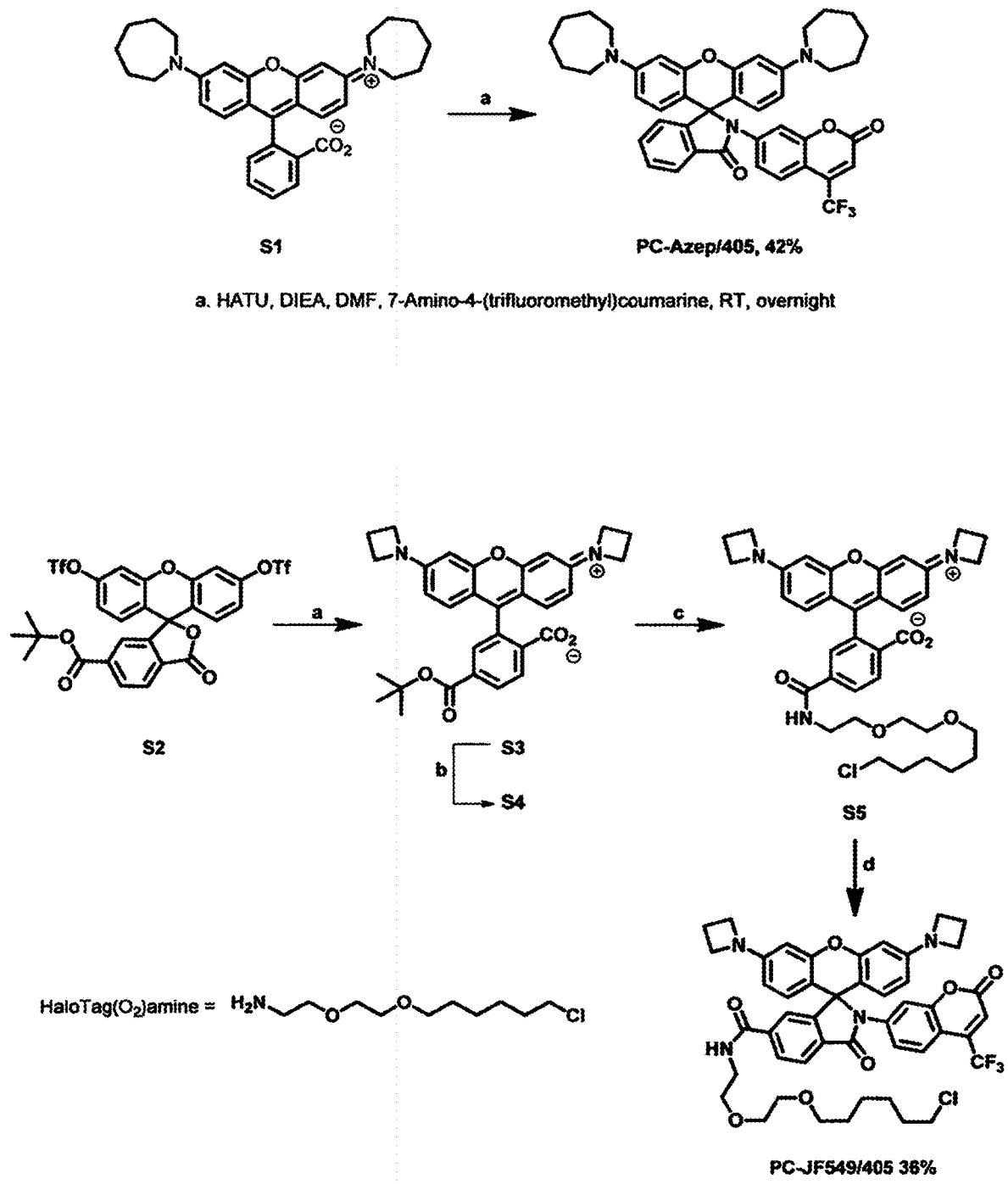
Figure 17:
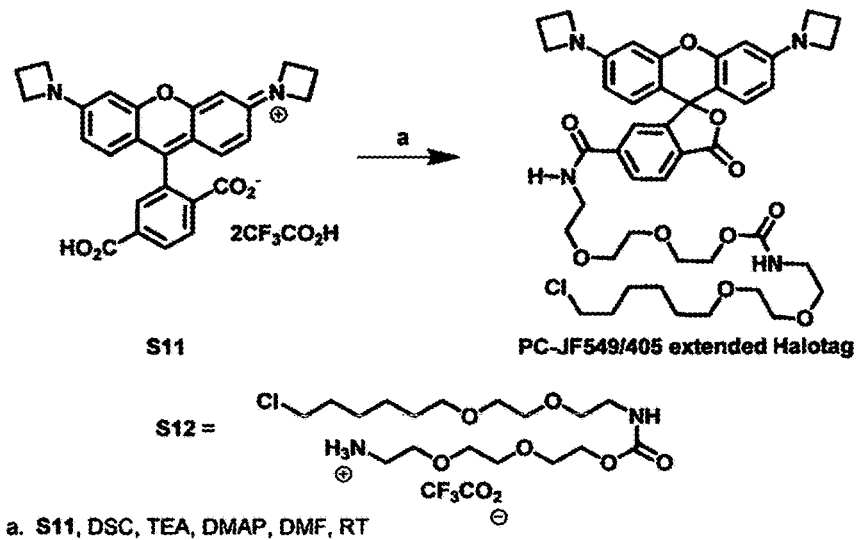
Figure 17:
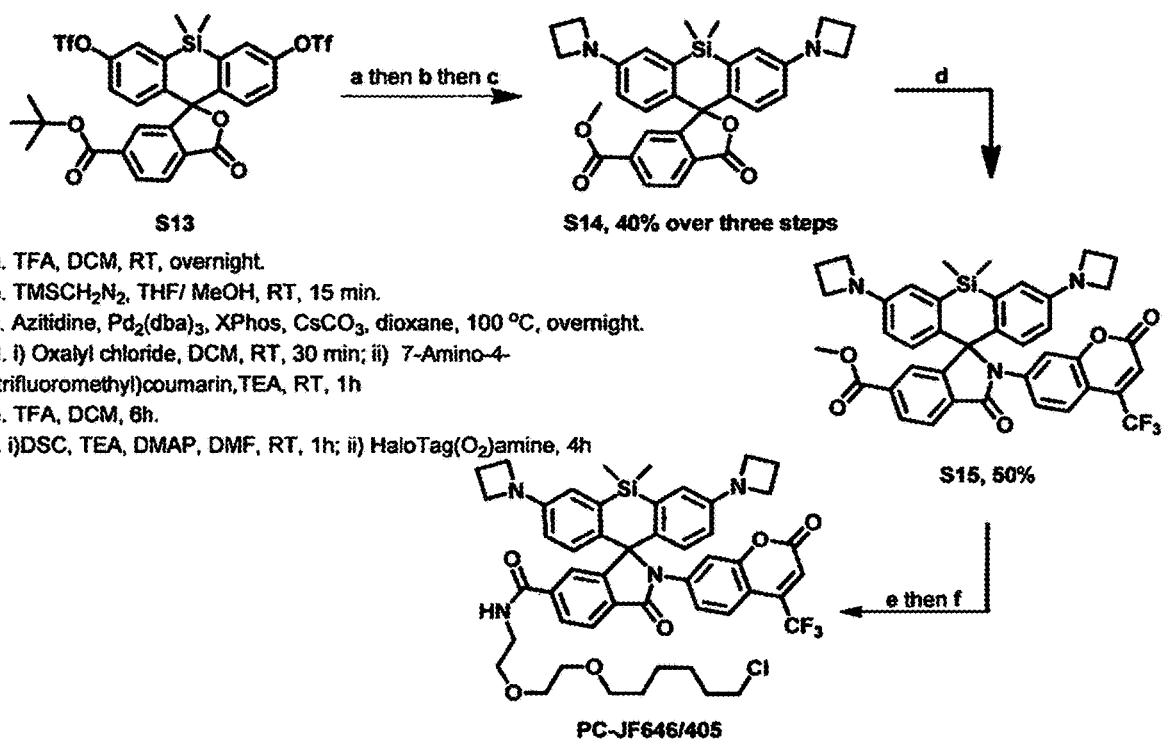

Compounds according to the present invention make it possible to produce super-resolution images of subcellular structures in live cells. FIG. 14 shows a super-resolution image of a nucleus using Photo-activated Localization Microscopy ("PALM"). To produce the image, cells were labeled with a compound according to the present invention. Two beams of light—one generating continuous illumination, while the other is pulsed—are used in the imaging. The compounds flicker and produce the shown image without the need for chemical additives, buffers or uncaging methods. General methods for super-resolution imaging are presented in Godin et al. "Super-Resolution Microscopy Approaches for Live Cell Imaging", *Biophys J.* 2014, 107, 1777-1784, which is incorporated-by-reference into this document for all purposes.

FIG. 28 shows a super-resolution image of live U2OS cells expressing H2B and labeled with PC-JF549-HT. It further shows the overlay with a diffraction limited fluorescence image with H2B expressing JF635-HT with a mean localization precision of 37 nm. FIG. 29 shows a super-resolution image of mitochondria expressing TOMM20 and labeled with PC-JF549-HT. The mean localization precision is 28 nm. FIG. 30 shows super-resolution iPALM images of actin in ptk2 cells transfected with lifeact-halo, and labeled with the PC-JF549-HT. FIG. 31 shows super-resolution images of tubulin in ptk2 cells expressing HaloTag and labeled with the PC-JF549-HT. FIG. 32 shows super-resolution iPALM images of tubulin in COS7 cells targeted with an antibody which is labeled with PC-AF594-NHS. FIG. 33 shows super-resolution iPALM images of tubulin in COS7 cells targeted with an antibody which is labeled with PC-AF594-NHS.

Experimental

Symbols and Abbreviations

| | |
|---|---|
| AF | AlexaFluor ® |
| Azep | Azepane |
| BG-NH$_2$ | 6-((4-(aminomethyl)benzypoxy)-9H-purin-2-amine |
| C$_6$D$_6$ | Deuterated benzene |
| CAM | Ceric ammonium molybdate |
| Cbz-NH$_2$ | Benzyl carbamate |
| CDCl$_3$ | Deuterated chloroform |
| CD$_3$CN | Deuterated acetonirtile |
| conc. | Concentrated |
| CsCO$_3$ | Cesium carbonate |
| DCC | Dicyclohexylcarbodiimide |
| DCM | Dichloromethane |
| DIEA | N,N-Diisopropylethylamine |
| DMAP | 4-Dimethylaminopyridine |
| DMF | N,N-Dimethylformamide |
| DSC | N,N'-Disuccinimidyl carbonate |
| EDC | 3-(Ethyliminomethyleneamino)-N,N-dimethylpropan-1-amine |
| ESI | Electrospray Ionization |
| Et$_3$N | Triethylamine |
| EtOAc | Ethyl Acetate |
| h | Hours |
| H$_2$O | Water |
| H$_2$SO$_4$ | Sulfuric acid |
| HATU | 1-[Bis(dimethylamino)methylene]-1H-1,2,3-triazolo[4,5-b]pyridinium 3-oxide hexafluorophosphate |
| HCL | Hydrochloric acid |
| HOBT | Hydroxybenzotriazole |
| HPLC | High Performance Liquid Chromatography |
| Hz | Hertz |
| JF | JaneliaFluor ® |
| LC/MS | Liquid chromatography/Mass spectrometry |
| μL | Microliter |
| MeCN | Acetonitrile |
| MeOD-d$_4$ | Deuterated methanol |
| MeOH | Methanol |
| mg | Milligram |
| mL | Milliliter |
| mm | millimeter |
| mmol | Millimol |
| min | Minutes |
| nm | Nanometer |
| Na$_2$SO$_4$ | Sodium Sulfate |
| NaOH | Sodium Hydroxide |
| NaOMe | Sodium methoxide |
| NHS | N-Hydroxysuccinimide |
| NMR | Nuclear Magnetic Resonance |
| PC | Photochromic |
| Pd/C | Palladium over carbon |
| Pd$_2$(dba)$_3$ | Tris(dibenzylideneacetone)dipalladium(0) |
| PEG | Polyethelene glycol |
| ppm | Part per million |
| quant | Quantitative |
| s | Seconds |
| RT | Room temperature |
| TFA | Trifluoroacetic acid |
| TLC | Thin layer chromatorgraphy |
| TMSCH$_2$N$_2$ | Diazomethane |
| TMS | Tetramethylsilane |
| TSTU | N,N,N',N'-Tetramethyl-O-(N-succinimidyl)uronium tetrafluoroborate |
| TEA | Triethyl amine |
| THF | Tetrahydrofuran |
| TFA | Trifluoroacetic acid |
| UV | Ultraviolet |
| Xantphos | 4,5-Bis(diphenylphosphino)-9,9-dimethylxanthene |
| XPhos | 2-Dicyclohexylphosphino-2',4',6'-triisopropylbiphenyl |
| % v/v | Volume/volume percent |
| % wt/wt | Weight/weight percent |
| ° C. | Degrees Celsius |

I. Materials and Methods

All starting materials were obtained from commercial sources and were used as received without further purification. Anhydrous solvents, in septum-sealed bottles, were used for all chemical reactions, which were conducted either under ambient conditions in a 4-dram glass vial or round bottomed flask or, when specified, under argon atmosphere in a sealed septum-capped vial. The reaction progress was monitored by TLC chromatography on pre-coated TLC glass plates (silica gel 60 $F_{254}$, 250 μm thickness) and TLC chromatograms were visualized by a UV lamp or developed with CAM, permanganate or iodine stains. When possible, LC/MS (4.6 mm×150 mm 5 μm C18 column; 5 μL injection; 10-95% MeCN/$H_2O$, linear gradient, with constant 0.1% v/v TFA additive; 20 min run; 1 mL/min flow; ESI; positive ion mode; UV detection at 254 nm and 550 nm) was also used to check reaction progress.

Purification of organic molecules was performed via silica gel chromatography on an automated purification system using pre-packed silica gel columns, or via reverse phase HPLC (10-95%, 20-80% or 30-70% MeCN/$H_2O$, linear gradient, with constant 0.1% v/v TFA additive; 23 min run, 42 mL/min flow, detection at 254 nm, 500 nm, 550 nm and 650 nm. Purity was confirmed by analytical HPLC (4.6 mm×150 mm 5 μm C18 column; 5 μL injection; 10-95% $CH_3CN/H_2O$ linear gradient with constant 0.1% v/v TFA additive; 20 min run; 1 mL/min flow; ESI, positive ion mode, detection at 254 nm, 500 nm, 550 nm and 650 nm.

NMR spectra were recorded on a 400 MHz spectrometer. $^1H$ and $^{13}C$ chemical shifts (δ) were referenced to TMS or residual solvent peaks. Data for $^1H$ NMR spectra are reported as follows: chemical shift (δ ppm), multiplicity (s=singlet, d=doublet, t=triplet, q=quartet, dd=doublet of doublets, m=multiplet), coupling constant (Hz), integration. Data for $^{13}C$ NMR spectra are reported by chemical shift (δ ppm).

1. Synthesis of the Photochromic JaneliaFluor Dyes (Scheme 1, FIGS. 21-22)

All the dyes presented in Scheme 1, are synthesized from two advanced intermediates (S1 and S2) whose synthesis have been described previously by Grimm et al.[1] From these intermediates, 7 different photochromic JaneliaFluor dyes have been synthesized, all equipped with a coumarin switch—responsible for the photochromic behavior, and a biological handle to allow for the specific targeting of proteins-of-interest. To target self-labeling enzymes such as HaloTag[2] and SNAPTag,[3] three types of linkers (HTL, exHTL,[4] PG-NH$_2$ in Scheme 1 inset) were covalently attached to the PC-JaneliaFluor dyes. In addition, NHS and taxol variants of these PC-JaneliaFluor dyes where prepared to allow for antibody, and tubulin labeling, respectively. Although not shown here, other biological handles such as azides, alkynes and tetrazenes for click-chemistry or biotin can be covalently introduced into the molecular structure of these dyes to increase the range of applications of these probes.

Depending on the nature of the heteroatom on the rhodamine (X in Scheme 1), different synthetic strategies where employed to couple the 7-amino-4-(trifluoromethyl)-coumarin to the rhodamine. In polar solvents such as DMF, rhodamines (X=O) are present in their "open" quinoidal zwitterionic form, exposing the carboxylate group at the 3-position and rendering it susceptible to activation and subsequent amidation. Thus in cases where the molecular structure features two reactive carboxylate moieties, such as intermediate S3, care needs to be taken to achieve selective activation/amidation.

On the contrary, silicorhodamines (X=Si(CH$_3$)$_2$) tend to be present in the closed form, effectively reducing the reactivity of the carboxylate at the 3'-position, and its susceptibility to activation/amidation under mild coupling conditions, example HATU. However, under harsh coupling conditions, for example oxalyl chloride, the silicorhodamine will open to the quinoidal form which will allow for the coupling to take place at the 3'-position.

In order to synthesize the HaloTag (PC-JF549-HT) and extended HaloTag (PC-JF549-exHT) version of PC-JaneliaFluor 549, Scheme 1, the methyl ester at the 6'-position in S1 was hydrolyzed under basic conditions to reveal the carboxylate, S3, which was activated with DCC to result in the activated NHS ester which was subsequently reacted with HTL, S4, or exHTL, S5, in the presence of excess Hünig's base to attach the biological handle. To introduce the switch at the 3'-position, the carboxylate was activated by HATU and 7-amino-4-(trifluoromethyl) coumarin to yield the desired fluorophore. It is beneficial to note that the same synthetic targets were also attained, with similar yields, by first coupling the 7-amino-4-(trifluoromethyl) coumarin to Si, followed by the hydrolyses of the methyl ester and the attachment of the biological handle. This particular path was taken to synthesize both the SNAP variant, PC-JF549-SNAP and the NHS variant, PC-JF549-NHS, via intermediate S6. To synthesize the docetaxyl variant PC-JF549-Tx, the activated NHS ester was first coupled with 7-aminooctanoic acid, which will act as a spacer between the rhodamine and docetaxyl, to produce intermediate S8 which was subsequently activated and coupled with the activated docetaxel, Tx in Scheme 1 inset, to get the desired fluorophore.

In the case of photochromic silicorhodamine, S2 was activated with oxalyl chloride to produce the acyl chloride which was then reacted with 7-amino-4-(trifluoromethyl) coumarin in the presence of excess Hünig's base to yield intermediate S7, which was then hydrolyzed under basic condition, and then activated with HATU and coupled with the respective amine to get the HaloTag and SNAP tag versions, PC-JF646-HT and PC-JF646-SNAP, respectively.

2. General Experimental Information for Synthesis of Compounds for Scheme 1

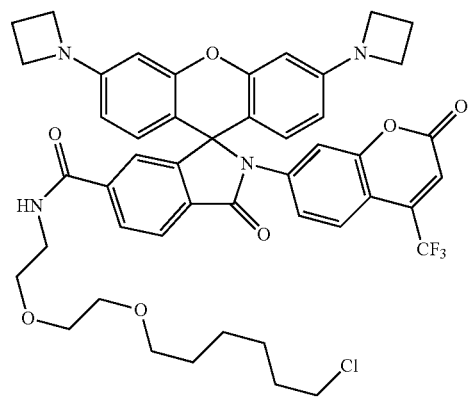 [SMILES: O=C(NCCOCCOCCCCCCCl)c1ccc2c(c1)C1(c3ccc(N4CCC4)cc3Oc3cc(N4CCC4)ccc31)N(c1ccc3c(C(F)(F)F)cc(=O)oc3c1)C2=O]

3',6'-di(azetidin-1-yl)-N-(2-(2-((6-chlorohexyl)oxy) ethoxy)ethyl)-3-oxo-2-(2-oxo-4-(trifluoromethyl)-2H-chromen-7-yl)spiro[isoindoline-1,9'-xanthene]-6-carboxamide (PC-JF549-HT): A vial was charged with S4[1] (16 mg, 0.024 mmol), 7-amino-4-(trifluoromethyl) coumarin (11 mg, 0.048 mmol, 2 eq.), HATU (28 mg, 0.073 mmol, 3 eq.), DIEA (42 μL, 0.24 mmol, 10 eq.) and DMF (300 μL). Contents were stirred at room temperature and ambient atmosphere for 24 h, after which the solvent was concentrated to dryness, and the crude product was purified by silica gel chromatography (0-30% EtOAc/DCM, linear gradient) to afford PC-JF549-HT (8 mg, 38%). LRMS (ESI) calcd for $C_{47}H_{46}ClF_3N_4O_7$ [M]$^+$ 871.4, found 871.4

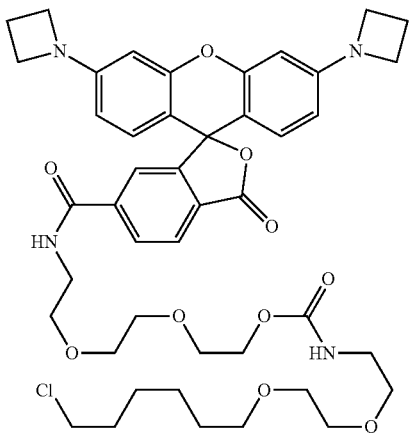 [SMILES: O=C(NCCOCCOCCCCCCCl)OCCOCCOCCNC(=O)c1ccc2c(c1)C1(OC2=O)c2ccc(N3CCC3)cc2Oc2cc(N3CCC3)ccc21]

2-(2-(2-(3',6'-di(azetidin-1-yl)-3-oxo-3H-spiro[isobenzofuran-1,9'-xanthene]-6-carboxamido)ethoxy)ethoxy)ethyl (2-(2-((6-chlorohexyl)oxy)ethoxy)ethyl)carbamate (S5): A vial was charged with S3[1] (10 mg, 0.015 mmol), DSC (11 mg, 0.044 mmol, 3.0 eq.), DMAP (0.18 mg, 0.001 mmol, 0.1 eq.), DIEA (26 µL, 0.15 mmol, 10 eq.) and DMF (300 µL), and contents were stirred at room temperature and ambient atmosphere for 1 hour before exHTL[4] (23 mg, 0.044 mmol, 3 eq.) was added and the resultant mixture was stirred for an additional 24 h. The solvent was concentrated to dryness, and the crude product was purified by silica gel chromatography (0-10% MeOH/DCM, linear gradient) to afford S5 (7.4 mg, 61%). $^1$H NMR (CDCl$_3$, 400 MHz) δ8.03 (s, 2H), 7.56 (s, 1H), 6.89 (s1H), 6.54 (d, J=8.6 Hz, 2H), 6.20 (d, J=2.3 Hz, 2H), 6.09 (dd, J=8.6, 2.3 Hz, 2H), 5.23 (s, 1H), 4.12 (t, J=4.8 Hz, 2H), 3.91 (t, J=7.3 Hz, 8H), 3.65-3.50 (m, 16H), 3.49 (s, 2H), 3.44 (t, J=6.8 Hz, 2H), 3.33 (q, J=5.3 Hz, 2H), 2.38 (p, J=7.2 Hz, 4H), 1.83-1.71 (m, 2H), 1.59 (p, J=6.8 Hz, 2H), 1.45 (p, J=6.7 Hz, 2H). 1.36 (m, 2H).

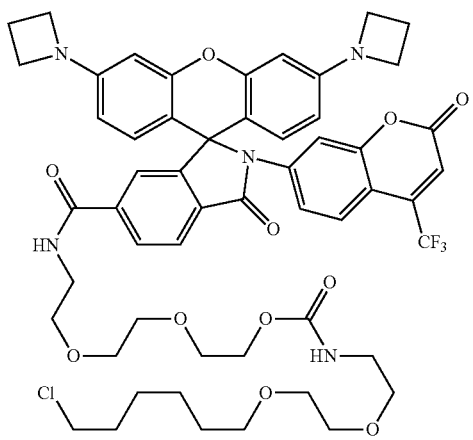 [SMILES: O=C(NCCOCCOCCCCCCCl)OCCOCCOCCNC(=O)c1ccc2c(c1)C1(c3ccc(N4CCC4)cc3Oc3cc(N4CCC4)ccc31)N(c1ccc3c(C(F)(F)F)cc(=O)oc3c1)C2=O]

2-(2-(2-(3',6'-di(azetidin-1-yl)-3-oxo-2-(2-oxo-4-(trifluoromethyl)-2H-chromen-7-yl)spiro[isoindoline-1,9'-xanthene]-6-carboxamido)ethoxy)ethoxy)ethyl (2-(2-((6-chlorohexyl)oxy)ethoxy)ethyl)carbamate (PC-JF549-ExHT): A vial was charged with S5 (9 mg, 0.011 mmol), 7-amino-4-(trifluoromethyl) coumarin (7 mg, 0.033 mmol, 3 eq.), HATU (12 mg, 0.033 mmol, 3 eq.), DIEA (19 µL, 0.11 mmol, 10 eq.) and DMF (300 µL). Contents were stirred at room temperature and ambient atmosphere for 24 h, after which the solvent was concentrated to dryness, and the crude product was purified by silica gel chromatography (0-5% MeOH/DCM, linear gradient) to afford PC-JF549-exHT (2 mg, 18%).$^1$H NMR (CDCl$_3$, 400 MHz) δ8.05 (d, J=7.9 Hz, 1H), 7.92 (d, J=8.0 Hz, 1H), 7.49 (m, 2H), 7.30 (dd, J=8.9, 2.1 Hz, 1H), 7.17 (d, J=2.1 Hz, 1H), 6.79 (s, 1H), 6.65 (s, 1H), 6.57 (d, J=8.6 Hz, 2H), 6.12 (d, J=2.3 Hz, 2H), 6.02 (dd, J=8.6, 2.3 Hz, 2H), 5.23 (s, 1H), 4.14 (s, 2H), 3.89 (t, J=7.3 Hz, 8H), 3.67-3.50 (m, 18H), 3.45 (t, J=6.6 Hz, 2H), 3.33 (d, J=5.6 Hz, 2H), 2.37 (p, J=7.2 Hz, 4H), 1.77 (p, J=6.7 Hz, 2H), 1.60 (d, J=14.6 Hz, 2H), 1.44 (q, J=8.1, 6.8 Hz, 2H), 1.37 (d, J=7.0 Hz).

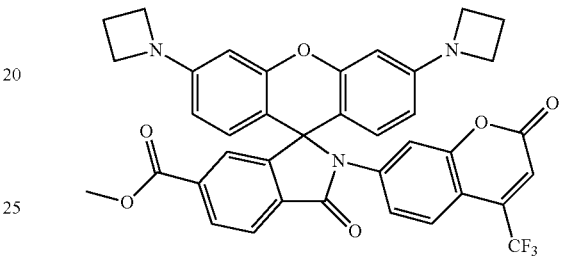

methyl 3',6'-di(azetidin-1-yl)-3-oxo-2-(2-oxo-4-(trfluoromethyl)-2H-chromen-7-yl)spiro[isoindoline-1,9'-xanthene]-6-carboxylate (S6): A vial was charged with S1[1] (50 mg, 0.107 mmol), 7-amino-4-(trifluoromethyl) coumarin (73 mg, 0.320 mmol, 3 eq.), HATU (122 mg, 0.320 mmol, 3.0 eq.), DIEA (200 µL, 1.07 mmol, 10 eq.) and DMF (1.00 mL). Contents were stirred at room temperature and ambient atmosphere for 24 h, after which the solvent was concentrated to dryness, and the crude product was purified by silica gel chromatography (0-30% EtOAc/DCM, linear gradient) to afford S6 (45 mg, 62%). $^1$H NMR (CDCl$_3$, 400 MHz) δ8.16 (dd, J=8.0, 1.4 Hz, 1H), 8.06 (dd, J=8.0, 0.7 Hz, 1H), 7.69 (dd, J=1.3, 0.7 Hz, 1H), 7.49 (dq, J=8.9, 1.9 Hz, 1H), 7.29 (dd, J=8.9, 2.2 Hz, 1H), 7.16 (d, J=2.1 Hz, 1H), 6.65 (d, J=0.9 Hz, 1H), 6.57 (d, J=8.6 Hz, 2H), 6.13(d, J=2.3 Hz, 2H), 6.03 (dd, J=8.6, 2.3 Hz, 2H), 3.89 (t, J=7.3 Hz, 8H), 3.85 (s, 3H), 2.37 (p, J=7.3 Hz, 4H).

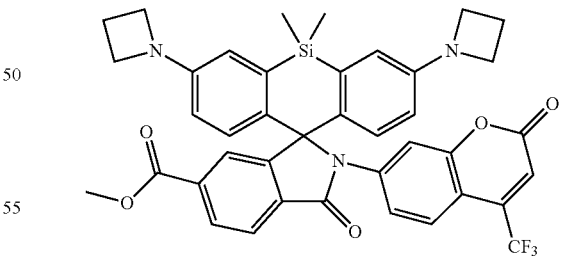

methyl 3,7-di(azetidin-1-yl)-5,5-dimethyl-3'-oxo-2'-(2-oxo-4-(trifluoromethyl)-2H-chromen-7-yl)-5H-spiro[dibenzo[b,e]siline-10,1'-isoindoline]-6'-carboxylate (S7): A vial was charged with S2[1] (60 mg, 0.117 mmol), oxalyl chloride (12 µL, 0.141 mmol, 1.2 eq.) and DCM (1.00 mL) and the content was stirred at room temperature and ambient atmosphere for 30 minutes. 7-amino-4-(trifluoromethyl) coumarin (81 mg, 0.352 mmol, 3 eq.) and DIEA (126 µL, 0.704 mmol, 6 eq.) were then added and the contents were stirred for 1 h, after which the solvent was concentrated to dryness, and the crude product was purified by silica gel chromatography (0-30% EtOAc/DCM, linear gradient) to afford S7 (53 mg, 62%). $^1$H NMR (CDCl$_3$, 400 MHz) δ8.09-7.95 (m, 2H), 7.78 (m, 1H), 7.60 (td, J=4.6, 2.2 Hz, 1H), 7.54 (tt, J=5.6, 1.1 Hz, 1H), 7.45 (m, 1H), 6.86 (d, J=2.6 Hz, 1H), 6.76 (ddd, J=8.8, 3.7, 1.2 Hz, 2H), 6.62 (d, J=2.8 Hz, 1H), 6.60 (s, 1H), 6.42 (dd, J=8.9, 2.7 Hz, 1H), 6.24 (dd, J=8.8, 2.6 Hz, 1H), 3.88 (t, J=7.2 Hz, 4H), 3.81 (s, 3H), 3.65 (t, J=6.2 Hz, 2H), 3.31 (t, J=6.6 Hz, 2H), 2.35 (p, J=7.2 Hz, 2H), 2.06 (p, J=6.3 Hz, 2H), 0.71 (s, 3H), 0.59 (s, 3H).

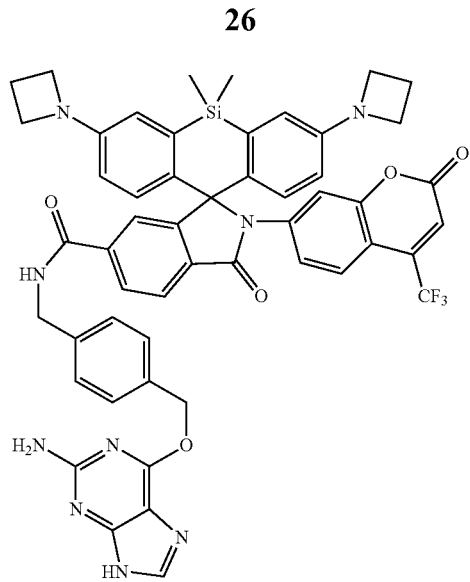

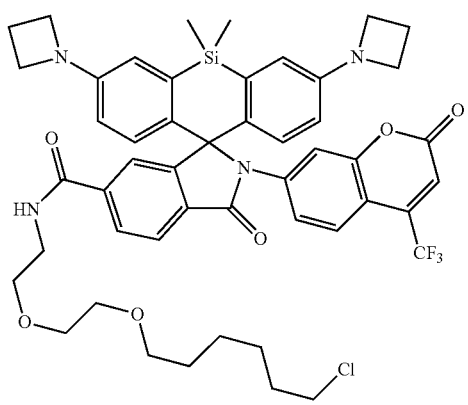 [SMILES: C[Si]1(C)c2cc(N3CCC3)ccc2C2(c3cc(C(=O)NCCOCCOCCCCCCCl)ccc3C(=O)N2c2ccc3c(C(F)(F)F)cc(=O)oc3c2)c2ccc(N3CCC3)cc21]

N-(4-(((2-amino-9H-purin-6-yl)oxy)methyl)benzyl)-3,7-di(azetidin-1-yl)-5,5-dimethyl-3'-oxo-2'-(2-oxo-4-(trifluoromethyl)-2H-chromen-7-yl)-5H-spiro[dibenzo[b,e]siline-10,1'-isoindoline]-6'-carboxamide (PC-JF549-SNAP): A vial was charged with hydrolyzed S7 (18 mg, 0.025 mmol), BG-NH2 (21 mg, 0.076 mmol, 3 eq.), HATU (29 mg, 0.076 mmol, 3.0 eq.), DIEA (44 µL, 0.25 mmol, 10 eq.) and DMF (300 µL). Contents were stirred at room temperature and ambient atmosphere for 24 h, after which the solvent was concentrated to dryness, and the crude product was purified by silica gel chromatography (0-10% MeOH/DCM, linear gradient) to afford PC-JF646-SNAP (11 mg, 45%). LRMS (ESI) calcd for C$_{52}$H$_{44}$F$_3$N$_9$O$_5$Si [M]$^+$ 960.1, found 960.4

3,7-di(azetidin-1-yl)-N-(2-(2-((6-chlorohexyl)oxy)ethoxy)ethyl)-5,5-dimethyl-3'-oxo-2'-(2-oxo-4-(trifluoromethyl)-2H-chromen-7-yl)-5H-spiro[dibenzo[b,e]siline-10,1'-isoindoline]-6'-carboxamide (PC-JF646-HT): A vial was charged with S7 (53 mg, 0.073 mmol), NaOH (734 µL, 1M, 10 eq.) MeOH (5.0 mL) and THF (2.5 mL). Content was stirred at room temperature and ambient atmosphere for 24 h, after which HCl (770 µL, 1M, 10.5 eq.) was added to quench the reaction. The organic layer was extracted with DCM (3×10 mL). Organic layers combined, dried (Na$_2$SO$_4$), and concentrated. The hydrolyzed residue was carried to the next step without further purification. A vial was charged with hydrolyzed S7 (20 mg, 0.028 mmol), HTL (28 mg, 0.085 mmol, 3 eq.), HATU (32 mg, 0.085 mmol, 3.0 eq.), DIEA (49 µL, 0.28 mmol, 10 eq.) and DMF (300 µL). Contents were stirred at room temperature and ambient atmosphere for 24 h, after which the solvent was concentrated to dryness, and the crude product was purified by silica gel chromatography (0-40% EtOAc/DCM, linear gradient) to afford PC-JF646-HT (10.4 mg, 40%). $^1$H NMR (CDCl$_3$, 400 MHz) δ8.00 (d, J=7.8 Hz, 1H), 7.72 (dd, J=9.1, 2.3 Hz, 1H), 7.69 (dd, J=7.9, 1.5 Hz, 1H), 7.61 (d, J=2.3 Hz, 1H), 7.43 (dd, J=9.1, 2.0 Hz, 1H), 7.30 (d, J=1.2 Hz, 1H), 6.76 (d, J=8.8 Hz, 2H), 6.62 (d, J=4.8 Hz, 1H), 6.61 (d, J=2.7 Hz, 2H), 6.59 (s, 1H), 6.24 (d, J=2.6 Hz, 1H), 6.22 (d, J=2.7 Hz, 1H), 3.88 (t, J=7.3 Hz, 8H), 3.64-3.54 (m, 8H), 3.51 (t, J=6.7 Hz, 2H), 3.41 (t, J=6.7 Hz, 2H), 2.35 (p, J=7.2 Hz, 4H), 1.79-1.69 (m, 2H), 1.58-1.50 (m, 2H), 1.47-1.37 (m, 2H), 1.37-1.27 (m, 2H), 0.70 (s, 3H), 0.57 (s, 3H).

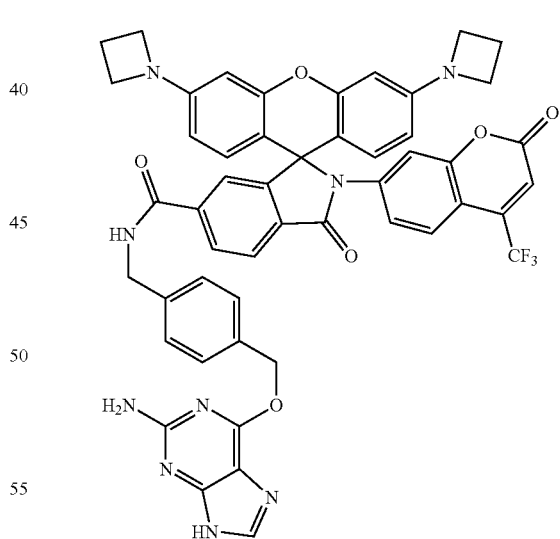

N-(4-(((2-amino-9H-purin-6-yl)oxy)methyl)benzyl)-3',6'-di(azetidin-1-yl)-3-oxo-2-(2-oxo-4-(trifluoromethyl)-2H-chromen-7-yl)spiro[isoindoline-1,9'-xanthene]-6-carboxamide (PC-JF549-SNAP): A vial was charged with S6 (70 mg, 0.103 mmol), NaOH (1.03 mL, 1M, 10 eq.) MeOH (5.0 mL) and THF (2.5 mL). Content was stirred at room temperature and ambient atmosphere for 24 h, after which HCl (1.08 mL, 1M, 10.5 eq.) was added to quench the reaction. The organic layer was extracted with DCM (3×10 mL). Organic layers combined, dried (Na$_2$SO$_4$), and concentrated. The hydrolyzed residue was carried to the next step without further purification. A vial was charged with hydrolyzed S6 (10 mg, 0.015 mmol), BG-NH2 (12 mg, 0.045 mmol, 3 eq.), HATU (17 mg, 0.045 mmol, 3.0 eq.), DIEA (26 μL, 0.15 mmol, 10 eq.) and DMF (300 μL). Contents were stirred at room temperature and ambient atmosphere for 24 h, after which the solvent was concentrated to dryness, and the crude product was purified by silica gel chromatography (0-40% EtOAc/DCM, linear gradient) to afford PC-JF549-SNAP (12 mg, 87%). $^1$H NMR (CDCl$_3$, 400 MHz) δ8.55 (s, 1H), 8.24 (d, J=8.4 Hz, 1H), 8.05 (dd, J=8.0, 1.4 Hz, 1H), 8.00 (d, J=7.9 Hz, 1H), 7.77 (t, J=5.6 Hz, 1H), 7.69 (s, 1H), 7.52 (d, J=3.7 Hz, 1H), 7.37 (d, J=7.8 Hz, 1H), 7.31 (s, J=7.2 Hz, 2H), 7.23 (d, J=7.9 Hz, 2H), 6.93 (t, J=8.0 Hz, 1H), 6.57 (d, J=8.5 Hz, 2H), 6.54 (dd, J=8.0, 1.4 Hz, 1H), 6.40 (td, J=7.7, 7.3, 1.4 Hz, 1H), 6.03 (d, J=8.7 Hz, 2H), 5.99 (m, 3H), 5.38 (s, 2H), 4.49 (s, 2H), 3.84 (h, J=7.3 Hz, 8H), 2.34 (p, J=7.3 Hz, 4H).

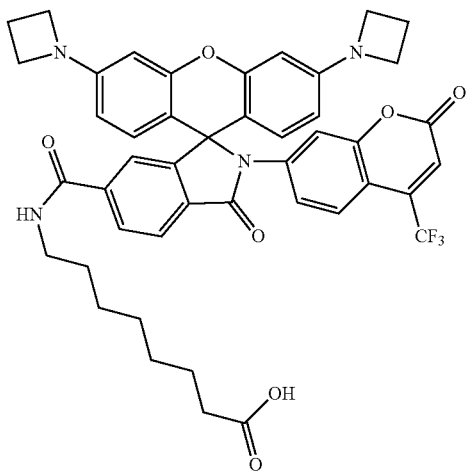

8-(3',6'-di(azetidin-1-yl)-3-oxo-2-(2-oxo-4-(trifluoromethyl)-2H-chromen-7-yl)spiro[isoindoline-1,9'-xanthene]-6-carboxamido)octanoic acid (S8): A vial was charged with PC-JF549-NHS (5 mg, 0.007 mmol), 8-aminooctanoic acid (3.30 mg, 0.021 mmol, 3 eq.), DIEA (11 μL, 0.066 mmol, 10 eq.) and DMF (300 μL). Contents were stirred at room temperature and ambient atmosphere for 24 h, after which the solvent was concentrated to dryness, and the crude product was purified by reverse phase HPLC (10-95% MeCN/H$_2$O, linear gradient, with constant 0.1% v/v TFA additive; 23 min run, 42 mL/min flow, detection at 550 nm) to afford S8 (5 mg, 94%). $^1$H NMR (CD$_3$CN, 400 MHz) δ8.05 (dd, J=7.9, 0.7 Hz, 1H), 7.89 (dd, J=7.9, 1.5 Hz, 1H), 7.49 (dt, J=8.9, 2.0 Hz, 1H), 7.36 (d, J=1.2 Hz, 1H), 7.29 (dd, J=8.9, 2.2 Hz, 1H), 7.15 (dd, J=9.7, 2.1 Hz, 1H), 6.66 (s, 1H), 6.57 (dd, J=8.6, 2.4 Hz, 2H), 6.20-6.10 (m, 3H), 6.04 (m, 2H), 3.90 (t, J=7.3 Hz, 8H), 3.36 (q, J=6.7 Hz, 2H), 2.35 (dq, J=22.4, 7.3 Hz, 6H), 1.57 (dt, J=20.0, 6.9 Hz, 4H), 1.31 (s, 6H).

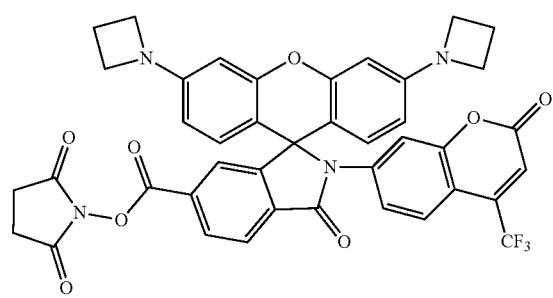 [SMILES: O=C(ON1C(=O)CCC1=O)c1ccc2c(c1)C1(c3ccc(N4CCC4)cc3Oc3cc(N4CCC4)ccc31)N(c1ccc3c(C(F)(F)F)cc(=O)oc3c1)C2=O]

2,5-dioxopyrrolidin-1-yl 3',6'-di(azetidin-1-yl)-3-oxo-2-(2-oxo-4-(trifluoromethyl)-2H-chromen-7-yl)spiro[isoindoline-1,9'-xanthene]-6-carboxylate (PC-JF549-NHS): A vial was charged with S6 (45 mg, 0.066 mmol), NaOH (660 μL, 1M, 10 eq.) MeOH (5.0 mL) and THF (2.5 mL). Content was stirred at room temperature and ambient atmosphere for 24 h, after which HCl (693 μL, 1M, 10.5 eq.) was added to quench the reaction. The organic layer was extracted with DCM (3×10 mL). Organic layers combined, dried (Na$_2$SO$_4$), and concentrated. The hydrolyzed residue was carried to the next step without further purification. A vial was charged with hydrolyzed S6 (40 mg, 0.06 mmol), TSTU (54 mg, 0.180 mmol, 3 eq.), DIEA (105 μL, 0.60 mmol, 10 eq.) and DMF (500 μL). Contents were stirred at room temperature and ambient atmosphere for 24 h, after which the solvent was concentrated to dryness, and the crude product was purified by silica gel chromatography (0-70% Hexanes/EtOAc, linear gradient) to afford PC-JF549-NHS (10 mg, 22%). $^1$H NMR (CD$_3$CN, 400 MHz) δ8.25 (dd, J=8.0, 1.5 Hz, 1H), 8.13 (dd, J=8.0, 0.8 Hz, 1H), 7.73 (dd, J=1.5, 0.7 Hz, 1H), 7.54 (dq, J=8.9, 2.0 Hz, 1H), 7.22 (dd, J=8.9, 2.2 Hz, 1H), 7.09 (d, J=2.1 Hz, 1H), 6.75 (d, J=1.0 Hz, 1H), 6.69 (d, J=8.4 Hz, 2H), 6.12 (q, J=2.3 Hz, 3H), 6.09 (d, J=2.3 Hz, 1H), 3.85 (t, J=7.3 Hz, 8H), 2.81 (s, 4H), 2.32 (p, J=7.3 Hz, 4H).

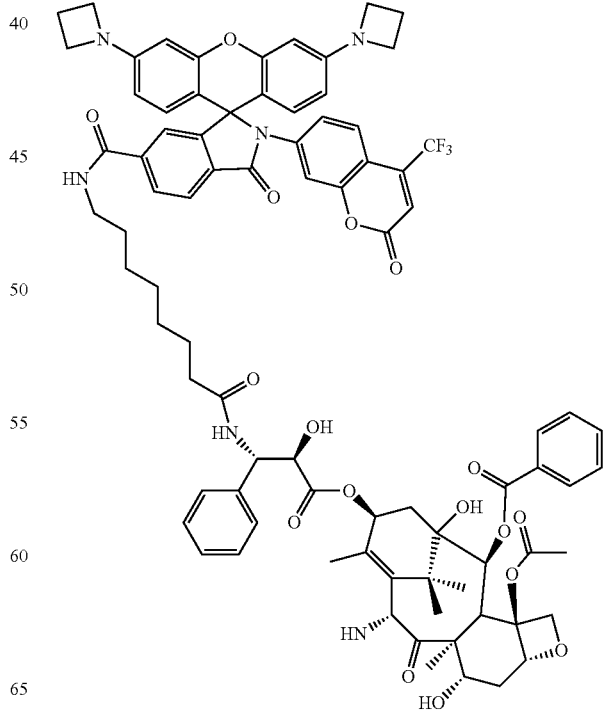

(2aR,4S,4aS,6R,9S,11S,12S,12bS)-12b-acetoxy-9-(((2R,3S)-3-(8-(3',6'-di(azetidin-1-yl)-3-oxo-2-(2-oxo-4-(trifluoromethyl)-2H-chromen-7-yl)spiro[isoindoline-1,9'-xanthene]-6-carboxamido)octanamido)-2-hydroxy-3-phenylpropanoyl)oxy)-4,6,11-trihydroxy-8,13,13-trimethyl-5-oxo-2a,3,4,4a,5,6,9,10,11,12,12a,12b-dodecahydro-1H-[7,11]methanocyclodeca[3,4]benzo[1,2-b]oxet-12-yl benzoate (PC-JF549-Tx): A vial was charged with S8 (4 mg, 0.005 mmol), Tx[5] (9.2 mg, 0.012 mmol, 2.5 eq.), HATU (3.7 mg, 0.01 mmol, 2 eq.), DIEA (43 μL, 0.250 mmol, 50 eq.) and DMF (500 μL). Contents were stirred at room temperature and ambient atmosphere for 48 h, after which the solvent was concentrated to dryness, and the crude product was purified by silica gel chromatography (0-10% MeOH/DCM, linear gradient) to afford PC-JF549-Tx (1.5 mg, 20%). LRMS (ESI) calcd for $C_{82}H_{82}F_3N_5O_{18}$ $[M]^+$ 1496.6, found 1496.5

3. Synthesis of the Photochromic JaneliaFluor Dyes part II (Scheme 2, FIGS. 23-25)

In the previous section, the coumarin switch and the biological handle were introduced to the fluorophore's molecular structure separately, and at different synthetic stages. This pathway increases the synthetic steps that include the precious fluorophore increasing the cost of the synthesis, and limits its generalizability. In another synthetic approach, the coumarin is designed to incorporate the biological handle in its molecular structure prior to its conjugation to the fluorophore. This reduces the number of synthetic steps with the fluorophore included, potentially reducing the overall synthetic cost, and allowing for the creation of libraries of fluorophores via conjugating this universal switch to existing fluorophores.

To prepare the universal coumarin switch, S5, the commercially acquired 4-bromo-2-hydroxybenzaldehyde was condensed with tent-butyl ethyl malonate to give the coumarin S1.[6] Palladium catalyzed cross-coupling with benzyl carbamate provided S2, whose carboxyl functionality, at the 3'-position, can be selectively de-protected with TFA to get S3. Activation of S3 with DCC and then amidation with a HTL, or any other biological handle, yielded S4, which upon reduction with hydrogen gas in the presence of a palladium catalyst produced the universal switch S5. The amine on S5 can now be condensed with any fluorophore of interest, for example JF549, scheme 2 inset, resulting in PC(II)-JF549-HY which is now rendered both photochromic and capable of labeling a specific protein-of-interest.

Unlike AlexaFluor dyes which are highly polar, JaneliaFluor dyes do not carry a net charge, and hence are cell-permeant and compatible with live-cell imaging. However, this comes with lower water-solubility. By adding an additional hydrophobic switch—the coumarin, water solubility can be further reduced, with potential detrimental effects on cellular labeling specificity as it introducing higher affinity to hydrophobic pockets. In scheme 2, we also demonstrate a pathway to introduce water solubilizing groups into the coumarin structure, prior to its conjugation to the JaneliaFluor, further demonstrating its versatility.

Activation of the carboxylic acid at the 3'-position of S3 with EDC in the presence of HOBT, and then amidation with PEG-NH$_2$ (Scheme 2 inset) produced intermediate S6, which now features the solubilizing PEG group, and the protected amine. It is also possible to introduce other types of solubilizing groups using the same approach. Removal of the carbamate protecting group in S6, yields S7, which can now be condensed to a JaneliaFluor dye, JF646-6-OMe to produce S8 which can now be hydrolyzed under basic conditions and then coupled to a biological handle such as a HTL as in PC-JF646-PEG-HT, or an NHS ester PC-JF646-PEG-NHS. The latter NHS activated JaneliaFluor dye is more suitable for immunostaining in fixed cells, due to its better water solubility, compared to PC-JF549-NHS, because of its enhanced water solubility.

4. General Experimental Information for Synthesis of Compounds for Scheme 2

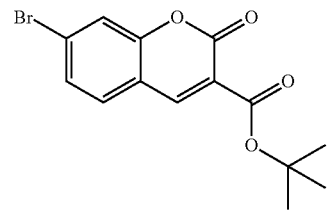 [SMILES: CC(C)(C)OC(=O)c1cc2ccc(Br)cc2oc1=O]

tert-butyl 7-bromo-2-oxo-2H-chromene-3-carboxylate (S1): A round bottomed flask was charged with 4-bromo-2-hydroxybenzaldehyde (2.0 g, 1.00 mmol), tert-butyl ethyl malonate (2.06 g, 1.10 mmol, 1.1 eq.), piperidine (0.15 mL, 0.15 mmol, 0.15 eq.) and acetonitrile (3.00 mL). The contents were stirred at room temperature and argon atmosphere for 24 hours, after which the solvent was concentrated to dryness, and the crude product purified via silica gel chromatography (1:1 Hexanes/DCM, linear gradient) to afford S1 (2.03 g, 63%). $^1$H NMR (CDCl$_3$, 400 MHz) δ8.34 (d, J=0.7 Hz, 1 H), 7.53 (dt, J=1.6, 0.8 Hz, 1H), 7.48-7.40 (m, 2H), 1.62 (s, 9H).

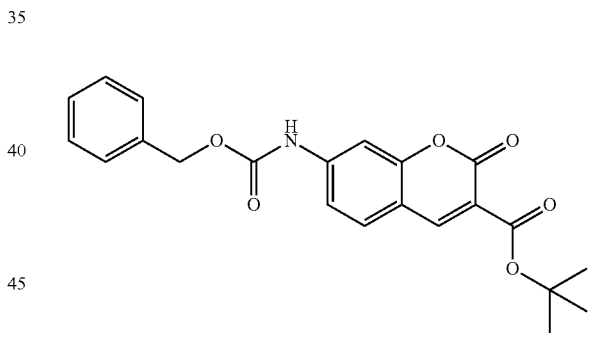

tert-butyl 7-(((benzyloxy)carbonyl)amino)-2-oxo-2H-chromene-3-carboxylate (S2): A vial was charged with S1 (1.0 g, 3.08 mmol), benzyl carbamate (0.93 g, 6.15 mmol, 2 eq.), Pd$_2$dba$_3$ (0.14 g, 0.15 mmol, 0.05 eq.), CsCO$_3$ (1.5 g, 4.61 mmol, 1.5 eq.) Xantphos (0.27 g, 0.46 mmol, 0.15 eq.). The vial was sealed and evacuated/backfilled with argon (3×). Toluene (6.0 mL) was added, and the reaction was flushed again with argon (3×). The reaction was then stirred at 100° C. for 24 h. It was then cooled down to RT, filtered through celite with DCM, concentrated to dryness, and the crude product purified via silica gel chromatography (0-50% EtOAc/Hexanes, linear gradient) to afford S2 (0.48 g, 39%). $^1$H NMR (CDCl$_3$, 400 MHz): δ8.34 (s, 1H), 7.50 (d, J=8.6 Hz, 1H), 7.47 (d, J=2.0 Hz, 1H), 7.43-7.33 (m, 6H), 6.96 (s, 1H), 5.23 (d, J=1.1 Hz, 2H), 1.59 (s, 9H).

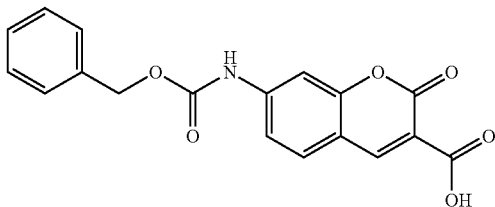 [SMILES: O=C(Nc1ccc2cc(C(=O)O)c(=O)oc2c1)OCc1ccccc1]

7-(((benzyloxy)carbonyl)amino)-2-oxo-2H-chromene-3-carboxylic acid (S3): A round bottomed flask was charged with S2 (1.74 g, 4.40 mmol), TFA (1.35 mL, 17.6 mmol, 4 eq.) and DCM (45 mL). The contents were stirred at room temperature and ambient atmosphere for 24 hours, after which toluene (10 mL) was added, and the DCM evaporated under reduced pressure. MeOH (10×2 mL) was then added to azeotropically remove the toluene. The crude product S3 was then used in the next step without further purification. $^1$H NMR (MeOD-$d_4$, 400 MHz): δ10.13 (s, 1H), 8.77 (s, 1H), 7.88 (s, 1H), 7.79-7.67 (m, 2H), 7.50-7.23 (m, 6H), 5.23 (s, 2H).

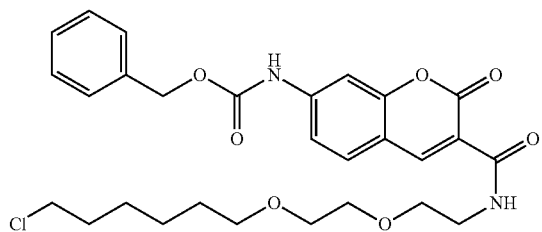 [SMILES: O=C(Nc1ccc2cc(C(=O)NCCOCCOCCCCCCCl)c(=O)oc2c1)OCc1ccccc1]

benzyl (3-((2-(2-((6-chlorohexyl)oxy)ethoxy)ethyl)carbamoyl)-2-oxo-2H-chromen-7-yl)carbamate (S4): A vial was charged with S3 (0.7 g, 2.06 mmol), HTL (0.55 g, 2.48 mmol, 1.2 eq.), EDC (0.47 g, 2.48 mmol, 1.2 eq.), HOBT (0.33 g, 2.48 mmol, 1.2 eq.) and DMF (9 mL). The reaction was then stirred at room temperature and ambient atmosphere for 24 h. The organic layer was extracted with DCM (3×30 mL). Organic layers combined, dried (Na$_2$SO$_4$), and concentrated. The crude product was purified via silica gel chromatography (0-30% EtOAc/DCM, linear gradient) to afford S4 (1.09 g, 96%). $^1$H NMR (CDCl$_3$, 400 MHz): δ8.98 (s, 1H), 8.74 (s, 1H), 7.67 (s, 1H), 7.61-7.49 (m, 2H), 7.43-7.27 (m, 6H), 5.22 (s, 2H), 3.67-3.55 (m, 8H), 3.32-3.40 (m, 4H), 1.80-1.67 (m, 2H), 1.63-1.53 (m, 2H), 1.47-1.29 (m, 4H).

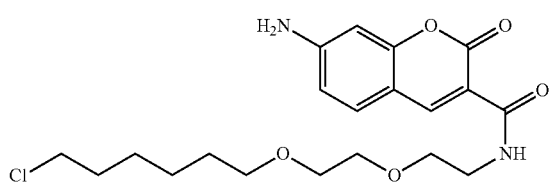 [SMILES: Nc1ccc2cc(C(=O)NCCOCCOCCCCCCCl)c(=O)oc2c1]

7-amino-N-(2-(2-((6-chlorohexyl)oxy)ethoxy)ethyl)-2-oxo-2H-chromene-3-carboxamide (S5): A round bottomed flask was charged with S4 (1.10 g, 2.02 mmol), Pd/C (60 mg, 0.61 mmol, 0.3 eq.) and EtOAc (3 mL). The flask was sealed with a rubber septum and evacuated/backfilled first with argon (3×), then with hydrogen gas (3×) via a balloon. The reaction was then stirred at room temperature and hydrogen atmosphere (via a balloon) for 48 hours. The reaction mixture was filtered over celite, washed with EtOAc (3×10 mL), concentrated, and the crude product was purified via silica gel chromatography (0-50% EtOAc/DCM, linear gradient) to afford S5 (0.26 g, 32%). $^1$H NMR (CDCl$_3$, 400 MHz): δ8.97 (s, 1H), 8.69 (s, 1H), 7.39 (d, J=8.0 Hz, 1H), 6.60 (dt, J=8.2, 4.2 Hz, 1H), 6.55 (s, 1H), 4.53 (s, 2H), 3.67-3.57 (m, 8H), 3.54-3.44 (m, 4H), 1.75 (p J=7.1 Hz, 2H), 1.62-1.50 (m, 2H), 1.47-1.30 (m, 4H).

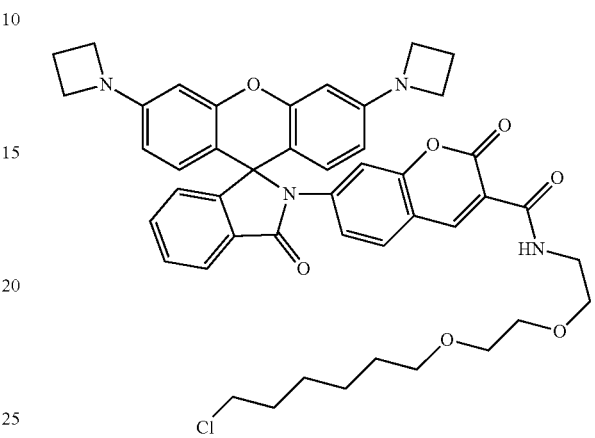

N-(2-(2-((6-chlorohexyl)oxy)ethoxy)ethyl)-7-(3',6'-di(azetidin-1-yl)-3-oxospiro[isoindoline-1,9'-xanthen]-2-yl)-2-oxo-2H-chromene-3-carboxamide (PC(II)-JF549-HT): A vial was charged with JF549[1] (25 mg, 0.061 mmol), S5 (75 mg, 0.183 mmol, 3 eq.), HATU (70 mg, 0.183 mmol, 3 eq.), DIEA (106 μL, 0.61 mmol, 10 eq.) and DMF (300 μL). Contents were stirred at room temperature and ambient atmosphere for 24 h, after which the solvent was concentrated to dryness, and the crude product was purified via reverse phase HPLC (10-95% MeCN/H$_2$O, linear gradient, with constant 0.1% v/v TFA additive; 23 min run, 42 mL/min flow, detection at 550 nm) to afford PC(II)-JF549-HT (3 mg, 6%). $^1$H NMR (CDCl$_3$, 400 MHz): δ8.89 (s, 1H), 8.74 (s, 1 H), 8.00 (dd, J=6.8, 1.9 Hz, 1H), 7.60-7.52 (m, 2H), 7.50 (d, J=8.6 Hz, 1H), 7.35 (dd, J=8.6, 2.0 Hz, 1H), 7.29 (d, J=2.0 Hz, 1H), 7.07 (dd, J=6.5, 1.8 Hz, 1H), 6.64 (d, J=8.5 Hz, 2H), 6.17 (d, J=2.3 Hz, 2H), 6.07 (dd, J=8.6, 2.3 Hz, 2H), 3.90 (t, J=7.2 Hz, 8H), 3.80-3.69 (m, 2H), 3.69-3.51 (m, 4H), 3.57 (t, J=6.8 Hz, 2H), 3.48 (t, J=6.7 Hz, 2H), 3.20 (qd, J=7.4, 3.4 Hz, 2H), 2.38 (p, J=7.2 Hz, 4H), 1.84-1.76 (m, 2H), 1.76-1.56 (m, 2H), 1.42-1.36 (m, 4H).

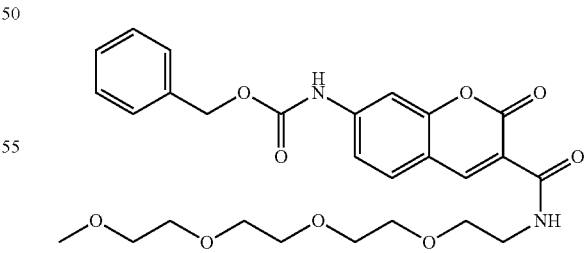

benzyl (3-((2,5,8,11-tetraoxatridecan-13-yl)carbamoyl)-2-oxo-2H-chromen-7-yl)carbamate (S6): A vial was charged with S3 (50 mg, 0.15 mmol), PEG-NH$_2$ (37 mg, 0.18 mmol, 1.2 eq.), EDC (34 mg, 0.18 mmol, 1.2 eq.), HOBT (24 mg, 0.18 mmol, 1.2 eq.) and DMF (3 mL). The reaction was then stirred at room temperature and ambient atmosphere for 24 h. The reaction was concentrated. The crude product was purified via silica gel chromatography (0-10% MeOH/DCM, linear gradient) to afford S6 (67 mg, 85%). ¹H NMR (CDCl₃, 400 MHz): δ9.01 (s, 1H), 8.72 (s, 1H), 8.21 (s, 1H), 7.73 (s, 1H), 7.50 (d, J=8.6 Hz, 1H), 7.40-7.30 (m, 6H), 5.22 (s, 2H), 3.70-3.57 (m, 14H), 3.52 (t, J=4.5 Hz, 2H), 3.34 (s, 3H).

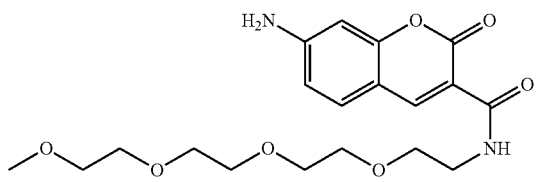 [SMILES: COCCOCCOCCOCCNC(=O)c1cc2ccc(N)cc2oc1=O]

7-amino-2-oxo-N-(2,5,8,11-tetraoxatridecan-13-yl)-2H-chromene-3-carboxamide (S7): A round bottomed flask was charged with S6 (67 mg, 0.13 mmol), Pd/C (2 mg, 0.13 mmol, 0.1 eq.) and EtOAc (3 mL). The flask was sealed with a rubber septum and and evacuated/backfilled first with argon (3×), then with hydrogen gas (3×) via a balloon. The reaction was then stirred at room temperature and hydrogen atmosphere (via a balloon) for 48 hours. The reaction mixture was deposited on celite, concentrated, and the crude product was purified via silica gel chromatography (0-10% MeOH/DCM, linear gradient) to afford S7 (33 mg, 65%). ¹H NMR (CDCl₃, 400 MHz): δ8.97 (t, J=5.3 Hz, 1H), 8.61 (s, 1H), 7.33 (d, J=8.5 Hz, 1H), 6.59 (dd, J=8.5, 2.2 Hz, 1H), 6.54 (d, J=2.1 Hz, 1H), 4.96 (s, 2H), 3.75-3.58 (m, 14H), 3.58-3.48 (m, 2H), 3.38 (s, 3H).

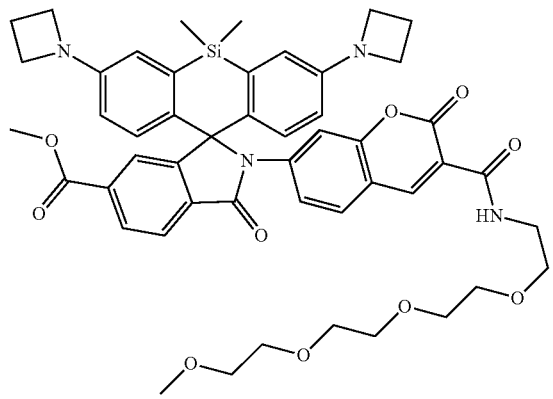 [SMILES: COCCOCCOCCOCCNC(=O)c1cc2ccc(N3C(=O)c4ccc(C(=O)OC)cc4C34c3ccc(N5CCC5)cc3[Si](C)(C)c3cc(N5CCC5)ccc34)cc2oc1=O]

methyl 2'-(3-((2,5,8,11-tetraoxatridecan-13-yl)carbamoyl)-2-oxo-2H-chromen-7-yl)-3,7-di(azetidin-1-yl)-5,5-dimethyl-3'-oxo-5H-spiro[dibenzo[b,e]siline-10,1'-isoindoline]-6'-carboxylate (S8): A vial was charged with JF646-6-OMe (12 mg, 0.023 mmol), oxalyl chloride (3 μL, 0.028 mmol, 1.2 eq.) and DCM (2.00 mL) and the content was stirred at room temperature and ambient atmosphere for 30 minutes. S7 (28 mg, 0.070 mmol, 3 eq.) and DIEA (42 μL, 0.235 mmol, 10 eq.) were then added and the contents were stirred for 1 h, after which the solvent was concentrated to dryness, and the crude product was purified by silica gel chromatography (0-5% MeOH/DCM, linear gradient) to afford S7 (7.2 mg, 35%). ¹H NMR (CDCl₃, 400 MHz): δ8.98 (d, J=6.0 Hz, 1H), 8.68 (d, J=0.7 Hz, 1H), 8.01 (d, J=1.0 Hz, 2H), 7.68 (dd, J=8.7, 2.1 Hz, 1H), 7.64 (d, J=2.1 Hz, 1H), 7.55-7.49 (m, 1H), 7.38 (d, J=8.8 Hz, 1H), 6.76 (d, J=8.8 Hz, 2H), 6.61 (d, J=2.7 Hz, 2H), 6.23 (dd, J=8.8, 2.6 Hz, 2H), 3.88 (t, J=7.3 Hz, 8H), 3.81 (s, 3H), 3.70-3.60 (m, 14H), 3.58-3.51 (m, 2H), 3.37 (s, 3H), 2.35 (p, J=7.2 Hz, 4H), 0.71 (s, 3H), 0.57 (s, 3H).

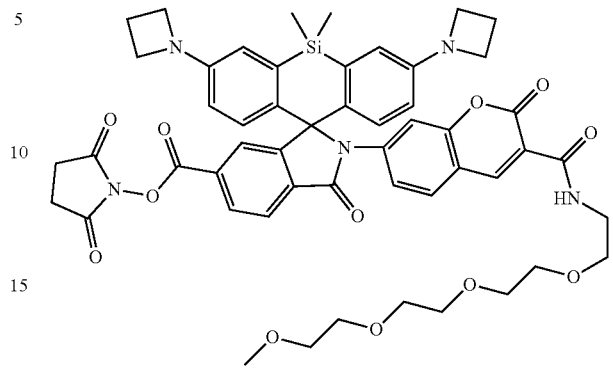

2,5-dioxopyrrolidin-1-yl 2'-(3-((2,5,8,11-tetraoxatridecan-13-yl)carbamoyl)-2-oxo-2H-chromen-7-yl)-3,7-di(azetidin-1-yl)-5,5-dimethyl-3'-oxo-5H-spiro[dibenzo[b,e]siline-10,1'-isoindoline]-6'-carboxylate (PC-JF646-PEG-NHS): A vial was charged with S8 (7 mg, 0.008 mmol), NaOH (80 μL, 1M, 10 eq.) MeOH (1.0 mL) and THF (0.5 mL). Content was stirred at room temperature and ambient atmosphere for 24 h, after which HCl (85 μL, 1M, 10.5 eq.) was added to quench the reaction. The organic layer was extracted with DCM (3×10 mL). Organic layers combined, dried (Na₂SO₄), and concentrated. The hydrolyzed residue was carried to the next step without further purification. A vial was charged with hydrolyzed S8 (6.8 mg, 0.008 mmol), TSTU (7 mg, 0.023 mmol, 3 eq.), DIEA (14 μL, 0.08 mmol, 10 eq.) and DMF (300 μL). Contents were stirred at room temperature and ambient atmosphere for 24 h, after which the solvent was concentrated to dryness, and the crude product was purified by silica gel chromatography (0-70% Acetone/DCM, linear gradient) to afford PC-JF646-PEG-NHS (1.3 mg, 17%). LRMS (ESI) calcd for C₅₈H₇₂ClN₅O₁₁Si [M]⁺ 1078.8, found 1078.5

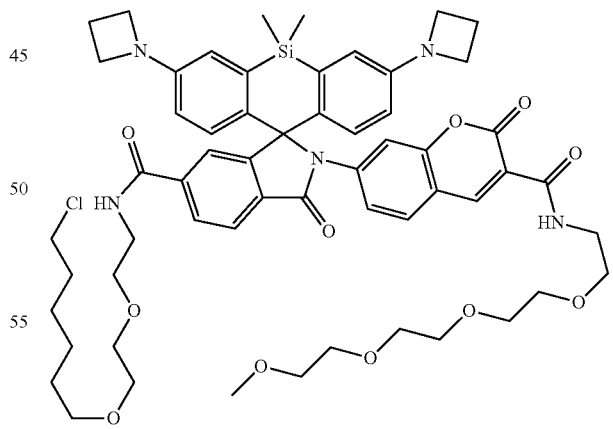

2'-(3-((2,5,8,11-tetraoxatridecan-13-yl)carbamoyl)-2-oxo-2H-chromen-7-yl)-3,7-di(azetidin-1-yl)-N-(2-(2-((6-chlorohexyl)oxy)ethoxy)ethyl)-5,5-dimethyl-3'-oxo-5H-spiro[dibenzo[b,e]siline-10,1'-isoindoline)-6'-carboxamide (PC-JF646-PEG-HT): A vial was charged with S8 (14 mg, 0.016 mmol), NaOH (160 μL, 1M, 10 eq.) MeOH (1.0 mL) and THF (0.5 mL). Content was stirred at room temperature and ambient atmosphere for 24 h, after which HCl (168 µL, 1M, 10.5 eq.) was added to quench the reaction. The organic layer was extracted with DCM (3×10 mL). Organic layers combined, dried (Na$_2$SO$_4$), and concentrated. The hydrolyzed residue was carried to the next step without further purification. A vial was charged with hydrolyzed S8 (14 mg, 0.016 mmol), HTL (16 mg, 0.048, 3 eq.), HATU (18 mg, 0.048 mmol, 3 eq.), DIEA (28 µL, 0.16 mmol, 10 eq.) and DMF (500 µL). Contents were stirred at room temperature and ambient atmosphere for 24 h, after which the solvent was concentrated to dryness, and the crude product was purified by silica gel chromatography (0-5% MeOH/DCM, linear gradient) to afford PC-JF646-PEG-HT (13 mg, 75%). $^1$H NMR (CDCl$_3$, 400 MHz): δ8.98 (d, J=5.6 Hz, 1H), 8.67 (s, 1H), 7.99 (s, 1H), 7.69 (dd, J=8.0, 1.4 Hz, 1H), 7.66-7.61 (m, 2H), 7.37 (d J=9.6 Hz, 1H), 7.29 (s, 1H), 6.75 (d, J=8.7 Hz, 2H), 6.64 (t, J=5.4 Hz, 1H), 6.60 (d, J=2.6 Hz, 2H), 6.23 (dd, J=8.8, 2.6 Hz, 2H), 3.88 (t, J=7.2 Hz, 8H), 3.76-3.49 (m, 26H), 3.40 (t, J=6.6 Hz, 2H), 3.37 (s, 3H), 2.35 (p, J=7.2 Hz, 4H), 1.83-1.70 (m, 2H), 1.58-1.48 (m, 2H), 1.37-1.26 (m, 4H), 0.69 (s, 3H), 0.55 (s, 3H).

5. Synthesis of the Photochromic AlexaFluor Dyes (Scheme 3, FIGS. 25-26)

To further demonstrate the generalizability of this approach in inducing photochromism in fluorophores, these coumarin switches were introduced into the molecular structure of AlexaFluor 594, Scheme 3, at the same position with the JaneliaFluor dyes. The chemistry can be extended to other AlexaFluor dyes as well. AlexaFluor dyes are more polar and hence water soluble, so they are ideal antibody labels for immunofluorescence.

The synthesis of PC-AF549-NHS, starts with the advanced intermediates, S1 and S2, which were synthesized from the condensation of the commercially available 1,2-Dihydro-1,2,2,4-tetramethyl-7-quinolinol; 1,2-Dihydro-1,2,2,4-tetramethylquinolin-7-ol and trimellitic anhydride as described elsewhere.[7] The 5'- and 6'-carboxy isomers were separated by reverse phase HPLC (30-60% MeCN/H$_2$O, linear gradient, with constant 0.1% v/v TFA additive; 23 min run, 42 mL/min flow, detection at 500 nm). The 6'-isomer eluting after 11.75 mins, and the 5'-isomer eluting after 12.5 mins. The combined yield of the two isomers was 26%, and the 5'-isomer was used in the synthesis of PC-AF594-NHS, while the 6'-isomer was used in the synthesis of the PC-AF594-HT. S1 and S2 were then methylated by first activation with DSC to yield the respective NHS ester, followed by trapping with sodium methoxide to yield the methyl esters. Sulfonating the methyl esters S3 and S4 in conc. sulfuric acid resulted in the sulfonated rhodamines (AlexaFluor549 derivatives) which were then treated with HATU to activate the carboxylate at the 3'-position before amidation with 7-Amino-4-(trifluoromethyl) coumarin to yield photochromic isomers S7 and S8. Upon hydrolysis of the methyl esters in basic conditions, the hydrolyzed 5'-isomer (S9) was then used to install an NHS ester functionality producing PC-AF594-NHS for antibody labeling, while the hydrolyzed 6'-isomer (S10) was used to install a HTL to produce PC-AF594-HT for labeling HaloTag protein.

Through similar chemical transformations, it is also possible to attach other biological handles to the photochromic AF594, and other Alexafluors, such as SNAP-Tag or click-chemistry substrates, which will increase the number of biological targets that can be specifically labeled with these fluorophores.

Figure 26:
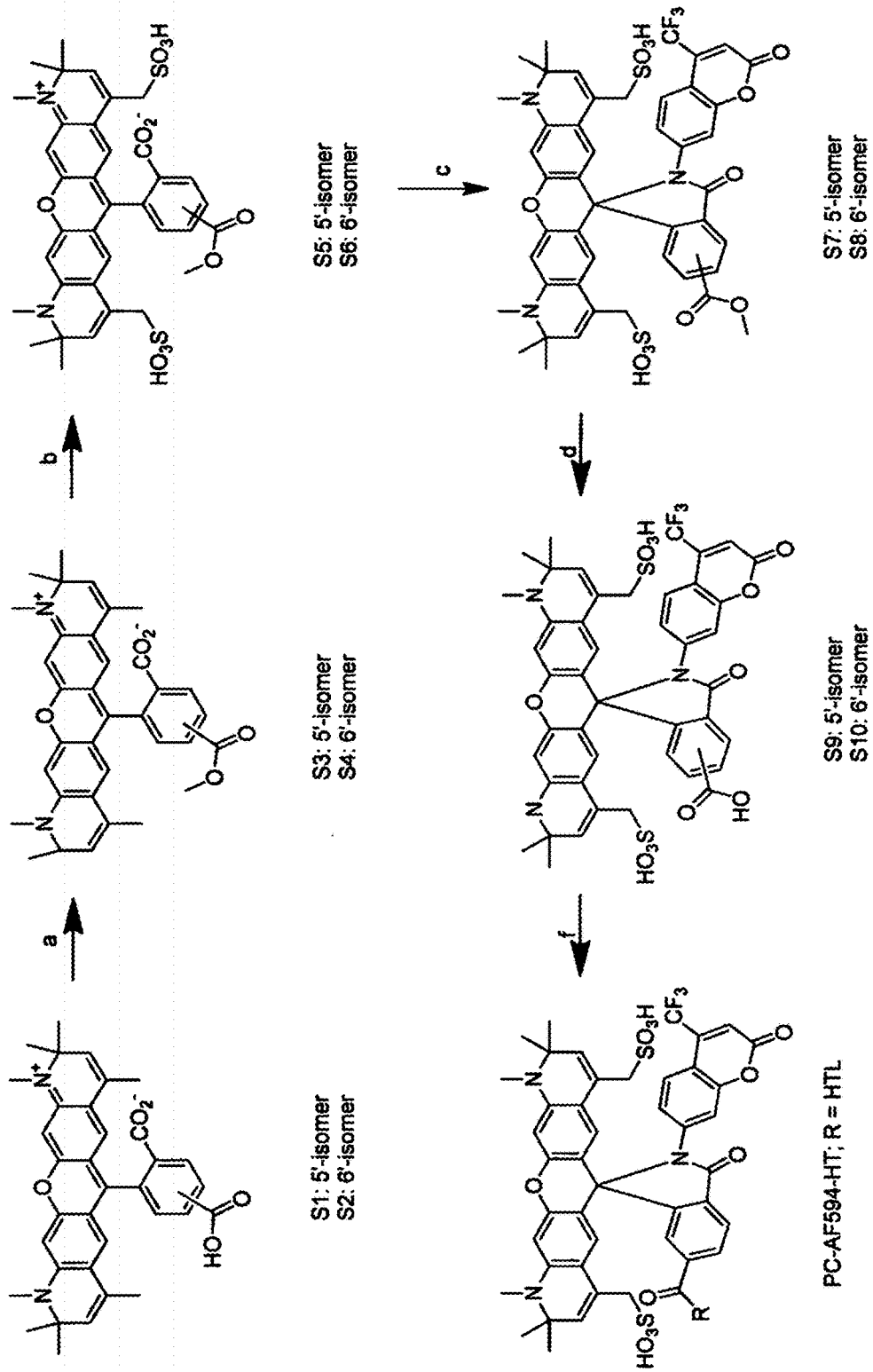
Figure 27:
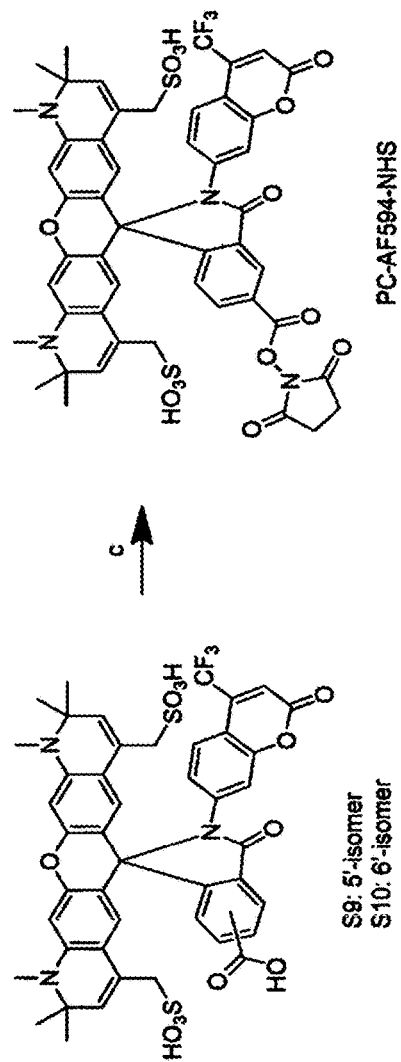
Figure 27:

6. General Experimental Information for Synthesis of Compounds for Scheme 3 (FIGS. 26-27)

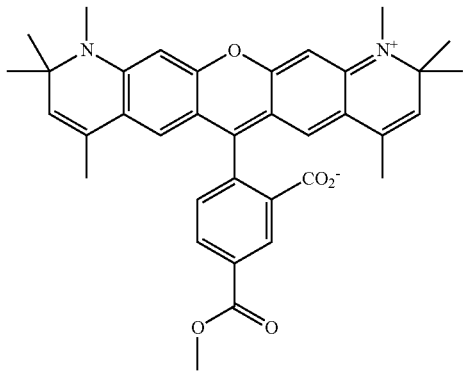

5-(methoxycarbonyl)-2-(1,2,2,4,8,10,10,11-octamethyl-10,11-dihydro-2H-pyrano[3,2-g:5,6-g']diquinolin-1-ium-6-yl)benzoate (S3): A vial was charged with S1 (50 mg, 0.088 mmol), DSC (68 mg, 0.267 mmol, 3 eq.), DMAP (1 mg, 0.009 mmol, 0.1 eq.), Et$_3$N (73 µL, 0.528 mmol, 6 eq.) and DMF (300 µL). Contents were stirred at room temperature and ambient atmosphere for 1 h, after which NaOMe (77 µL, 0.355 mmol, 25% wt/wt in MeOH, 4 eq.) and the mixture stirred for 24 h. Solvent was concentrated to dryness, and the crude product was purified by reverse phase HPLC (20-80% MeCN/H$_2$O, linear gradient, with constant 0.1% v/v TFA additive; 23 min run, 42 mL/min flow, detection at 050 nm) to afford S3 (30 mg, 60%). LRMS (ESI) calcd for C$_{36}$H$_{36}$N$_2$O$_5$ [M]$^+$ 576.7, found 577.3

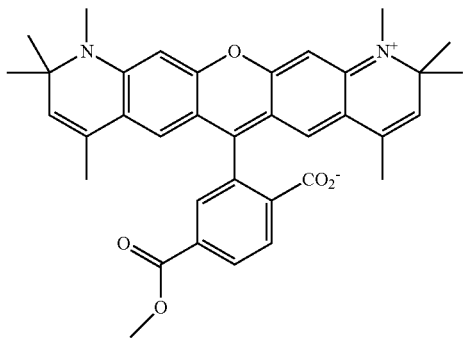

4-(methoxycarbonyl)-2-(1,2,2,4,8,10,10,11-octamethyl-10,11-dihydro-2H-pyrano[3,2-g:5,6-g']diquinolin-1-ium-6-yl)benzoate (S4): A vial was charged with S2 (30 mg, 0.053 mmol), DSC (41 mg, 0.156 mmol, 3 eq.), DMAP (0.7 mg, 0.005 mmol, 0.1 eq.), Et$_3$N (44 µL, 0.32 mmol, 6 eq.) and DMF (300 µL). Contents were stirred at room temperature and ambient atmosphere for 1 h, after which NaOMe (48 µL, 0.213 mmol, 25% wt/wt in MeOH, 4 eq.) and the mixture stirred for 24 h. Solvent was concentrated to dryness, and the crude product was purified by reverse phase HPLC (20-80% MeCN/H$_2$O, linear gradient, with constant 0.1% v/v TFA additive; 23 min run, 42 mL/min flow, detection at 050 nm) to afford S4 (19 mg, 60%). LRMS (ESI) calcd for C$_{36}$H$_{36}$N$_2$O$_5$[M]$^+$ 576.7, found 577.2.

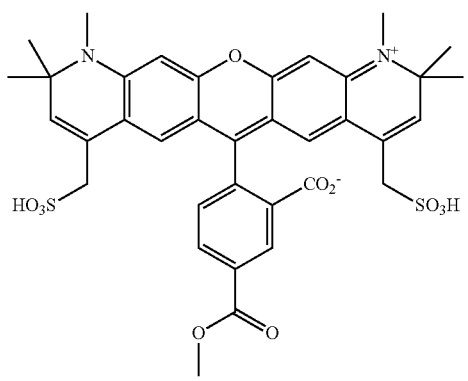

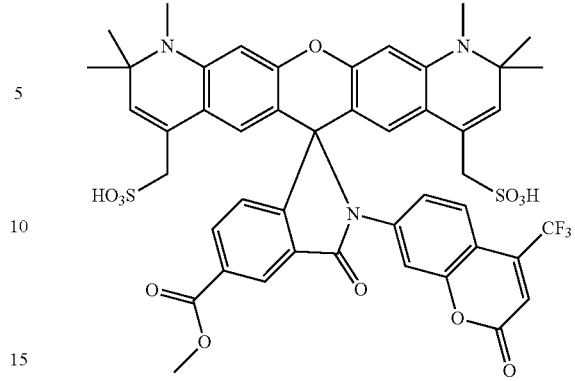

2-(1,2,2,10,10,11-hexamethyl-4,8-bis(sulfomethyl)-10,11-dihydro-2H-pyrano[3,2-g:5,6-g']diquinolin-1-ium-6-yl)-5-(methoxycarbonyl)benzoate (S5): A vial was charged with S3 (30 mg, 0.052 mmol) and conc. H$_2$SO$_4$ (2 mL). Contents were stirred at room temperature and ambient atmosphere for 72 h, after which the reaction was cooled down to 0° C. and cool water was added dropwise to dilute the mixture before loading it on a reverse phase C18 silica gel chromatography column. The column was washed with copious amounts of water until the pH of the filtrate is adjusted to around 5. The sulfonated rhodamine was then eluted with CH$_3$CN to afford S5 (20 mg, 38%). LRMS (ESI) calcd for C$_{36}$H$_{36}$N$_2$O$_{11}$S$_2$ [M]$^+$ 736.8, found 737.3

(5-(methoxycarbonyl)-1',2',2',10',10',11'-hexamethyl-3-oxo-2-(2-oxo-4-(trifluoromethyl)-2H-chromen-7-yl)-1',2',10',11'-tetrahydrospiro[isoindoline-1,6'-pyrano[3,2-g:5,6-g']diquinoline]-4',8'-diyl)dimethanesulfonic acid (S7): A vial was charged with S5 (20 mg, 0.027 mmol), 7-amino-4-(trifluoromethyl)coumarin (19 mg, 0.081 mmol, 3 eq.), HATU (31 mg, 0.081 mmol, 3 eq.), Et$_3$N (76 µL, 0.543 mmol, 20 eq.) and DMF (500 µL). Contents were stirred at room temperature and ambient atmosphere for 24 h, after which the solvent was concentrated to dryness, and the crude product was purified via reverse phase HPLC (10-95% MeCN/H$_2$O, linear gradient, with constant 0.1% v/v TFA additive; 23 min run, 42 mL/min flow, detection at 550 nm) to afford S7 (11 mg, 42%). LRMS (ESI) calcd for C$_{46}$H$_{40}$F$_3$N$_3$O$_{12}$S$_2$ [M]$^+$ 948.0, found 948.1

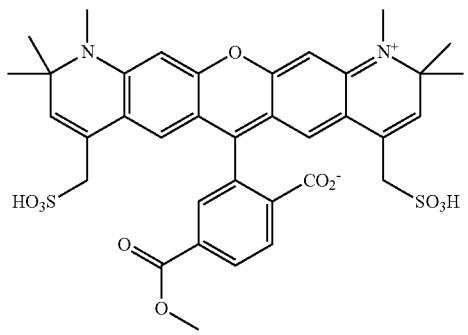

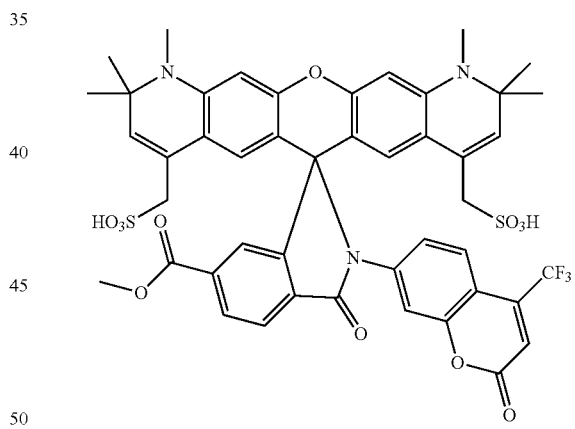

2-(1,2,2,10,10,11-hexamethyl-4,8-bis(sulfomethyl)-10,11-dihydro-2H-pyrano[3,2-g:5,6-g']diquinolin-1-ium-6-yl)-4-(methoxycarbonyl)benzoate (S6): A vial was charged with S4 (18 mg, 0.031 mmol) and conc. H$_2$SO$_4$ (1 mL). Contents were stirred at room temperature and ambient atmosphere for 72 h, after which the reaction was cooled down to 0° C. and cool water was added dropwise to dilute the mixture before loading it on a reverse phase C18 silica gel chromatography column. The column was washed with copious amounts of water until the pH of the filtrate is adjusted to around 5. The sulfonated rhodamine was then eluted with CH$_3$CN to afford S6 (22 mg, 96%). LRMS (ESI) calcd for C$_{36}$H$_{36}$N$_2$O$_{11}$S$_2$ [M]$^+$ 736.8, found 737.3

(6-(methoxycarbonyl)-1',2',2',10',10',11'-hexamethyl-3-oxo-2-(2-oxo-4-(trifluoromethyl)-2H-chromen-7-yl)-1',2',10',11'-tetrahydrospiro[isoindoline-1,6'-pyrano[3,2-g:5,6-g']diquinoline]-4', 8'-diyl)dimethanesulfonic acid (S8): A vial was charged with S6 (20 mg, 0.027 mmol), 7-amino-4-(trifluoromethyl)coumarin (19 mg, 0.081 mmol, 3 eq.), HATU (31 mg, 0.081 mmol, 3 eq.), Et$_3$N (76 µL, 0.543 mmol, 20 eq.) and DMF (500 µL). Contents were stirred at room temperature and ambient atmosphere for 24 h, after which the solvent was concentrated to dryness, and the crude product was purified via reverse phase HPLC (10-95% MeCN/H$_2$O, linear gradient, with constant 0.1% v/v TFA additive; 23 min run, 42 mL/min flow, detection at 550 nm) to afford S7 (8 mg, 31%). LRMS (ESI) calcd for C$_{46}$H$_{40}$F$_3$N$_3$O$_{12}$S$_2$ [M]$^+$ 948.0, found 948.1

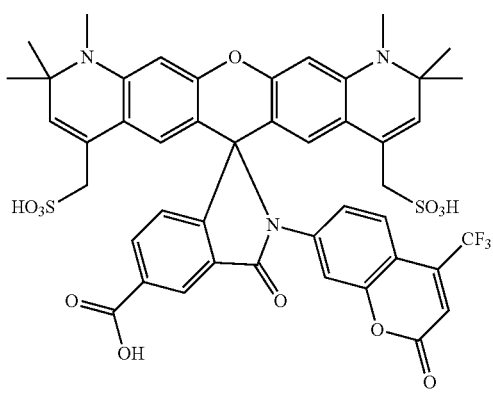 [SMILES: CN1c2cc3c(cc2C(CS(=O)(=O)O)=CC1(C)C)C1(c2cc4c(cc2O3)N(C)C(C)(C)C=C4CS(=O)(=O)O)c2ccc(C(=O)O)cc2C(=O)N1c1ccc2c(C(F)(F)F)cc(=O)oc2c1]

1',2',2',10',10',11'-hexamethyl-3-oxo-2-(2-oxo-4-(trifluoromethyl)-2H-chromea-7-yl)-4',8'-bis(sulfomethyl)-1',2',10',11'-tetrahydrospiro[isoindoline-1,6'-pyrano[3,2-g:5,6-g']diquinoline]-5-carboxylic acid (S9): A vial was charged with S7 (11 mg, 0.011 mmol), NaOH (110 µL, 1M, 10 eq.) and MeOH (1.0 mL). Content was stirred at room temperature and ambient atmosphere for 24 h, after which HCl (116 µL, 1M, 10.5 eq.) was added to quench the reaction and the content stirred for 2 h. The content was concentrated and the hydrolyzed residue was purified by reverse phase HPLC (30-70% MeCN/H$_2$O, linear gradient, with constant 0.1% v/v TFA additive; 23 min run, 42 mL/min flow, detection at 550 nm) to afford S9 (5.5 mg, 51%). LRMS (ESI) calcd for C$_{45}$H$_{38}$F$_3$N$_3$O$_{12}$S$_2$ [M]$^+$ 933.9, found 934.1

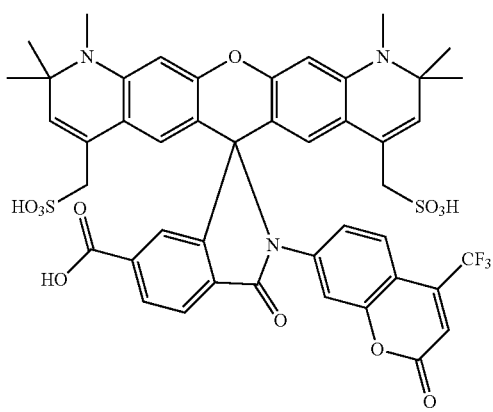 [SMILES: CN1c2cc3c(cc2C(CS(=O)(=O)O)=CC1(C)C)C1(c2cc4c(cc2O3)N(C)C(C)(C)C=C4CS(=O)(=O)O)c2cc(C(=O)O)ccc2C(=O)N1c1ccc2c(C(F)(F)F)cc(=O)oc2c1]

1',2',2',10',10',11'-hexamethyl-3-oxo-2-(2-oxo-4-(trifluoromethyl)-2H-chromen-7-yl)-4',8'-bis(sulfomethyl)-1',2',10',11'-tetrahydrospiro[isoindoline-1,6'-pyrano[3,2-g:5,6-g']diquinoline]-6-carboxylic acid (S10): A vial was charged with S8 (8 mg, 0.008 mmol), NaOH (80 µL, 1M, 10 eq.) and MeOH (1.0 mL). Content was stirred at room temperature and ambient atmosphere for 24 h, after which HCl (88 µL, 1M, 10.5 eq.) was added to quench the reaction and the content stirred for 2 h. The content was concentrated and the hydrolyzed residue was purified by reverse phase HPLC (10-90% MeCN/H$_2$O, linear gradient, with constant 0.1% v/v TFA additive; 23 min run, 42 mL/min flow, detection at 550 nm) to afford S9 (2 mg, 25%). LRMS (ESI) calcd for C$_{45}$H$_{38}$F$_3$N$_3$O$_{12}$S$_2$ [M]$^+$ 933.9, found 934.3

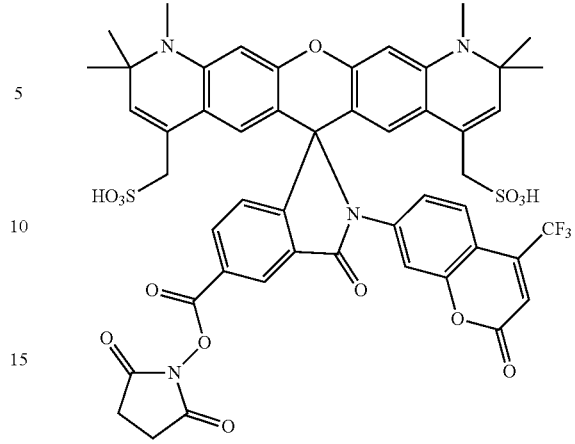

(5-(((2,5-dioxopyrrolidin-1-yl)oxy)carbonyl)-1',2',2',10',10',11'-hexamethyl-3-oxo-2-(2-oxo-4-(trifluoromethyl)-2H-chromen-7-yl)-1',2',10',11'-tetrahydrospiro[isoindoline-1,6'-pyrano[3,2-g:5,6-g']diquinoline]-4',8'-diyl) dimethanesulfonic acid (PC-AF594-NHS): A vial was charged with S9 (1 mg, 0.001 mmol), TSTU (0.5 mg, 0.0015 mmol, 1.5 eq.), DIEA (0.6 µL, 0.003 mmol, 3 eq.) and DMF (50 µL). Contents were stirred at room temperature and ambient atmosphere for 1 h, after which the solvent was diluted with CH$_3$CN to dryness, and the purified by reverse phase HPLC (10-90% MeCN/H$_2$O, linear gradient, in 10 mM triethylammonium formate buffer, 23 min run, 42 mL/min flow, detection at 550 nm) to afford afford PC-AF594-NHS (1 mg, 99%). LRMS (ESI) calcd for C$_{49}$H$_{41}$F$_3$N$_4$O$_{14}$S2 [M]$^+$ 1031.0, found 1031.2

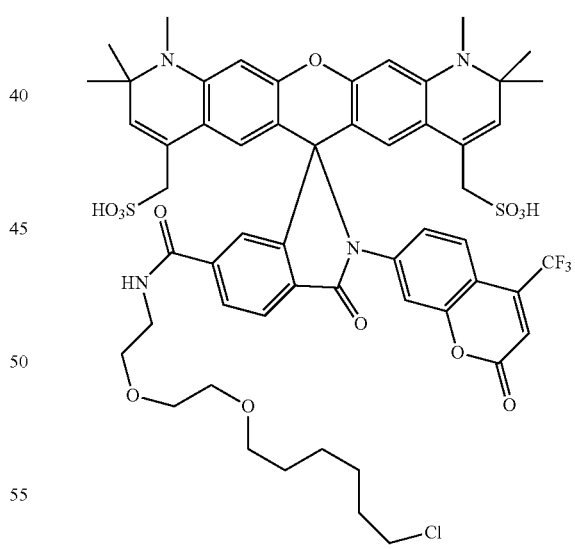

(6-((2-(2-((6-chlorohexyl)oxy)ethoxy)ethyl)carbamoyl)-1',2',2',10',10',11'-hexamethyl-3-oxo-2-(2-oxo-4-(trifluoromethyl)-2H-chromen-7-yl)-1',2',10',11'-tetrahydrospiro[isoindoline-1,6'-pyrano[3,2-g:5,6-g']diquinoline]-4',8'-diyl) dimethanesulfonic acid (PC-AF594-HT): A vial was charged with S10 (2 mg, 0.002 mmol), HTL (3 mg, 0.006, 3 eq.), HATU (3 mg, 0.006 mmol, 3 eq.), DIEA (4 µL, 0.02 mmol, 10 eq.) and DMF (300 µL). Contents were stirred at room temperature and ambient atmosphere for 24 h, after which the solvent was concentrated to dryness, and the crude product was purified by reverse phase HPLC (10-90% MeCN/H$_2$O, linear gradient, with constant 0.1% v/v TFA additive; 23 min run, 42 mL/min flow, detection at 550 nm) to afford PC-AF594-HT (1.2 mg, 49%). LRMS (ESI) calcd for $C_{55}H_{58}ClF_3N_4O_{13}S_2$ [M]$^+$ 1139.7, found 1139.3

7. Synthesis of the Photochromic Azepine Dyes (Scheme 4)

Finally, it is also possible to render rhodamine dyes with different amino substituents on their xanthene core photochromic by introducing the coumarin switch. Rhodamine with an azepane ring (S1), and rhodamine 640 perchlorate (S2), Scheme 4, were activated by HATU, prior to amidation with 7-amino-4-(trifluoromethyl) coumarin in the presence of Hünig's base.

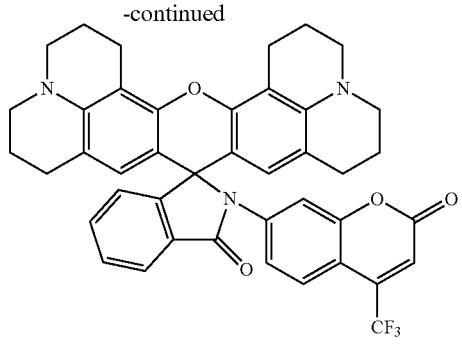

PC-Rh$_{640}$

Scheme 1. Synthesis of PC-Azep. a. HATU, DIEA, DMF, 7-amino-4-(trifluoromethyl) coumarin, RT, 24 h.

8. General Experimental Information for Synthesis of Compounds for Scheme 4

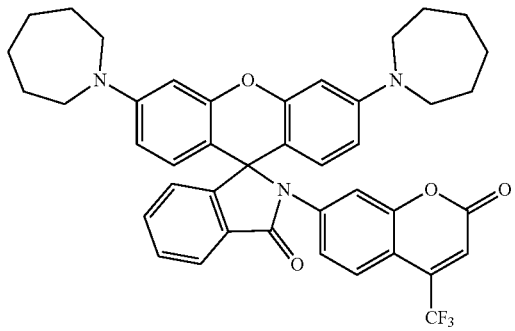 [SMILES: O=C1c2ccccc2C2(c3ccc(N4CCCCCC4)cc3Oc3cc(N4CCCCCC4)ccc32)N1c1ccc2c(C(F)(F)F)cc(=O)oc2c1]

3',6'-di(azepan-1-yl)-2-(2-oxo-4-(trifluoromethyl)-2H-chromen-7-yl)spiro[isoindoline-1,9'-xanthen]-3-one (PC-Azep): A vial was charged with S1$^1$ (25 mg, 0.05 mmol), 7-amino-4-(trifluoromethyl) coumarin (23 mg, 0.10 mmol, 3 eq.), HATU (23 mg, 0.06 mmol, 1.2 eq.), DIEA (26 µL, 0.151 mmol, 3 eq.) and DMF (1 mL). Contents were stirred at room temperature and ambient atmosphere for 24 h, after which the solvent was concentrated to dryness, and the crude product was purified via silica gel chromatography (0-10% MeOH/DCM, linear gradient) to afford PC-Azep (15 mg, 42%). $^1$H NMR (CDCl$_3$, 400 MHz) δ7.90 (d, J=8 Hz, 1H), 7.52-7.38 (m, 3H), 7.32-7.23 (m, 2H), 7.01 (dd, J=6.9, 1.4 Hz, 1H), 6.59-6.49 (m, 3H), 6.33 (d, J=2.6 Hz, 2H), 6.25 (dd, J=8.9, 2.6 Hz, 2H), 5.25 (s, 1H), 3.34 (t, J=6.0 Hz, 8H), 1.74-1.63 (m, 8H), 1.60-1.46 (m, 8H).

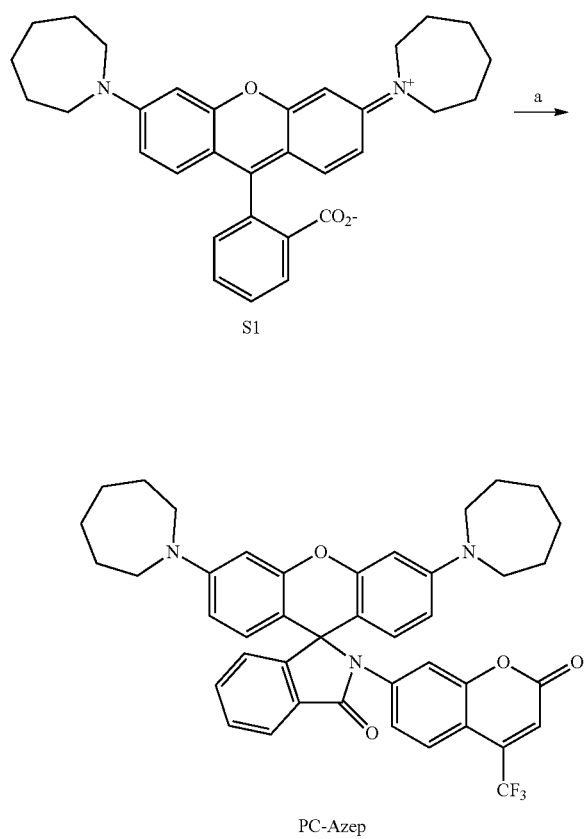

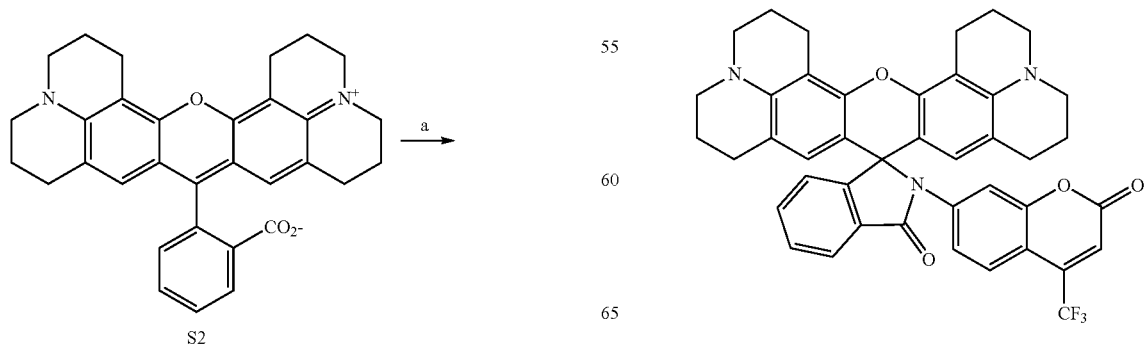

(PC-Rh$_{640}$): A vial was charged with S2 (50 mg, 0.08 mmol), 7-amino-4-(trifluoromethyl) coumarin (30 mg, 0.17 mmol, 2 eq.), HATU (39 mg, 0.10 mmol, 1.2 eq.), DIEA (42 µL, 0.24 mmol, 3 eq.) and DMF (1 mL). Contents were stirred at room temperature and ambient atmosphere for 24 h, after which the solvent was concentrated to dryness, and the crude product was purified via silica gel chromatography (0-10% MeOH/DCM, linear gradient) to afford PC-Rh$_{640}$ (30 mg, 55%).

REFERENCES

1. Grimm, J. B.; English, B. P.; Chen, J.; Slaughter, J. P.; Zhang, Z.; Revyakin, A.; Patel, R.; Macklin, J. J.; Normanno, D.; Singer, R. H., *Nature methods* 2015, 12, 3, 244.
2. Los, G. V.; Encell, L. P.; McDougall, M. G.; Hartzell, D. D.; Karassina, N.; Zimprich, C.; Wood, M. G.; Learish, R.; Ohana, R. F.; Urh, M., *ACS chemical biology* 2008, 3, 6, 373.
3. Juillerat, A.; Gronemeyer, T.; Keppler, A.; Gendreizig, S.; Pick, H.; Vogel, H.; Johnsson, K., *Chemistry & biology* 2003, 10, 4, 313.
4. Friedman Ohana, R.; Levin, S.; Wood, M. G.; Zimmerman, K.; Dart, M. L.; Schwinn, M. K.; Kirkland, T. A.; Hurst, R.; Uyeda, H. T.; Encell, L. P., *ACS chemical biology* 2016, 11, 9, 2608.
5. Lukinavičius, G.; Reymond, L.; D'este, E.; Masharina, A.; Göttfert, F.; Ta, H.; Güther, A.; Fournier, M.; Rizzo, S.; Waldmann, H., *Nature methods* 2014, 11, 7, 731.
6. Szíjjártó, C.; Pershagen, E.; Ilchenko, N. O.; Borbas, K. E., *Chemistry-A European Journal* 2013, 19, 9, 3099.
7. Belov, V. N.; Mitronova, G. Y.; Bossi, M. L.; Boyarskiy, V. P.; Hebisch, E.; Geisler, C.; Kolmakov, K.; Wurm, C. A.; Willig, K. I.; Hell, S. W., *Chemistry-A European Journal* 2014, 20, 41, 13162.

The invention claimed is:

1. A method of imaging one or more cellular structures within one or more cells, wherein the method comprises the steps of:
    a) labeling one or more cells with a compound of the following structure

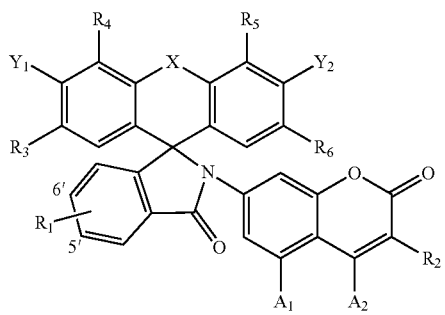

wherein,
X is O, N-alkyl, S, Si(alkyl)$_2$ or C(alkyl)$_2$;
Y$_1$ is O, OH, NH$_2$, N(alkyl)$_2$ or one of the following moieties

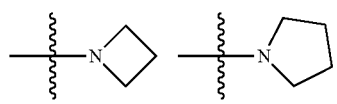

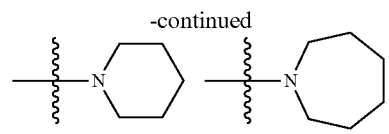

Y$_2$ is O, OH, NH$_2$, N(alkyl)$_2$ or one of the following moieties

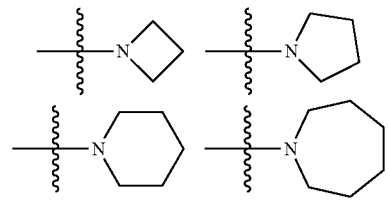

R$_1$, which can be a substitution at either the 5' position, the 6' position or both, is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl;

R$_2$ is hydrogen, C(O)NH-Handle, C(O)-linker-Handle, C(O)NH-Acceptor, C(O)-linker-Acceptor, C(O)NH-linker-CH2-X where X is a leaving group, C(O)NH—(CH$_2$CH$_2$)$_n$C(O)N(H)-Handle where "n" is an integer ranging from 1 to 100, C(O)NH—(CHCH)$_n$-Acceptor where "n" is an integer ranging from 1 to 100, C(O)NH—(CH$_2$CH$_2$O)$_3$—C(O)NH—(CH$_2$CH$_2$O)$_2$-(CH2)$_6$-Cl, or C(O)NH—(CH$_2$CH$_2$O)$_3$—C(O)NH—(CH$_2$CH$_2$O)$_3$—C(O)NH—(CH$_2$CH$_2$O)$_2$—(CH$_2$)$_6$—Cl;

R$_3$, R$_4$, R$_5$ and R$_6$ are independently hydrogen, alkyl, —SO$_3$H, halogen, or R$_3$ and Y$_1$ can form a ring, or R$_4$ and Y$_1$ can form a ring, or R$_5$ and Y$_2$ can form a ring, or R$_6$ and Y$_2$ can form a ring;

A$_1$ is hydrogen, alkyl, alkenyl, alkynyl, heteroalkyl, heteroalkenyl, cycloalkyl, cycloalkenyl, heterocycloalkyl, heterocycloalkenyl, aromatic, heteroaromatic, substituted alkyl, substituted alkenyl, substituted alkynyl, substituted heteroalkyl, substituted heteroalkenyl, heterocycloalkyl, heterocycloalkenyl, substituted aromatic group, or substituted heteroaromatic group;

A$_2$ is hydrogen, alkyl, alkenyl, alkynyl, heteroalkyl, heteroalkenyl, cycloalkyl, cycloalkenyl, heterocycloalkyl, heterocycloalkenyl, aromatic, heteroaromatic, substituted alkyl, substituted alkenyl, substituted alkynyl, substituted heteroalkyl, substituted heteroalkenyl, heterocycloalkyl, heterocycloalkenyl, substituted aromatic group, or substituted heteroaromatic group, to provide one or more labeled cells
    b) directing at least one beam of light to the one or more labeled cells, such that a detectable signal is produced from the one or more labeled cells;
    c) recording the detectable signal, thereby imaging one or more structures within the one or more cells.

2. The method according to claim 1, wherein X of the structure is O, $Y_1$ is one of the following moieties

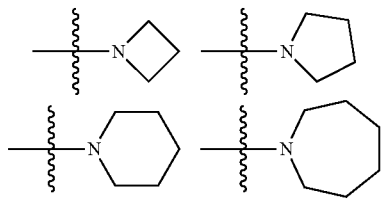

and $Y_2$ is one of the following moieties

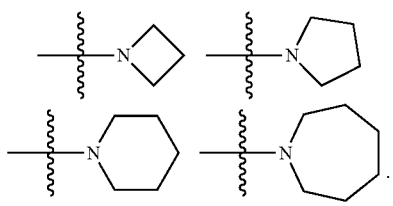

3. The method according to claim 2, wherein $R_2$ of the structure is a Handle, $A_1$ is hydrogen, alkyl, or substituted alkyl.

4. The method according to claim 3, wherein $A_2$ is hydrogen, alkyl, or substituted alkyl.

5. The method according to claim 4, wherein $R_4$ and $R_5$ are $SO_3H$.

* * * * *